(12) United States Patent
Schreiber

(10) Patent No.: US 11,076,896 B2
(45) Date of Patent: Aug. 3, 2021

(54) POSITIONING-DEVICE MODULE FOR RELEASABLE CONNECTION TO A POSITIONING DEVICE, POSITIONING DEVICE AND SET

(71) Applicant: OT MEDIZINTECHNIK GMBH, Munich (DE)

(72) Inventor: Ulrich Schreiber, Munich (DE)

(73) Assignee: OT MEDIZINTECHNIK GMBH, Munich (DE)

( * ) Notice: Subject to any disclaimer, the term of this patent is extended or adjusted under 35 U.S.C. 154(b) by 254 days.

(21) Appl. No.: 16/071,643

(22) PCT Filed: Jan. 19, 2017

(86) PCT No.: PCT/EP2017/051055
§ 371 (c)(1),
(2) Date: Jul. 20, 2018

(87) PCT Pub. No.: WO2017/125476
PCT Pub. Date: Jul. 27, 2017

(65) Prior Publication Data
US 2019/0192199 A1 Jun. 27, 2019

(30) Foreign Application Priority Data

Jan. 20, 2016 (DE) .......................... 102016100953.9
May 31, 2016 (DE) .......................... 102016110060.9
(Continued)

(51) Int. Cl.
*A61B 17/17* (2006.01)
*A61B 17/88* (2006.01)
(Continued)

(52) U.S. Cl.
CPC ...... *A61B 17/7233* (2013.01); *A61B 17/1703* (2013.01); *A61B 17/1725* (2013.01);
(Continued)

(58) Field of Classification Search
CPC . A61B 17/7233; A61B 90/11; A61B 17/1703; A61B 17/1725; A61B 17/1728;
(Continued)

(56) References Cited

U.S. PATENT DOCUMENTS 4,541,424 A 9/1985 Grosse et al.
4,667,664 A 5/1987 Taylor et al.
(Continued)

FOREIGN PATENT DOCUMENTS

DE 4238582 A1 5/1994
DE 29608071 U1 9/1997
(Continued)

*Primary Examiner* — Jessica Weiss
(74) *Attorney, Agent, or Firm* — Millman IP Inc.

(57) ABSTRACT

The present invention relates to a positioning device module for its releasable connection to a positioning device, wherein the positioning device module is prepared and designed for positioning and/or fixing an intramedullary nail in a long bone, for fixing an osteosynthesis plate on a long bone and/or for fixing a prosthesis in a long bone. The positioning device module comprises a targeting device for receiving an interlocking device or an instrument for acting on the interlocking device, a receiving section for receiving the targeting device and optionally a joint or a deformable section for connecting the positioning device module, to the positioning device, Wherein the joint or the deformable section comprises at least one rotary axis. The present invention further relates to a set, comprising a positioning device module according to the present invention and an extension device for connecting the positioning device module to a positioning device.

18 Claims, 43 Drawing Sheets

(30) Foreign Application Priority Data

Jun. 1, 2016 (DE) .................. 102016110153.2
Sep. 21, 2016 (DE) .................. 102016117848.9
Sep. 22, 2016 (DE) .................. 102016117935.3

(51) Int. Cl.

| | | |
|---|---|---|
| *A61B 17/58* | (2006.01) | |
| *A61B 17/72* | (2006.01) | |
| *A61B 90/11* | (2016.01) | |
| *A61B 17/80* | (2006.01) | |
| *A61B 90/00* | (2016.01) | |
| *A61B 17/00* | (2006.01) | |

(52) U.S. Cl.
CPC ........ *A61B 17/1728* (2013.01); *A61B 17/808* (2013.01); *A61B 17/8872* (2013.01); *A61B 90/11* (2016.02); *A61B 2017/00946* (2013.01); *A61B 2090/062* (2016.02)

(58) Field of Classification Search
CPC .............. A61B 17/808; A61B 17/8872; A61B 2090/062; A61B 2017/00946
USPC ..... 606/96–98, 67–68, 62–24, 329, 281, 99, 606/104, 86 B
See application file for complete search history.

(56) References Cited

U.S. PATENT DOCUMENTS

| | | |
|---|---|---|
| 4,976,713 A | 12/1990 | Landanger et al. |
| 5,178,621 A | 1/1993 | Cook et al. |
| 5,234,434 A | 8/1993 | Goble et al. |
| 5,352,228 A | 10/1994 | Kummer et al. |
| 5,433,720 A | 7/1995 | Faccioli et al. |
| 5,474,561 A | 12/1995 | Yao |
| 5,620,449 A | 4/1997 | Faccioli et al. |
| 5,776,194 A | 7/1998 | Mikol et al. |
| 6,039,742 A | 3/2000 | Krettek et al. |
| 6,200,316 B1 | 3/2001 | Zwirkoski et al. |
| 6,514,253 B1 | 2/2003 | Yao |
| 7,056,322 B2 | 6/2006 | Davison et al. |
| 7,311,710 B2 | 12/2007 | Zander |
| 7,549,994 B2 | 6/2009 | Zander et al. |
| 8,182,490 B2 | 5/2012 | Christie |
| 8,968,324 B2 * | 3/2015 | Atkinson ........... A61B 17/1725 606/98 |
| 2002/0151897 A1 | 10/2002 | Zirkle |
| 2012/0253354 A1 | 10/2012 | Arlettaz et al. |
| 2013/0110119 A1* | 5/2013 | Atkinson ........... A61B 17/1725 606/98 |
| 2014/0249536 A1 | 9/2014 | Jajeh |
| 2017/0202566 A1* | 7/2017 | Luo ....................... A61B 17/72 |

FOREIGN PATENT DOCUMENTS

| | | |
|---|---|---|
| DE | 202004014226 U1 | 12/2004 |
| DE | 202011000553 U1 | 6/2011 |
| DE | 102014109935 A1 | 1/2016 |
| WO | 2006105673 A1 | 10/2006 |
| WO | 2006107222 A2 | 10/2006 |
| WO | 2008001386 A2 | 1/2008 |
| WO | WO-2008001386 A2 * | 1/2008 ......... A61B 17/1725 |
| WO | 2010028046 A1 | 3/2010 |
| WO | 2016008849 A1 | 1/2016 |

* cited by examiner

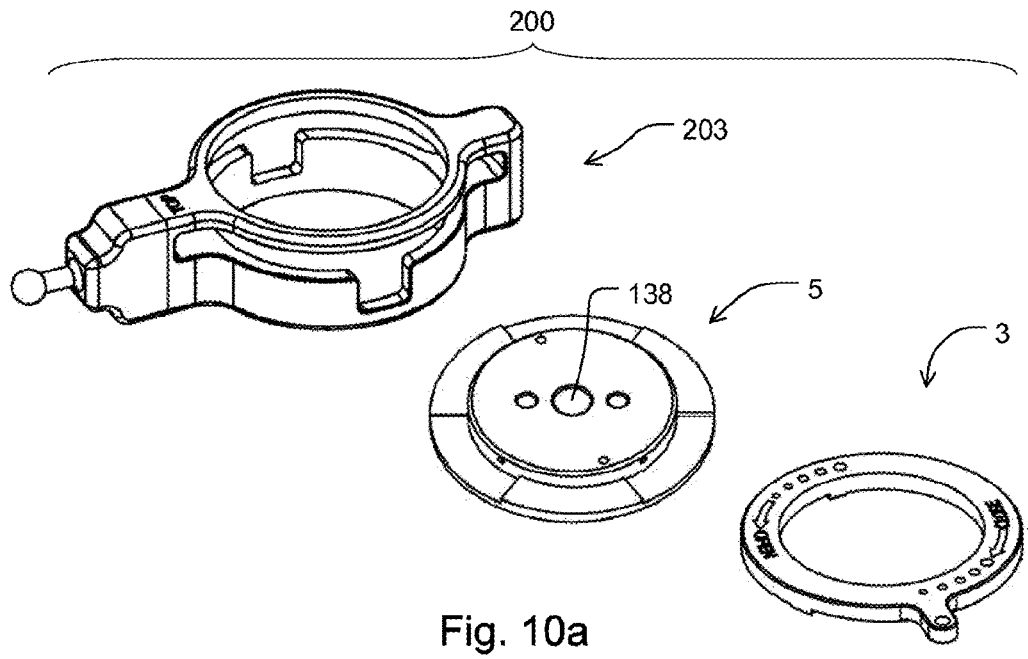
Fig. 10a
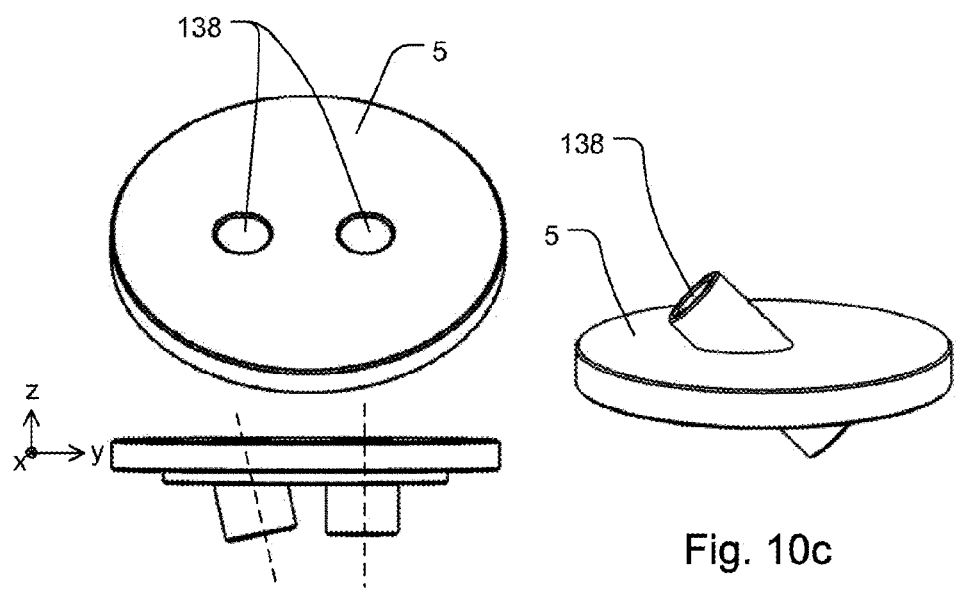
Fig. 10b
Fig. 10c

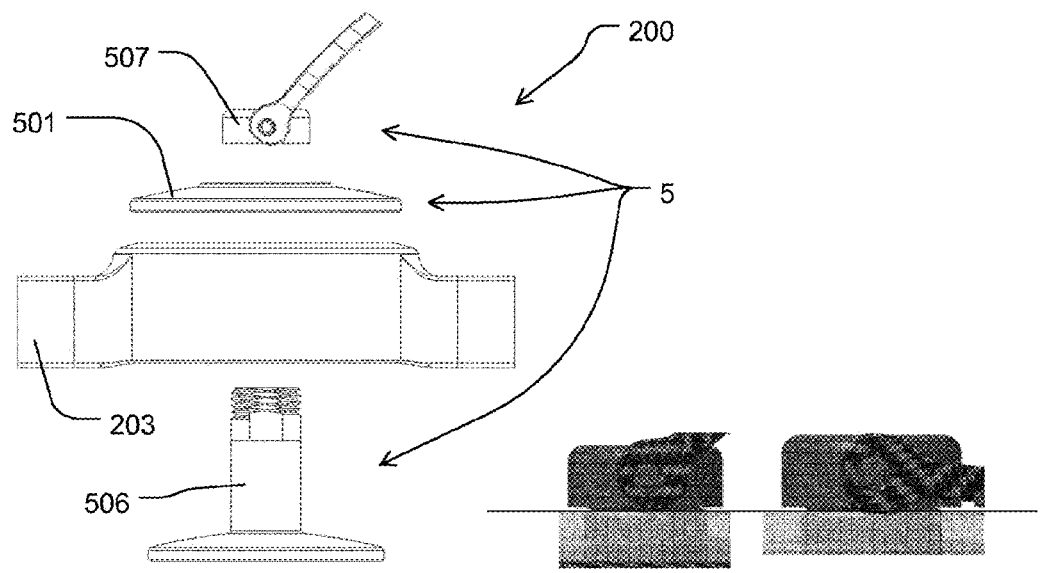
Fig. 14a
Fig. 14b
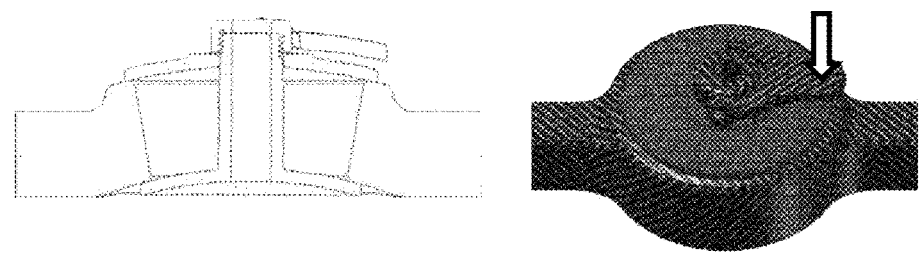
Fig. 14c
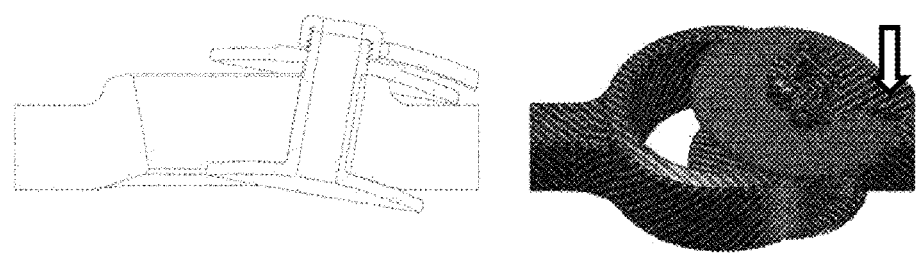
Fig. 14d

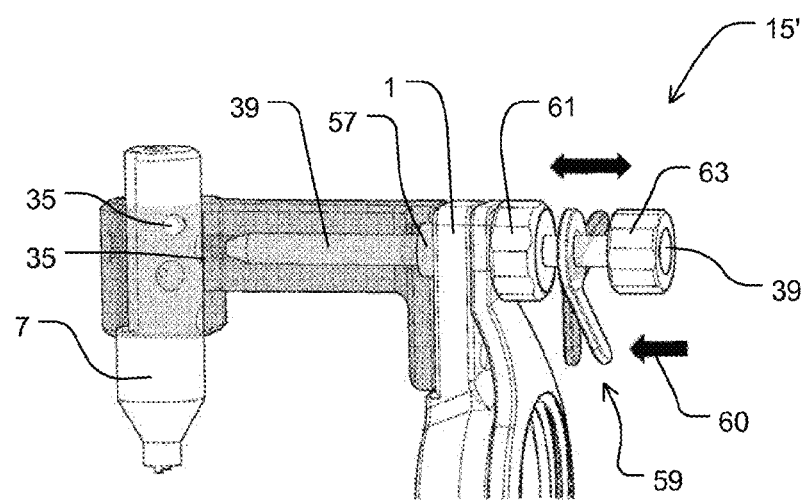
Fig. 31
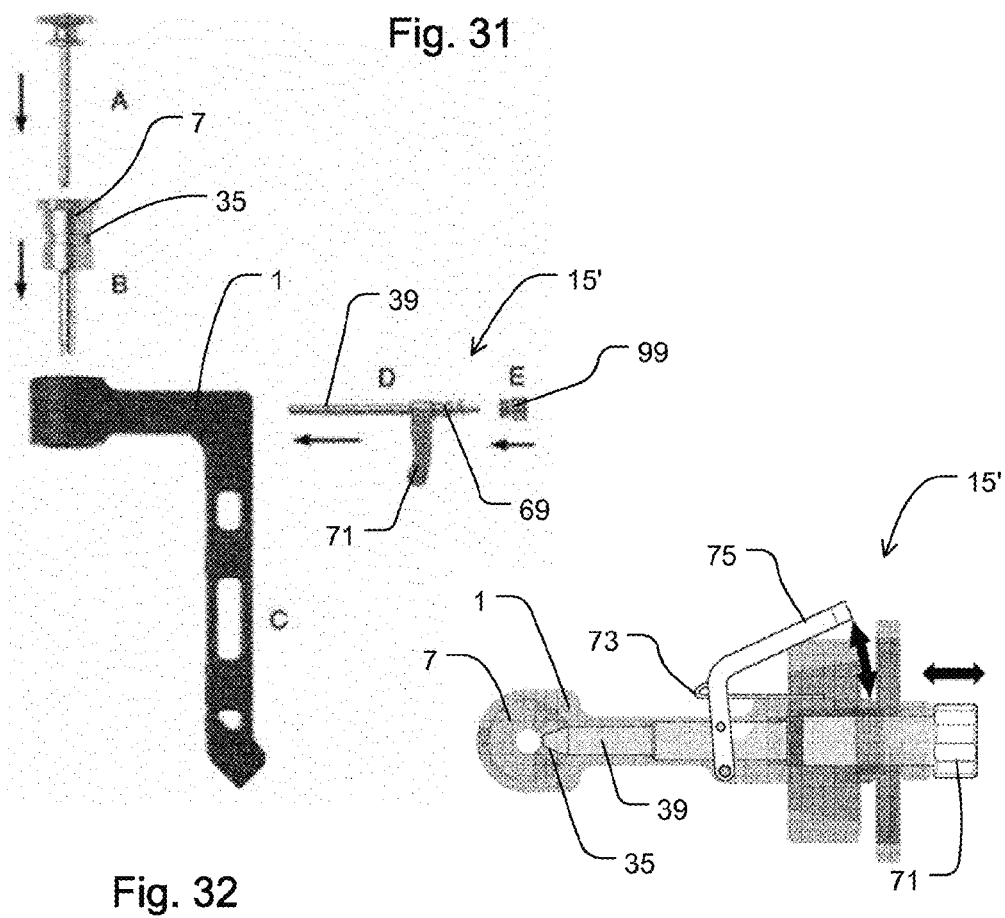
Fig. 32
Fig. 33

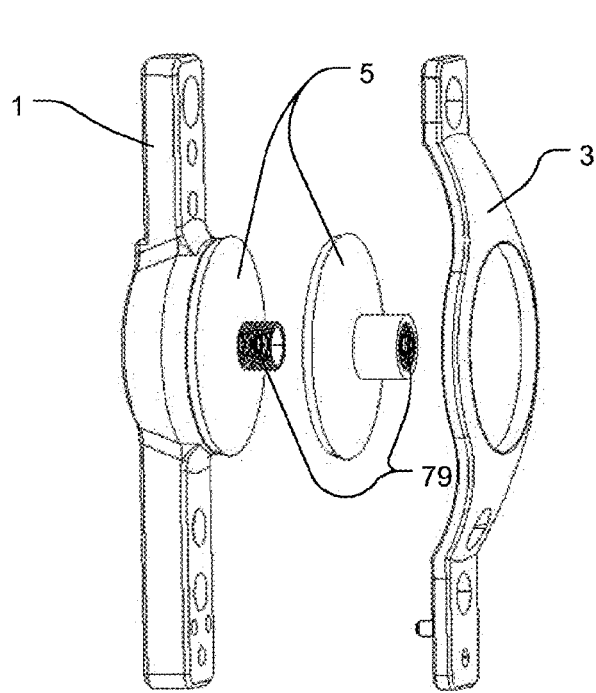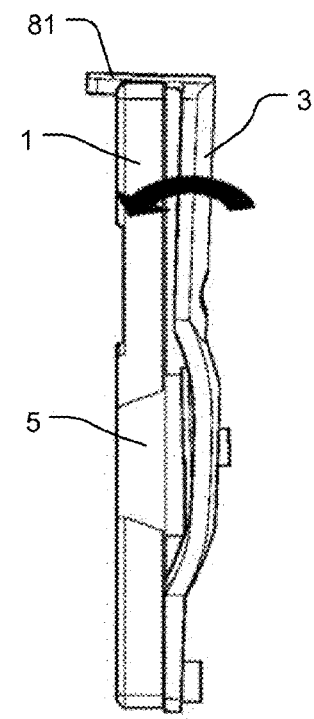
Fig. 36　　　　　　Fig. 37
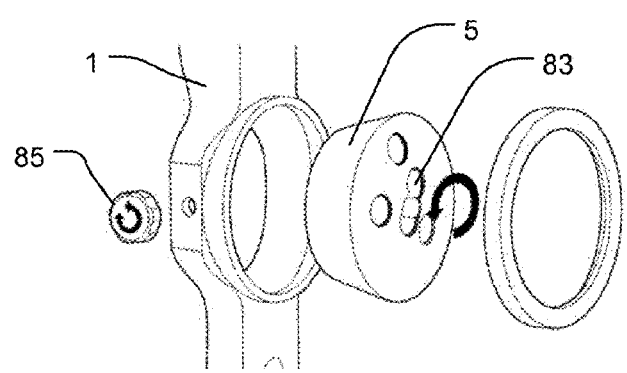
Fig. 38

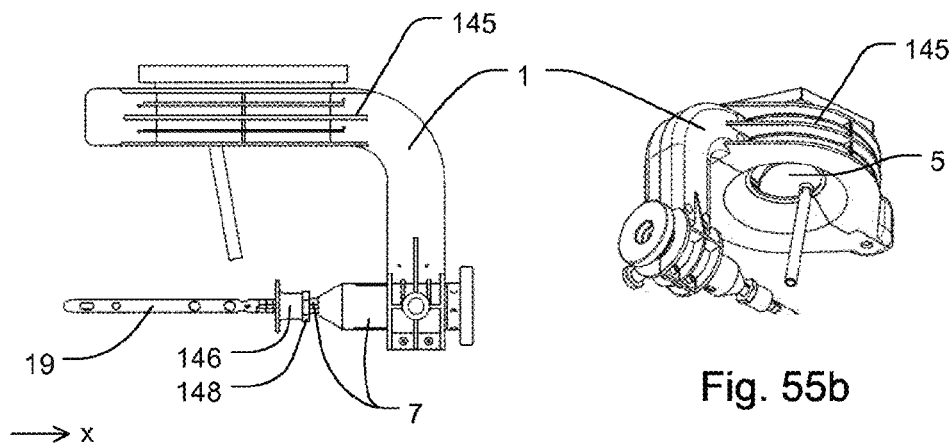
Fig. 55a    Fig. 55b
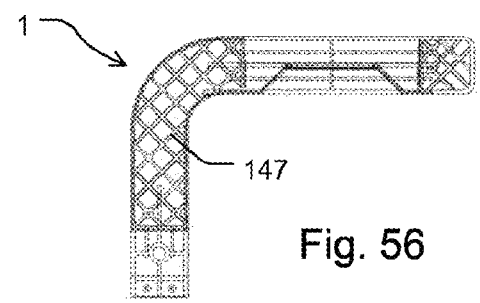
Fig. 56
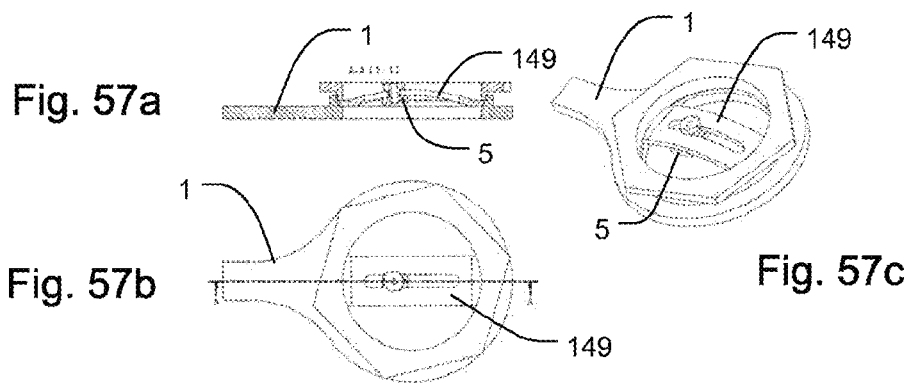
Fig. 57a    Fig. 57c
Fig. 57b
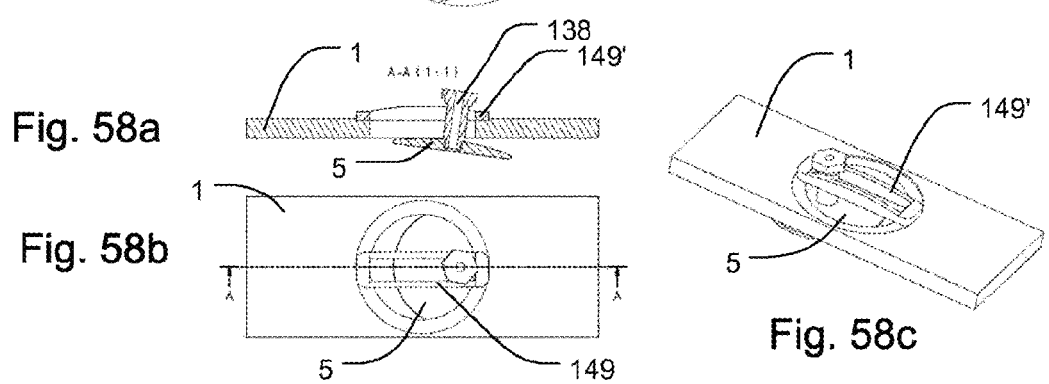
Fig. 58a    Fig. 58c
Fig. 58b

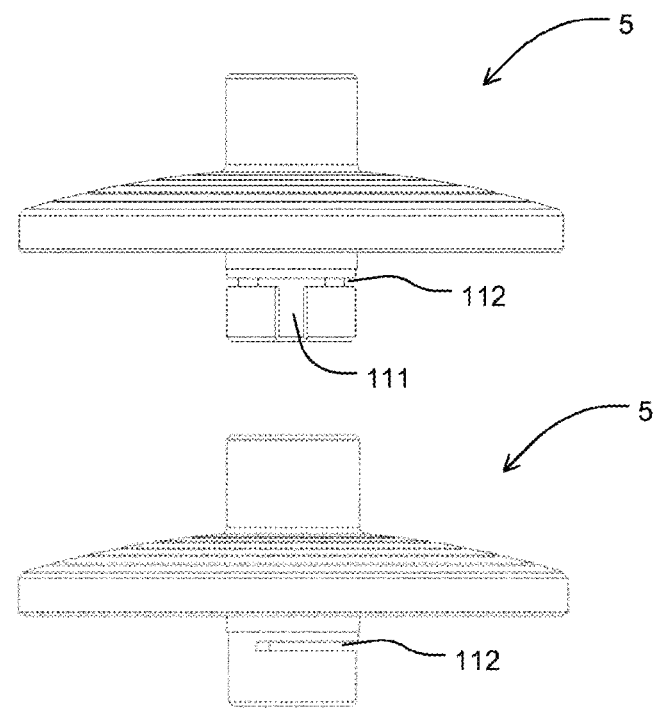
Fig. 59a
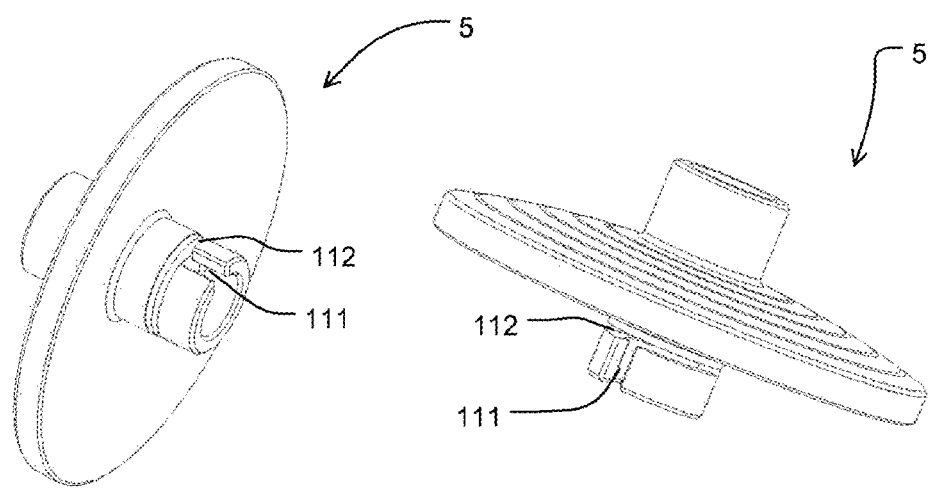
Fig. 59b                    Fig. 59c

POSITIONING-DEVICE MODULE FOR RELEASABLE CONNECTION TO A POSITIONING DEVICE, POSITIONING DEVICE AND SET

The present invention relates to a positioning device module for the releasable connection to a positioning device. The present invention further relates to a set having a positioning device module according to the present invention and a method for aligning a targeting device of the positioning device module according to the present invention. The present invention further relates to a positioning device for fixing an intramedullary nail in long bone as well as a further method for aligning a targeting device.

Intramedullary nails and osteosynthesis plates are known aids for the treatment of fractures, in particular of long bones, but are also used for joint stiffening, arthrodesis. Prostheses are known aids for the replacement of joints. Intramedullary nails and prostheses are inserted into the intramedullary canal of the bone in order to mechanically bridge the bone fractures or to anchor the prosthesis in the bone. Osteosynthesis plates are fixed externally on the long bone and thus may stabilize bone fractures or may be used for arthrodesis. Intramedullary nails may be designed as so-called interlocking intramedullary nails or arthrodesis nails. Interlocking screws serve to secure the connection between bone and interlocking intramedullary nail or arthrodesis nail against relative movement and/or rotation. Cortex screws, in turn, may be used to fix osteosynthesis plates.

The exact placement or positioning of the interlocking screws or cortex screws in intramedullary nails, prostheses and osteosynthesis plates requires a great deal of experience by the surgeon. In the case of long intramedullary nails and prostheses, for example with revision prostheses with distal through-openings for screwing, a deformation or also a torsion of the regions of the intramedullary nails and prostheses to be screwed may aggravatingly occur within the long bone due to anatomical forms of the bone structures. In the case of fracture treatment or arthrodesis with osteosynthesis plates, the anatomical outer contour of the bone may lead to deformations of the plates. This may cause inaccurate drilling, insufficient alignment of the bores with or to the through-holes of the intramedullary nails, prostheses or osteosynthesis plates as well as prolonged operation times.

The object of the present invention is to provide a positioning device module for positioning and/or fixing an intramedullary nail in a long bone, for fixing an osteosynthesis plate on a long bone and/or for fixing a prosthesis in a long bone or for supporting thereby, respectively. It is also an object of the present invention to provide a positioning device for fixing an intramedullary nail in a long bone, for fixing an osteosynthesis plate on a long bone and/or for fixing a prosthesis in a long bone, or for supporting thereby respectively, and to provide a method for aligning a targeting device.

The object of the present invention is achieved with a positioning device module having the features. The object of the present invention is further achieved by a set, a method for aligning a targeting device of the positioning device module, a positioning device for fixing an intramedullary nail in long bone and a further method for aligning a targeting device.

In the following, the terms interlocking intramedullary nail and intramedullary nail are used synonymously. This also applies to arthrodesis nails or extension intramedullary nails and other forms of implants like plates etc.

The positioning device module according to the present invention comprises at least one targeting device for receiving an interlocking device or an instrument for acting on the interlocking device.

The module further comprises at least one receiving section for receiving the targeting device.

It further comprises a section and/or a correspondingly designed device for, preferably releasably, connecting the positioning device module to a positioning device.

The positioning device module according to the present invention further comprises optionally at least one joint. The joint or the deformable section comprises at least one rotary axis.

The joint may serve for rotating the positioning device module or sections thereof, e.g. for rotating the positioning device module relative to the positioning device after being connected thereto, or for rotating the sections of the positioning device module relative to each other, or for rotating the positioning device module or sections thereof in space.

The section for the preferably releasable connection may optionally comprise, or be, the joint or the deformable section.

The set according to the present invention comprises a positioning device module according to the present invention and an extension device for connecting the positioning device module to a positioning device.

The method according to the present invention is provided and designed for aligning a targeting device of a positioning device module according to the present invention, wherein the module optionally comprises a joint or a deformable section of an adjusting device for receiving the targeting device.

The method encompasses preferably aligning or moving the targeting device in the receiving section, optionally fixing the targeting device in the receiving section, aligning the positioning device module, optionally in a way that one or several openings, through-opening or inlets of the targeting device are flush with openings, through-openings or inlets in a connected intramedullary nail, a connected osteosynthesis plate or a connected prosthesis (short: implant) and fixing the positioning device module by the fixing device.

The positioning device according to the present invention comprises a guiding bow with an adjusting device. The adjusting device comprises at least one targeting device. The targeting device is designed to receive, in particular releasably, an interlocking device, e.g. an interlocking screw, or an instrument for acting on the interlocking device, e.g. a screwdriver, a drill or a transfixion wire (wire for the traction-fixing of the bone fragments or implants).

The guiding bow comprises a sleeve guide, which in turn comprises a sleeve. The sleeve is arranged to be rotatable and/or movable relative to the sleeve receptacle. For this purpose, the sleeve receptacle comprises, e.g., a continuous longitudinal opening or a tubular section (herein, both terms are used synonymously).

The sleeve comprises also a continuous longitudinal opening or a tubular section, in which a guiding device may be, or is, arranged.

The method according to the present invention is provided and designed for aligning the targeting device with regard to at least one through-opening of the intramedullary nail by using the positioning device according to the present invention. Said aligning is achieved by flushing one through-opening of the targeting device for inserting the instrument with the at least one through-opening of the intramedullary nail. Said flushing is monitored or assisted particularly by an imaging device.

Embodiments according to the present invention may comprise one or several of the features mentioned above or in the following. In this, the features mentioned herein may, in any combination, be subject-matter of embodiments according to the present invention, unless the person skilled in the art recognizes a specific combination as technically impossible. Furthermore, embodiments according to the present invention are subject-matter of the dependent claims and embodiments.

The information "top" and "bottom" are herein to be understood in case of doubt by the person skilled in the art as absolute or relative spatial information, which refer to the alignment of the respective component when used as intended.

In all of the aforementioned or following embodiments, the use of the expression "may be" or "may have" and so on is to be understood synonymously with "preferably is" or "preferably has" and so on, and is intended to illustrate embodiments according to the present invention.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" as encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Advantageous developments of the present invention are each subject-matter of the dependent claims and embodiments.

The positioning device according to the present invention may comprise at least one positioning device module or sections thereof or may be connected thereto. In this, a targeting device encompassed by this combination may be optionally part of the positioning device and/or of the positioning device module.

Thus, the present invention encompasses also a set with a positioning device according to the present invention and at least one positioning device module according to the present invention or sections thereof.

A positioning device may in several embodiments according to the present invention be a targeting device or a targeting instrument for positioning and/or fixing interlocking devices of an intramedullary nail or other implants in a long bone.

A joystick is presently to be understood as part of a targeting device module which may be moved relative to other parts of a positioning module in one mode and fixed in another. Moreover, the term joystick is not to be understood in a limited way such that a joystick only comprises a "stick" of an elongated shape. On the contrary, a joystick may comprise arbitrary shapes as long as the above condition is met or satisfied.

A joystick frame is part of or identical to the receiving section. The joystick frame contacts the joystick when using the positioning device module. The joystick frame may assume any form as long as said condition is met and it needs not necessarily to assume the form of a frame.

Purely exemplarily, the positioning device may be designed as described in the application entitled "Positioniervorrichtung zum Fixieren eines Marknagels in einem Röhrenknochen and Verfahren" (Positioning device for fixing an intramedullary nail in a long bone and method), which has been filed at the German Patent and Trademark Office on Jan. 20, 2016 with the official file ref. 10 2016 100 953.9 on behalf of the present applicant, the relevant disclosure of which hereby is incorporated by reference is also made in its entirety the subject-matter of the present application.

A positioning device may be designed and prepared for positioning and/or fixing an intramedullary nail or another implant in or on a long bone.

A positioning device may comprise a device for releasably fastening an intramedullary nail or another implant to the positioning device.

A positioning device may comprise a targeting bracket or yoke.

A positioning device may comprise a guiding bow with an adjusting device and/or a targeting device. The targeting device may be designed to receive an interlocking device or an instrument for acting on the interlocking device. The targeting device may be referred to as targeting device, targeting bracket or targeting unit for positioning, inserting and fixing interlocking devices or osteosynthetic fastening elements in an intramedullary nail or in another implant. A positioning device may be a device for releasably connecting an intramedullary nail or another implant mentioned herein, and in particular the head portion thereof, to the positioning device.

In several embodiments according to the present invention, the interlocking device is an interlocking screw or an interlocking pin. The present invention is however not to be limited thereto.

In several embodiments according to the present invention, a fixing of an intramedullary nail is to be understood as connecting the intramedullary nail to the surrounding bone by interlocking screws. The intramedullary nail may be fixed by inserting the interlocking screw both in, or next to, the intramedullary nail as well as in the bone.

In several embodiments according to the present invention, the positioning device is prepared and/or designed for inserting, positioning, guiding, aligning, drilling and/or screwing the interlocking device.

A positioning device may be or may have a static targeting bracket.

A positioning device may be a connecting device for the releasable connection to a bone nail, a plate or another implant for inserting them into the bone.

The positioning device module according to the present invention may in several embodiments according to the present invention be a section, a functional unit, a supplement, an extension or the like, respectively of the positioning device. A positioning device module may be connected to the positioning device as an extension by an, particularly releasable, adapter or a connecting section. An adapter or a connecting section may be, or comprise, a joint.

The positioning device module according to the present invention may be in several embodiments according to the present invention advantageously coupled to differently designed positioning devices by the adapter. The different positioning devices may be optionally produced by different manufacturers and/or be provided for different applications or usages. Possible applications may be positioning and/or fixing an intramedullary nail in a long bone. The long bone may be purely exemplary a humerus, a femur, a tibial bone or another long bone. The long bone may be a human bone or an animal bone.

In several embodiments according to the present invention, the positioning device module is prepared and designed for fixing a revision prosthesis by one or several distal screws.

In several embodiments according to the present invention, the instrument for acting on the interlocking device is for example a screwdriver or another tool for fixing the interlocking device.

The receiving section for receiving the targeting device may in several embodiments according to the present invention be a guiding bow section which may be connected to a positioning device being designed as a guiding bow.

In several embodiments according to the present invention, the joint is a ball joint, a pivot joint or another joint. The joint may be rotatable about one, two or three rotation axes of the joint.

A rotation axis may be referred to as rotary axis. A joint having one rotation axis may be referred to as a joint with one rotational degree of freedom, a joint having two rotation axes as a joint with two rotational degrees of freedom and a joint having three rotation axes as a joint with three rotational degrees of freedom.

In several embodiments according to the present invention, the rotary axis is arranged in a main extension plane which is defined by both main extension directions of the positioning device module.

A first main extension direction, hereinafter referred to as the x-direction or x-axis, may be referred to as a longitudinal direction or longitudinal axis and it extends parallel or substantially parallel to a longitudinal axis of the intramedullary nail or the prosthesis during the use of the positioning device module.

The second main extension direction, referred to hereinafter as y-direction or y-axis, extends perpendicular to the x-axis and generate a plane that is not cut by the longitudinal axis of the intramedullary nail or the prosthesis. A perpendicular direction relative to this main extension plane which is referred to as z-direction or z-axis and is aligned orthogonal to the main extension plane extends orthogonally or substantially orthogonally to the longitudinal axis of the intramedullary nail or the prosthesis during use.

A deformable section for connecting the positioning device module according to the present invention to the positioning device may in certain embodiments according to the present invention be a deformable bar or deformable shaft. The deformable section may be plastically deformable or may comprise plastically deformable sections.

The deformable section may comprise a high plasticity.

By the deformable section, the positioning device module may be rotated about one or more rotary axes and brought into a desired position, for example, to fix an intramedullary nail by at least one interlocking screw in along bone. The positioning device module remains in the desired position due to the plastic behavior, in particular without requiring further interlocking or locking of the positioning device module in this desired position.

In several embodiments according to the present invention, the positioning device module does not comprise a spacer unit fixable on the positioning device module with a spacer the supporting surface of which allows a longitudinal movement transversely to the intramedullary nail on the surface of the intramedullary nail, in particular at the distal end of the intramedullary nail.

In several embodiments according to the present invention, the positioning device module comprises a drill bit.

In several embodiments according to the present invention, the positioning device module does not comprise a spacer which measures, determines, touches or senses a surface of the implant, e.g. of the intramedullary nail.

In several embodiments according to the present invention, the drill bit of the positioning device module does not comprise a spacer which indicates its contact to the implant when applying or using current or voltage. This allows an easy design without the need to provide a voltage source.

In several embodiments according to the present invention, the drill bit comprises an adjusting device for adjusting the length of the drill bit or a drill bit rail.

In several embodiments according to the present invention, the drill bit does not comprise a rotation device which would allow a rotation of through-openings of the drill bit against pins, which through-openings are provided for interlocking devices which serve for connecting the drill bit to the targeting device or to another section of the positioning device module.

In several embodiments according to the present invention, the positioning device module according to the present invention comprises an adjusting device for receiving the targeting device. The targeting device is arranged in or at the adjusting device to be positionable relative thereto. The receiving section is in this embodiment designed for receiving both the targeting device and the adjusting device.

The adjusting device may allow adjusting and/or aligning by rotating and/or moving in the receiving section or relative thereto, e.g. in a first position or a first functional state. In particular, a rotation of the targeting device within the main extension plane of the positioning device module may allow a desired positioning. In a second position or a second functional state of the adjusting device, the targeting device may be, or may be fixed, in a desired position. The fixing comprises in particular fixing the targeting device in the adjusting device as well as fixing both the targeting device and the adjusting device in the receiving section. Such a fixing may for example be a frictional clamping or a frictional fixing.

In several embodiments according to the present invention, the positioning device module comprises a fixing device for releasably blocking the joint. Using the joint, the positioning device module may be rotated or moved and thus positioned relative to the positioning device and in particular relative to an intramedullary nail in a long bone, to an osteosynthesis plate or to a prosthesis. After the positioning is completed, the joint may be fixed and locked by the fixing device. Subsequently, a subsequent alignment by the targeting device may take place. For example, using the joint, a flushed alignment of a through-opening of the intramedullary nail with a through-opening of the targeting device may be achieved or brought about, in particular using an imaging method.

After this alignment is completed and the receiving section of the positioning device module is fixed in the desired and adjusted position or angular position(s) of the joint by the fixing device of the joint, the targeting device may be subsequently aligned. The order given here is optional and may be changed or altered.

The fixing device may for example be a clamping lever, a wing screw, a knurled thumb screw, a hexagon socket screw or an eccentric or may comprise same.

The joint may in several embodiments according to the present invention additionally comprise an elastic element, e.g. a spring element, in order to advantageously facilitate or improve the positioning of the positioning device module by a preload. The required frictional force for moving and rotating the joint may be adjusted by the spring element.

In several embodiments according to the present invention, the joint is or comprises a cylindrical joint, a pivot joint or a combination of any joint types. A cylindrical joint with one rotational freedom degree may be a hinge joint, a rolling joint, a wheel joint or a pivot joint. The pivot joint with two rotational freedom degrees may be a double pivot joint.

A ball joint comprises three rotational freedom degrees and may thus be rotated about three mutually perpendicular axes. This advantageously allows, e.g., an alignment of the positioning device module on, e.g. distal, through-openings in the intramedullary nail or prosthesis, even when these, e.g. due to inserting the intramedullary nail or prosthesis in the long bone, were deformed three-dimensionally. A three-dimensional deformation may be e.g. an undesired bending of the, in particular distal, end region of an intramedullary nail with simultaneous torsion of the intramedullary nail about its longitudinal axis. Such a deformation may occur depending on the anatomical contours within the long bone, in particular in the case of long intramedullary nails or prostheses (e.g. in case of revision prostheses). Tracking a through-opening in the targeting device in the main extension plane of the positioning device module (for aligning to a distal through-opening in intramedullary nails or the prostheses) may be achieved by rotating the targeting device in the receiving section and/or rotating the targeting device in the adjusting device. Alternatively or additionally, this may be achieved by an oblique or inclined (not less than 90°) arrangement of one or several through-openings in the targeting device relative to the main extension plane of the positioning device module.

In several embodiments according to the present invention of the positioning device module, the joint comprises more or less than two rotational freedom degrees.

In certain embodiments according to the present invention of the positioning device module, the deformable section is, or comprises, a plastic deformable metal and/or a plastic deformable composite material. A metal may be a metal alloy. A metal may be plastically deformed by cold deformation or cold working.

In several embodiments according to the present invention, the targeting device is arranged to be rotatable and/or translationally movable in the adjusting device and/or in the receiving section.

In several embodiments according to the present invention, the positioning device module according to the present invention comprises a force-fit and/or form-fit fixing mechanism for locking or fixing the targeting device in the adjusting device.

A force-fit fixing mechanism is e.g. a frictional fixing mechanism, which may be designed purely exemplarily by a thread or an eccentric. Furthermore, a frictional fixing mechanism may be achieved by elastic elements, e.g. by spiral springs and/or by a threaded lever.

In several embodiments according to the present invention, the positioning device module comprises a positioning aid for aligning the positioning device module. A positioning aid may advantageously support or improve a manual guiding of the positioning device module. The positioning aid may be advantageously connected or connectable to other sections of the positioning device module, e.g. the receiving section, in a releasable manner.

The positioning aid may in particular allow guiding the positioning device module within a beam path of an imaging device, without requiring the operator holding the adjusting fork to hold his hand in the X-ray beam. The positioning aid may thus advantageously help reduce a possible radiation burden caused by an imaging device, designed purely exemplarily as an X-ray C-arm to a guiding hand.

For example, the positioning aid may be a lever or an adjusting fork which is releasably inserted in a through-opening of the targeting device.

In certain embodiments according to the present invention, the targeting device comprises at least one, two or more recesses, protrusions, depressions or through-openings. They are intended for receiving at least one interlocking device or one instrument for acting on the interlocking device.

In several embodiments according to the present invention, the positioning device module according to the present invention comprises a drill bit for receiving at least one interlocking device or one instrument for acting on the interlocking device. Since this interlocking device or this instrument is not the interlocking device or the instrument which is inserted through through-openings of the targeting device, one may refer to them as further interlocking devices or instruments.

In several embodiments according to the present invention, the longitudinal axis of the further interlocking device or the longitudinal axis of the instrument for acting on the further interlocking device, each received in the drill bit, is aligned in an angle between 80 and 100 degrees relative to the longitudinal axis of the first interlocking device or relative to the longitudinal axis of the instrument for acting on the first interlocking device of the targeting device or the through-openings provided thereto. In other words, one or several interlocking screws may be screwed in at an angle rotated by 90 degrees about the longitudinal axis of the intramedullary nail, and thus the intramedullary nail may advantageously be additionally fixed in the long bone. Depending on the design of the drill bit, the additional interlocking screws may be screwed in at angles other than 90 degrees. In particular with multiple fractures of long bones, a multiple securing of the intramedullary nail from different directions or a crossing may advantageously improve the healing process.

In several embodiments according to the present invention, the drill bit is connected or connectable to the targeting device, in particular releasably, in particular centered or rotation-proof. The drill bit may for example be inserted and positioned in the through-openings of the targeting device. The connection between the drill bit and the targeting device is in particular releasable. The connection may be or may comprise a securing against an unintentional release. The connection may be force-fit and/or form-fit.

In several embodiments according to the present invention, the drill bit comprises at least one drill bit rail changeable in length or movable longitudinally for positioning the interlocking device.

In several embodiments according to the present invention, the positioning device module is connected, in particular releasably, to a positioning device.

In several embodiments according to the present invention, the set according to the present invention comprises an adapter for connecting the extension device to the positioning device, wherein the position of the positioning device module connected to the extension device is changeable. Using the adapter, the alignment of the targeting device or the interlocking device connected to the targeting device or of the instrument for acting on the interlocking device to the position of the through-openings or bores of the intramedullary nail, the osteosynthesis plate and/or the prosthesis may be adapted or flushed therewith.

In several embodiments according to the present invention, at least one through-opening of the targeting device is aligned perpendicular to the longitudinal axis of the intramedullary nail and/or of the long bone and/or at least one through-opening is aligned obliquely to the longitudinal axis of the intramedullary nail. The through-opening aligned obliquely to the longitudinal axis of the intramedullary nail may be at an angle between 50 and 80 degrees relative to the longitudinal axis of the intramedullary nail and/or of the long bone. Benefits associated therewith may include: i) avoiding soft tissue structures (tendons, nerves); ii) easier access; iii) two converging screws may intersect to create greater biomechanical stability; iv) screwing/interlocking from different (several) planes leads to an increased biomechanical stability.

In several embodiments according to the present invention, the set according to the present invention comprises an intramedullary nail or another implant which, e.g. distal, through-openings serve for inserting interlocking devices for fixing the implant with or to the bone. These through-openings of the intramedullary nail or implant are aligned and positioned such that the through-openings of the targeting device of the positioning device module, flush with the through-openings of the implant, in particular after the alignment of the targeting device, of the adjusting device and/or of the drill bit.

The implant and the positioning device module (with or without drill bit) are preferably matched to each other with regard to their through-openings through which tools or interlocking devices are each guided during use, for example with regard to orientation or angle of the longitudinal axis of the implant.

The method according to the present invention encompasses in several embodiments according to the present invention inserting or receiving the interlocking device, or the instrument for acting on the interlocking device, in the targeting device. Furthermore, the method according to the present invention may encompass fixing the intramedullary nail, or the osteosynthesis plate or the prosthesis by at least one interlocking device. In several embodiments according to the present invention, the method does not encompass same.

The method according to the present invention encompasses in several embodiments according to the present invention determining a distance between a through-opening of the intramedullary nail and the positioning device module; arranging a drill bit in or at the positioning device module, preferably in a through-opening of the positioning device module; and adjusting the drill bit considering the distance between the through-opening of the intramedullary nail and the positioning device module.

The method according to the present invention encompasses in several embodiments according to the present invention the use of a C-bow or of another X-ray source.

In some embodiments according to the present invention, the guiding device is preferably arranged in the sleeve to be displaceable and/or rotatable relative thereto.

In certain embodiments according to the present invention, the guiding bow is arranged to be displaceable along the longitudinal axis of the sleeve relative thereto and to be rotatable about the longitudinal axis of the sleeve relative thereto.

In some embodiments according to the present invention, the guiding device comprises a connection section for releasable connecting the sleeve to an intramedullary nail.

In some embodiments according to the present invention, fixing the intramedullary nail is to be understood as connecting the intramedullary nail with or using interlocking screws. The intramedullary nail is fixed in the bone by inserting the interlocking screws. The positioning device according to the present invention thus serves for fixing. It serves also for fixing or may be respectively used for this reason in some particular embodiments.

The guiding bow having an adjusting device, which comprises a targeting device, may in some embodiments according to the present invention be referred to as a targeting bracket. The targeting bracket is preferably arched, at least in sections thereof.

In some embodiments according to the present invention, the interlocking device is an interlocking screw or an interlocking pin. However, the present invention is not limited thereto.

In some embodiments according to the present invention, the receiving device provided for receiving an interlocking screw in the intramedullary nail is a device with at least one prefabricated through-opening for the interlocking screw. The receiving device may be sleeve-shaped or cylindrical. The receiving device may be composed of several parts and/or several materials (composite). For example, a plastic ring may be used as part of the receiving device. The plastic ring may advantageously prevent an unintentional unscrewing of the interlocking screw.

In specific embodiments according to the present invention, the receiving device is an opening or a bore in the intramedullary nail.

In certain embodiments according to the present invention, the targeting device is prepared and/or designed for setting, positioning, guiding, aligning, drilling and/or screwing the interlocking device.

In some embodiments according to the present invention, the guiding device is to be understood as a hollow or tubular or preferably longitudinally extended device with a longitudinal through-opening through which a tool may be led. Appropriately, the guiding device could be denoted as bracing device or intramedullary-nail-receiving device in several embodiments according to the present invention.

In some embodiments according to the present invention, the guiding device is a tubular, internally-hollow rod or a hollow tube. The guiding device may be provided and prepared for the manual, releasable fixing, securing or fastening of the intramedullary nail at or in the sleeve. In particular, the guiding device may have a handle, a knob or a similar arrangement at one axial end thereof for manually rotating the guiding device about its longitudinal axis, for example, when screwing the guiding device in the intramedullary nail. The handle or knob may, for example, be knurled.

The opposite end of the guiding device can carry a thread, preferably an external thread, or an external thread section. The external thread may be matched to be connected to an internal thread or an internal thread section at an axial end of the intramedullary nail.

In specific embodiments according to the present invention, the guiding device is provided and prepared for guiding a tool through it for the force-fit locking of the receiving device and of the interlocking device guided in the receiving device. A force-fit locking can be achieved e.g., by screwing a threaded pin which acts in the intramedullary nail on the receiving device.

In some embodiments according to the present invention, the guiding device is designed to releasably interlock the intramedullary nail against the sleeve.

In specific embodiments according to the present invention, the guiding device is arranged coaxially to the longitudinal axis of the sleeve.

In some embodiments according to the present invention, the sleeve, in particular on an outer or circumferential surface thereof, comprises a sliding guide along which the guiding bow or a section thereof may be moved along the sleeve or relative to the sleeve.

In some embodiments according to the present invention, the term "sliding guide", as used herein, describes a slot, web, recess or groove, each referred to as a slide, in or on or along which a device, in particular the guiding bow, is guided or force-guided.

Using the slide, the movement of the guiding bow relative to the sleeve is predetermined or defined in some embodiments according to the present invention. The transfer function of the sliding guide is determined and specified by the course of the slot, the web, the recess or the groove.

The sliding guide preferably serves, in particular, for controlling or aligning the targeting device and the interlocking device received therein, in particular the interlocking screw, towards the prefabricated through-openings of the intramedullary nail for the interlocking screw.

The sliding guide can generate a combined displacement movement (in the direction of the longitudinal axis of the sleeve) and/or rotary movement (in the circumferential direction of the sleeve).

Furthermore, the sliding guide may specify an initial position and/or an end position of the displacement path.

The sliding guide may be a helical groove.

In certain embodiments according to the present invention, the slide is produced on the sleeve by eroding, chipping or machining shaping process, e.g. by milling or drilling or by laser processing of the sleeve.

In specific embodiments according to the present invention, the sleeve is produced together with the slide by means of an additive (generative) manufacturing method (e.g. by laser sintering).

In some embodiments according to the present invention, the slide is produced by means of an application method (e.g. welding).

In some embodiments according to the present invention, the sleeve comprises at least one snap-in position provided on or in the sleeve.

The snap-in position may serve to releasably secure or lock the guiding bow in at least one predetermined position on the sleeve or relative thereto.

The snap-in position is preferably not integrated into the sliding guide, but is located separately from the latter, e.g., at least partially, on one side of the sleeve which is opposite to the side with the sliding guide.

The snap-in position may be arranged, for example, in the circumferential direction of the sleeve, on an opposite side of the sleeve rotated by 180 degrees.

The snap-in position may be a recess in the shell surface of the sleeve. It may be a through-opening in the wall of the sleeve.

For example, the guiding bow may be guided along the sliding guide on the one side of the sleeve (viewed in the circumferential direction of the sleeve) by means of a pin, which is integrated or inserted into the guiding bow. On the opposite side of the sleeve, the guiding bow may have a snap-in arrangement which is designed to engage or interact in the snap-in position, preferably to snap-in therein.

The snap-in position may be a form in the slide. It may be a through-hole or opening in the wall of the sleeve.

The snap-in position may be designed in order to allow the guiding bow to be locked at the sleeve by means of clamping, snapping-in or form-fit connection.

The guiding bow may be locked in one of the snap-in positions, for example, by means of a bolt or snap-in pin. Thus, its orientation to the sleeve is releasably fixed.

In some embodiments according to the present invention, the guiding bow comprises at least one snap-in pin or bolt for releasably snapping-in the guiding bow on or in the at least one snap-in position of the sleeve. An arrangement or positioning of the snap-in pin in a snap-in position may be referred to as a snap-in arrangement. If the snap-in pin is not snapped-in, one speaks of a non-snap-in arrangement. The snap-in pin may be arranged to be repeatedly moved between the two aforementioned positions, the snap-in arrangement and the non-snap-in arrangement.

In specific embodiments according to the present invention, the snap-in pin is arranged to be manually snapped-in or positioned and/or to be manually released or decoupled again. For such manual actuation, a gear transmission, a drive, a slider or the like may be provided. The manual actuation may be supported by springs. Alternatively, the snap-in and/or the release or decoupling may be effected without manual actuation, e.g. by means of a spring-supported ball or a similar arrangement.

In some embodiments according to the present invention, the snap-in position has a longitudinal groove which is aligned in the circumferential direction of the sleeve, wherein a longitudinal groove may be an elongated groove, recess or through-opening in the shell surface of the sleeve extending in an arbitrary direction.

The longitudinal groove may allow a displacement of the snap-in pin or bolt, within the limits defined by the geometry, in the circumferential direction of the sleeve and relative thereto after the snapping-in of the snap-in pin into the snap-in position. The permitted displacement of the snap-in pin after the snapping-in may be referred to as a play of the snap-in pin in the snap-in position. The play may be predetermined by the shape of the longitudinal groove, in particular by its length. For example, such play may allow to align, displace or position the interlocking screw, within a through-opening for the interlocking device (e.g. a long hole or a bore) in the intramedullary nail within predetermined (one-side or double-side) limits.

In certain embodiments according to the present invention, the longitudinal groove is designed to move or rotate/pivot the interlocking device or interlocking screw with a play in a defined dimension or circumference, e.g. +/−10° in the circumferential direction of the sleeve, e.g. with respect to the center of the through-opening in the intramedullary nail.

In some embodiments according to the present invention, the guiding bow comprises a locking device, in particular a fixing screw, for preferably manually locking the guiding bow in a predetermined position of the guiding bow relative to the sleeve, by means of the snap-in pin being in a selected snap-in position.

After the locking, the guiding bow cannot be moved relative to the sleeve anymore.

In certain embodiments according to the present invention, the sleeve comprises markings by means of which the current position of the guiding bow relative to the sleeve can be controlled or monitored.

The snap-in position or the slide or the sliding arrangement on or in the sleeve may be concealed when the guiding bow is moved in the sliding guide such that a user of the positioning device according to the present invention does not see the current or instantaneous position of the guiding bow between the snap-in positions or in the slide. However, it may be helpful for the user, for example to recognize in which of the several snap-in positions the snap-in pin of the guiding bow is currently located or situated. This may advantageously facilitate and simplify the further positionings of interlocking screws in the intramedullary nail by the positioning device according to the present invention. Therefore, the sleeve may have an orientation aid for the user, which reproduces or reflects the slide or the sliding guide in a region on the surface of the sleeve being visible for the user. In such embodiments according to the present invention, the slide may be impressed or visualized in mirror image on the sleeve in this visible region, e.g. by engraving.

In specific embodiments according to the present invention, the guiding device, for releasably connecting the sleeve to the intramedullary nail, is arranged inside the sleeve and preferably coaxially or parallel to the longitudinal axis of the sleeve.

In order to be able to use the positioning device according to the present invention for fixing the intramedullary nail, it is intended to connect the positioning device to the intramedullary nail to be fixed. The connecting arrangement provided for this purpose comprises particularly a first and a second component.

The first component may be a web-groove connection for the twist-proof of mutual arrangement of sleeve and intramedullary nail. For example, the sleeve comprises, at an axial end, at least one, but preferably two, three or more (for example axial) webs, protrusions, pins or steps which engage in a corresponding number of (for example axial) grooves, slots or recesses at an axial end of the intramedullary nail in a form-fit manner. Alternatively, the intramedullary nail may have the steps or the like and the sleeve may have the grooves or the like. Combinations thereof are possible.

After the sleeve and the intramedullary nail are arranged to each other so as to be twist-poof and preferably also in a predetermined manner, the sleeve and the intramedullary nail can be releasably connected by a second component. This second component may be realized by means of the guiding device. For this, the guiding device may be arranged inside the sleeve and coaxially with the longitudinal axis of the sleeve. The guiding device may be inserted through the sleeve and screwed together by an external thread or external thread section arranged at the axial end of the guiding device to an internal thread or internal thread section of the intramedullary nail. The guiding device thus releasably braces the intramedullary nail against the sleeve and hence holds it connected to the guiding bow, preferably in a predetermined orientation with respect to the latter.

Using the two components described above, it may advantageously be achieved that the intramedullary nail does not rotate or co-rotate in the direction of the screw rotation while it is being screwed to the guiding device or while the screwing is released, for example after fixing the intramedullary nail by the interlocking screw(s). Avoiding a turning or a rotation, even though only slightly, e.g. in the range of only few degrees, may be advantageous and important for the later stability of the long bone.

In some embodiments according to the present invention, the guiding device is tubular or hollow inside and thus designed for guiding or guiding through a tool. The tool may, e.g., be used for actuating or screwing (tightening and releasing) a locking or blocking device or a compression device in the interior of the intramedullary nail. The locking or blocking device may be designed as a clamping screw for fixing or clamping an adjustable receiving device for an interlocking screw.

For example, the tool for screwing or clamping may comprise an internal threaded pin in the intramedullary nail. The tool may be an Allen wrench. The tool may, for example, be configured to apply a torque of, e.g., approximately 5 Nm, 7 Nm or 9 Nm or range between 5 to 9 Nm.

In certain embodiments according to the present invention, the adjusting device is displaceable, in a limited or unlimited manner, along the guiding bow together with the targeting device, which is to be aligned on the intramedullary nail. The displacement direction along the guiding bow is defined as the x-direction. The targeting device is designed to receive an interlocking device, in particular an interlocking screw, or an instrument for acting on the interlocking device. Thus, with the aid of the positioning device according to the present invention, the interlocking device may be aligned and positioned, in a superimposed movement along the guiding bow in the x-direction and corresponding to the position of the guiding bow relative to the intramedullary nail corresponding to the sliding guide on the sleeve, in order to subsequently fix the interlocking screw in the intramedullary nail or in order to guide the interlocking screw through the intramedullary nail and to subsequently fix it in the bone.

In some embodiments according to the present invention, the guiding bow is designed, at least in sections, as a circular bow or in a circular bow shape. The adjusting device is thereby, at least in sections, displaceable along a circular bow.

In specific embodiments according to the present invention, the targeting device comprises one or more openings which face the intramedullary nail and reach through or pass through the adjusting device. The opening(s) is/are designed in particular for receiving an interlocking device or an instrument for acting on the interlocking device positioned in a receiving device of the intramedullary nail.

In specific embodiments according to the present invention, the guiding bow comprises stops for limiting the displacement path of the adjusting device along the circular bow. The stops may advantageously improve the handling of the positioning device according to the present invention, e.g., in that the adjusting device may be aligned faster or easier to a desired, selected or targeted through-opening in the intramedullary nail. The stops may also be provided with regard to anatomically more useful or reasonable positionings of the interlocking devices.

In some embodiments according to the present invention, the targeting device is movably arranged in the circumferential direction of the sleeve in the longitudinal direction of the guiding bow (x-direction) and perpendicular to the longitudinal direction of the guiding bow (y-direction). Through this displaceability in both the x-direction and the y-direction, an instrument in the targeting device, which may be connected to a locking device, may be moved and positioned within a circular section. The circular surface of this circular section may be stretched by the x-direction and the y-direction. The targeting device may be arranged perpendicular to this circular surface. The center of the circle lies in particular in the receiving device for the interlocking screw in the intramedullary nail, here in particular at the intersection of the receiving device of the interlocking screw and longitudinal axis of the intramedullary nail (or the longitudinal axis of the sleeve). Intramedullary nail and positioning device may be adjusted to each other accordingly. The movement of the instrument on the circular surface and it positioning may be compared with the movement and operation of a joystick.

In certain embodiments according to the present invention, the targeting device is arranged to be displaceable in the adjusting device and relative thereto or to the guiding bow.

In some embodiments according to the present invention, the adjusting device is arranged to be movable in at least a first position, here referred to as the adjustment position, for moving the targeting device relative to the adjusting device or to the guiding bow. In at least a second position, here referred to as a fixed position, the adjusting device for fixing the targeting device is not movable relative to the adjusting device or to the guiding bow, which may in particular be effected by frictional connection.

The fixing of the targeting device relative to the adjusting device or relative to the guiding bow is preferably releasable.

The first position is provided, in particular, for positioning and aligning the interlocking screw with the desired receiving device in the intramedullary nail. After the alignment is completed and the interlocking screw should subsequently be fixed in the receiving device or through the latter in the long bone, the targeting device is fixed relative to the adjusting device (second position). In this position, the targeting device and in particular the adjusting device can no longer be displaced or moved relative to the guiding bow. Subsequently, using an instrument which is connected to an interlocking screw and which is arranged in the targeting device, the interlocking screw can advantageously be simply and securely fixed in the desired position in the intramedullary nail and in the long bone.

The positioning and/or fixing of the targeting device relative to the adjusting device may take place in different ways. The various embodiments are based, in particular, on a 3-shell model or a 3-shell arrangement. The radial inner shell may be a section of the guiding bow. The radial outer shell may be the adjustment device or a section thereof. In the middle shell between the inner shell and the outer shell, in particular the targeting device is integrated. The middle shell is movable and/or positionable between the outer and the inner shell. The fixing of the middle shell, after the positioning and alignment of the targeting device has been completed, may be carried out in different ways. Examples of this fixing are described below.

A first concept for fixing the middle shell is referred to herein as spring pin concept. One or more spring pins, which are integrated, for example, into the outer shell press with their spring force directly or indirectly onto the middle shell. With these pressing forces, the middle shell is pressed onto or against the inner shell and fixed in contact therewith by frictional force. The pressing forces can be varied on the basis of the number and/the spring strength of the spring pins so that, on the one hand, the targeting device remains movable, on the other hand, the frictional forces are high enough to allow exact screwing of the interlocking screw when the positioning and alignment are completed.

A second concept is referred to here as a flap concept. The outer shell is hinged on one side. A device for fixing or clamping the outer shell with the inner shell is arranged on a position (on the upper side of the shell) opposite to the hinged mounting. For example, the outer shell may be fixed and clamped on or against the middle and inner shell by means of a wing screw, an eccentric, a snap hook or the like. When this device fixes the outer shell to the inner shell, for example by manually tightening a wing screw, the middle shell in which the targeting device is arranged is clamped and immovable. If, on the other hand, this device is released, the middle shell may be moved and thus the targeting device may be positioned and aligned.

A third concept is referred to here as a spring concept. The middle shell comprises two shells radially arranged above each other. The two shells arranged above each other are radially pushed apart by springs arranged between these two shells. Furthermore, at least one of the two shells may comprise surface structures, for example protrusions, which may engage in further surface structures on the radial inner side of the outer opposite shell. The surface structures on the inner side of the outer shell may, for example, be bores into which the protrusions engage or snap-in.

A fourth concept is referred to as a thread-concept. The middle shell comprises two separately-produced shells, being arranged radially above each other, which are connected to each other by a thread. Due to the rotation of one of the two shells relative to the second shell, the shells are, depending on the direction of rotation, either turned together or turned apart, i.e., their distance to each other is reduced or increased. If these two shells are turned apart, the inner and outer shells are spun and thus fixed.

A fifth concept uses a lever action to clamp the outer shell against the middle shell or to release a tension. In the basic state, the outer shell presses, in the spun state, against the middle shell, which in this basic state is fixed or immovable. When the outer shell is pressed radially outwards by or is bent outward by a lever effect, the middle shell loosens. The targeting device may be aligned and positioned until the outer shell is returned to the basic state and the middle shell is fixed. The lever effect is applied, in particular using manual force.

In certain embodiments according to the present invention, the guiding bow is made as multiple-piece. A first section of the guiding bow is connected to the sleeve guide, a second section of the guiding bow is connected to the targeting device. At least one further section is arranged between the first section and the second section. Said further section comprises a guiding device for moving the second section relative to the first section in x-direction and/or in y-direction.

Some or all embodiments according to the present invention may comprise one, several or all of the previous and/or the following advantages.

Using the positioning device module according to the present invention, it is advantageously possible to correct, during an operation, minor misalignments when positioning and/or when screwing (the so-called "setting") interlocking screws into an intramedullary nail or prosthesis arranged in the long bone or on an osteosynthesis plate arranged on the long bone.

In particular, long intramedullary nails or revision prostheses may deform in long bones like e.g. in the humerus, femur, tibia or in another long bone due to anatomical conditions. For example, the distal end regions of an intramedullary nail or of a revision prosthesis may bend by a few degrees, e.g. 3 degrees, 5 degrees or 10 degrees with regard to the longitudinal axis of the implant (intramedullary nail, revision prosthesis) or may twist about the longitudinal axis. This bending or torsion is not visible and recognizable from the outside (outside of the long bone). Although the deformation may be made visible for example by an imaging process or procedures. However, when fixing the implant by screws, for example by cortex screws, it is important to make an exact bore into the bone with the most accurate alignment possible of the drilling direction on the through-opening in the implant in order to accurately set the screws (interlocking screws). A slight deviation would delay the entire fixing process at least in time during an operation and could potentially cause i) the drill to break; ii) the screws not to be set; iii) an increased abrasion.

This oblique screwing may further adversely affect the stability and healing process of a fracture of the long bone. The positioning device module according to the present invention may advantageously at least minimize or even prevent such oblique screwing.

Using the positioning device module according to the present invention, the location and position of a deformed implant (intramedullary nail, revision prosthesis) may be determined in a long bone. Using said determination of location and position, based on a first bore in the long bone using the positioning device module according to the present invention, in particular using a so-called step drill, the axial distance to first bore may be measured by the positioning device module and thus allowing an exact positioning of further interlocking screws, in particular at other angle positions with respect to the first bore, advantageously easily and accurately. These further bores may optionally be made using a so-called drill bit.

The positioning device module according to the present invention may thus also tolerate implantation-induced bending or twisting of the implant. It comprises the devices required for determining the specific location of the through-openings in the body of the patient or in the surrounding, which through-openings are provided for the interlocking devices. The positioning device module according to the present invention may advantageously further comprise the devices which allow, upon detecting the specific location, to introduce the interlocking device into the corresponding through-opening of the implant in a targeted manner and simultaneously without significant complexity or effort.

Determining the specific location of all through-openings of the implant in which the interlocking devices are to be introduced or brought, may be obtained by irradiation in only one beam direction. An irradiation from several directions is not required according to the present invention and advantageously even when the interlocking devices are introduced from several directions. This may advantageously contribute to a reduction of the required radiation exposure. Simultaneously, using for example a metal detector is also advantageously not required.

The locations and angles of the bores for the interlocking screws and the location of the latter may advantageously be adapted intraoperatively to the individual anatomical situation and the situation resulting from an injury by the positioning device module according to the present invention.

Furthermore, using the positioning device module according to the present invention, the angle of the interlocking screw penetrating the intramedullary nail may be varied intraoperatively, e.g. to reposition fracture fragments or to adapt them in an anatomically correct way.

The positioning device module according to the present invention may be advantageously connected and adapted with positioning devices being designed in different constructions or structures. Only the interface for the adapter is to be adapted for the connection. Thus, different positioning devices, e.g. from different manufacturers and/or for different usages may be used. Different usages may be e.g. different bones (e.g. humerus, tibia, femur) as well as different species (e.g. human or animal).

Using the positioning device module according to the present invention, the operating time may advantageously be shortened and the radiation exposure for the operator advantageously reduced.

Using the positioning device according to the present invention, it is advantageously possible to correct, during an operation, minor misalignments when positioning and/or when screwing in (the so-called "setting") of interlocking screws into an intramedullary nail arranged in the long bone.

The position and the angle of bores for the interlocking screws and their position may advantageously be adapted still intraoperatively to the individual anatomical situation and to an injury-caused situation by means of the positioning device according to the present invention.

Furthermore, by means of the positioning device according to the present invention, the angle of the interlocking screws penetrating or reaching through the intramedullary nail may still be varied intraoperatively in order, e.g., to reposition fracture fragments or to adapt them anatomically correctly.

By means of the snap-in arrangement of the positioning device according to the present invention, the snap-in arrangement may advantageously be locked in a defined position along the longitudinal axis of the sleeve by form-fit connection between the bolt of the snap-in arrangement of the guiding bow on the one hand and the sleeve on the other. Furthermore, this form-fit or positive connection may be implemented or executed, by means of a long hole, in the circumferential direction of the sleeve in order to provide or allow a defined or limiting rotation between the guiding bow and the sleeve. This enables the surgeon within certain limits to intraoperatively align the interlocking devices relative to the intramedullary nail.

By means of the markings for the position control of the guiding bow relative to the sleeve, the surgeon may advantageously be supported when tracing or monitoring the position of the snap-in positions and/or of longitudinal holes along the long axis of the sleeve. By means of markings, the position of the snap-in positions and/or long holes or longitudinal grooves may be advantageously visualized. The orientation (rotation direction and indication of the angle of the guiding bow relative to the sleeve) of the guiding bow relative to the intramedullary nail or to the through-openings for screwing in the interlocking screws into the intramedullary nail may thus be advantageously facilitated.

By the present invention, the positioning device may be securely and simply connected, releasably, to the intramedullary nail to be fixed. Thus, the positioning device may be decoupled and removed from the secured intramedullary nail. In this, the first component, a web-groove connection, may serve the torsion-proof mutual arrangement of the sleeve and the intramedullary nail. It may advantageously ensure that the intramedullary nail is not rotating or co-rotating during the screwing or during the release of the screw connection between the guiding device and the intramedullary nail. This contributes to not jeopardizing the position of the intramedullary nail reached in the bone, by applying of torque, when connecting the positioning device to the intramedullary nail or when releasing or decoupling the positioning device from the intramedullary nail.

The present invention is exemplarily explained with regard to the accompanying figures, in which identical reference numerals refer to the same or similar components. The following applies in each of the schematically simplified figures:

FIG. 1 shows a perspective view of a positioning device module according to the present invention, a positioning device, an intramedullary nail and a humerus;

FIG. 2a, b show the positioning device module according to the present invention of FIG. 1 in a mounted or assembled state or in single-part representation;

FIG. 3a, b show the positioning device module according to the present invention of FIG. 1 having a locking device in a mounted state or in a non-mounted state;

FIG. 4a-e show the positioning device module according to the present invention of FIG. 1 which is oriented towards the through-opening of an intramedullary nail by the locking device and an imaging device;

FIG. 5a, b show the positioning device module according to the present invention of FIG. 1, a humerus with the intramedullary nail or a drill arrangement for drilling through the bone;

FIG. 6a, b show the positioning device module according to the present invention of FIG. 1, the intramedullary nail and a drill bit in a mounted state or in a non-mounted state;

FIG. 7 shows the positioning device module according to the present invention of FIG. 1 and a humerus having a screwed intramedullary nail;

FIG. 8a, b show a set according to the present invention having the positioning device module according to the present invention of FIG. 1 and an extension device in a mounted state or an extension device with an adapter as single parts;

FIG. 9a-f show different embodiments of a targeting device and an adjusting device;

FIG. 10a-f show different embodiments of the targeting device and of the drill bit, as well as an intramedullary nail fixed by interlocking screws;

FIG. 11a-c show different views of a further embodiment of the positioning device module according to the present invention;

FIG. 12a-h show the embodiment of FIGS. 11a-c in various perspective views;

FIG. 13a-e show a positioning device module according to the present invention in an embodiment having two wedge plates;

FIG. 14a-d show the positioning device module according to the present invention with eccentric and threaded plate;

FIG. 15a-d show the positioning device module according to the present invention in a further embodiment with eccentric and latching plate;

FIG. 16a-c show the positioning device module according to the present invention in a further embodiment having a nut and a threaded plate;

FIG. 31 shows the snap-in arrangement of the embodiment of FIG. 30 in detail;

FIG. 32 shows a further snap-in arrangement having a spiral spring;

FIG. 33 shows a further snap-in arrangement having a leaf spring and a lever;

FIG. 35 shows a further snap-in arrangement having a snap-in pin for laterally inserting the latter into the sleeve from;

FIG. 36 shows a two-piece targeting device of the positioning device;

FIG. 37 shows an adjusting device having a snap-in device for fixing the targeting device at the guiding bow;

FIG. 38 shows a targeting device having a hole arrangement for an instrument;

Figure 45:
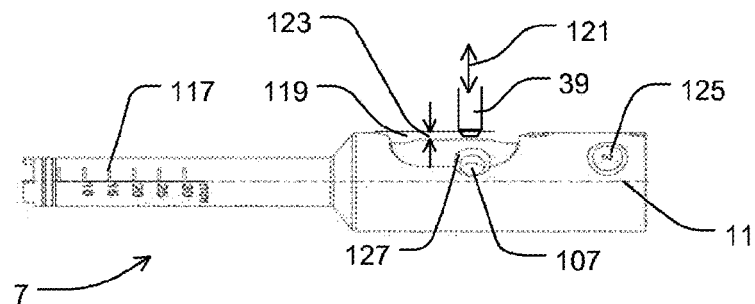
Figure 48:
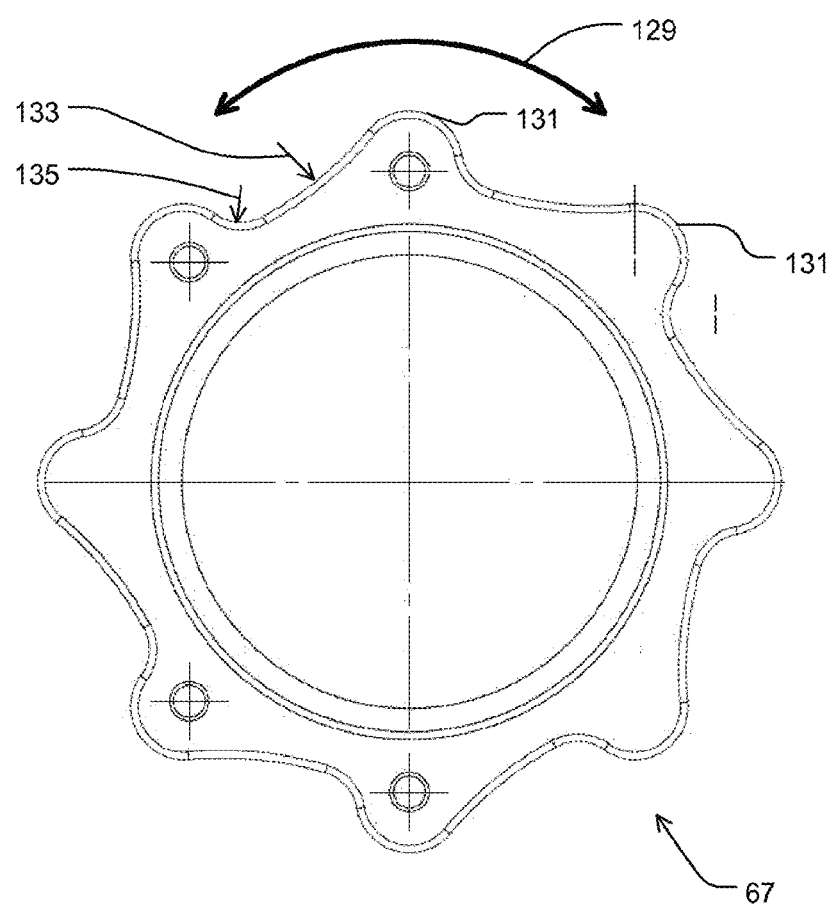

FIG. 45 bis 47 show different views of a further sleeve without a sliding guide;

FIG. 48 shows a further tension wheel.

Figure 49:
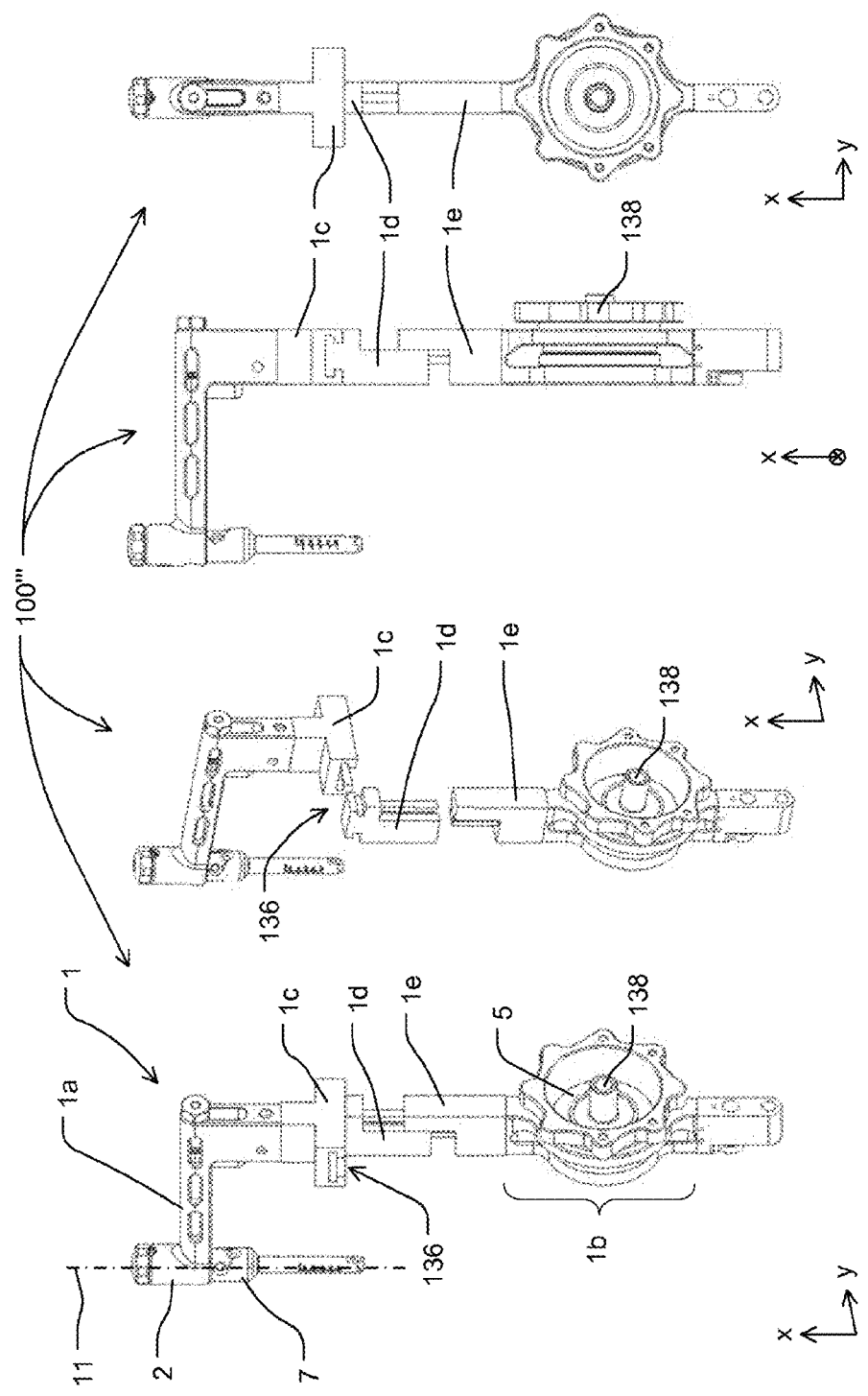
Figure 51:
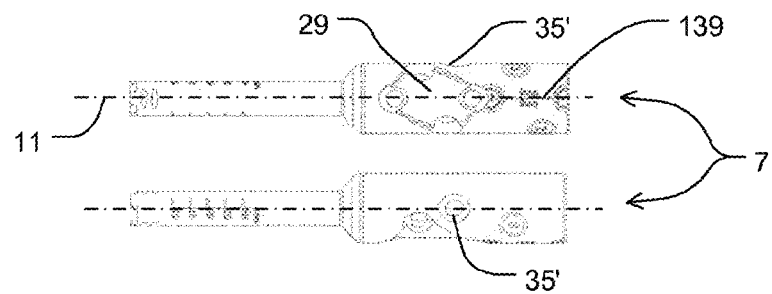
Figure 52A:
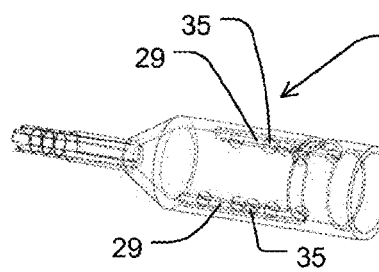
Figure 53:
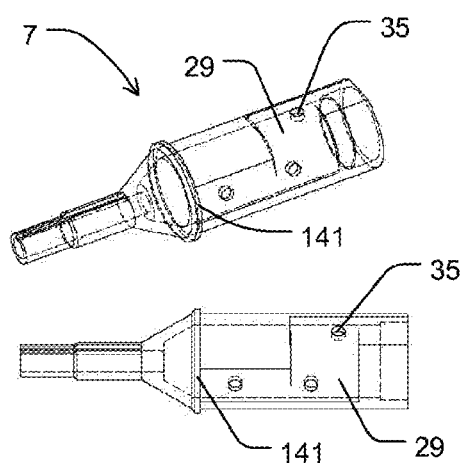
Figure 54:
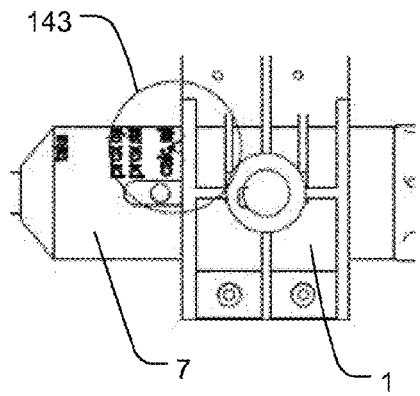
Figure 60A:
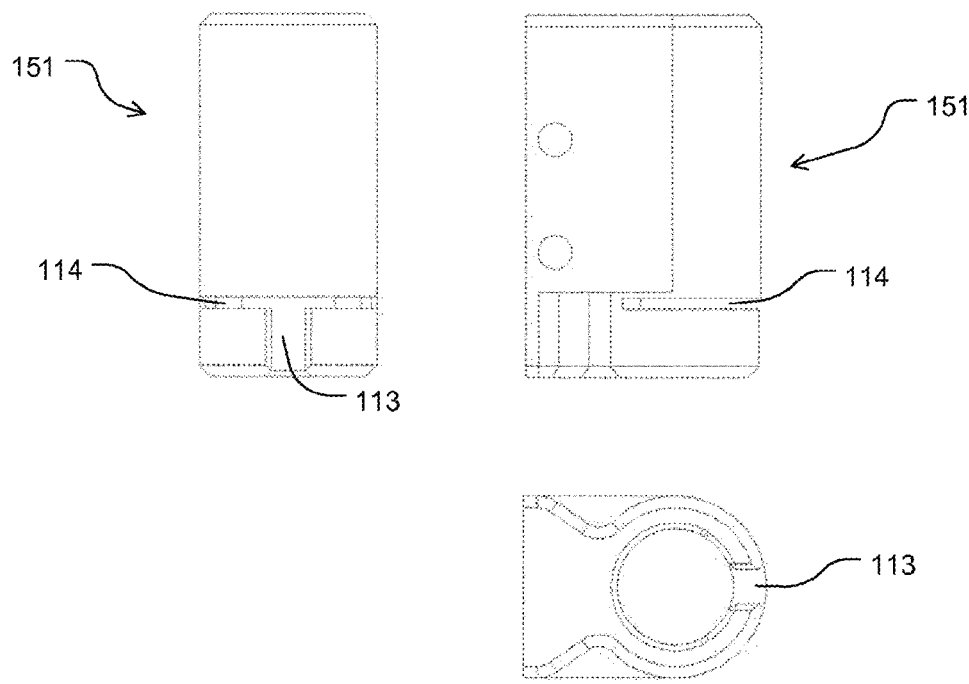
Figure 60B:
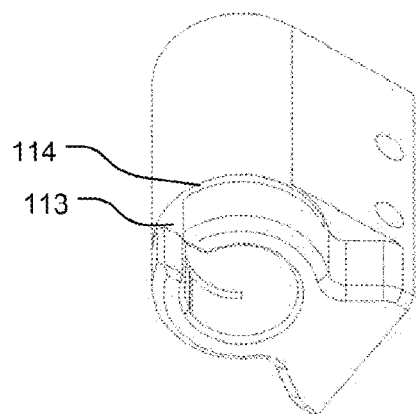
Figure 60C:
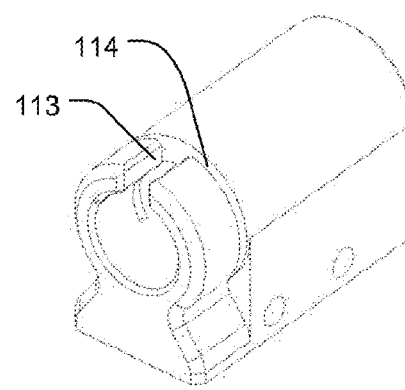

FIG. 49a-d show a further positioning device having additional guiding elements for shifting the targeting device;

FIG. 50a-d show the positioning device of FIG. 49 having positioning markings and fixing screws for the guiding elements;

FIG. 51 shows a further slide guide of the sleeve with an additional snap-in position;

FIG. 52 a, b show a further line-shaped slide guide;

FIG. 53 shows a further slide guide with a stopper;

FIG. 54 shows a sleeve with a written marking;

FIG. 55 a, b show a reinforced guiding bow;

FIG. 56 shows a guiding bow optimized by injection moulding;

FIG. 57 a-c show an adjusting mechanism of the targeting device;

FIG. 58 *a-c* show a further adjusting mechanism of the targeting device;

FIG. 59 *a-c* show the targeting device with a spring mechanism for fixing an instrument; and FIG. 60 *a-c* show a distal attachment with a spring mechanism.

Figure 1:
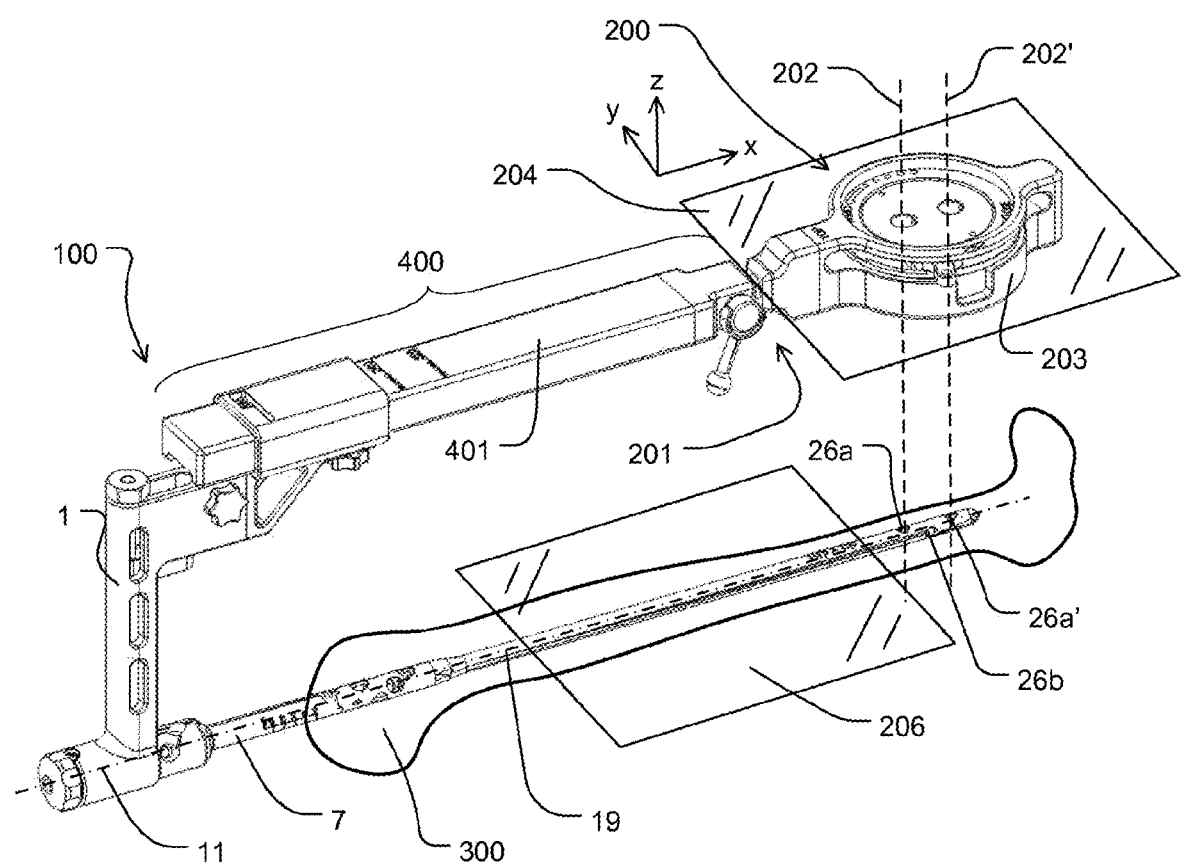

FIG. 1 shows a positioning device module 200 according to the present invention, a positioning device 100, an intramedullary nail 19 and a humerus 300 in a perspective view.

The humerus 300, the intramedullary nail 19 and the positioning device 100 are merely exemplarily selected. The positioning device module 200 according to the present invention may in other embodiments according to the present invention with an intramedullary nail 19 (could alternatively be a prosthesis or plate) be inserted into a shin bone (tibia), into a thigh bone (femur) or in another long bone, in particular for the medical care of fractures. Alternatively to the intramedullary nail 19, the positioning device module 200 according to the present invention may be used for fixing prostheses, in particular revision prostheses e.g. of femur revision prostheses, for fixing long bones by plates, in particular by osteotomy plates, or for fixing by other devices.

The positioning device 100 comprises in this embodiment a guiding bow 1, an extension device 401 and a sleeve 7. The sleeve 7 is releasably connected to the intramedullary nail 19.

The guiding bow 1 may purely optionally be pivoted and shifted together with the extension device 401 and the positioning device module 200 relative to the intramedullary nail 19 and relative to the sleeve 7, such that the positioning device module 200 may be additionally aligned in order to screw the intramedullary nail 19 to the humerus 300 by the interlocking screw 21, 21' (not shown in FIG. 1).

The result of said alignment is indicated by the two dashed alignment lines 202, 202'. The longitudinal axis 11 of the sleeve 7 extends in FIG. 1 in x-direction.

The positioning device module 200 according to the present invention may be moved relative to the positioning device 100 by at least or by exactly one optional joint 201. The joint 201 is purely exemplarily embodied as a ball joint 201 in the embodiment according to the present invention in FIG. 1. The positioning device module 200 according to the present invention may be pivoted or rotated by the ball joint 201 about three axes being respectively perpendicular to each other.

The joint 201 illustrated in FIG. 1 and in several further figures is optional and is not provided in several embodiments of the positioning device module 200 according to the present invention.

A first rotation axis may be described as y-axis which passes through the joint 201 and is arranged in a main extension plane 204 which is spanned by or through the positioning device module 200 according to the present invention. The main extension plane 204 lies parallel to a second plane 206 in which second plane 206 lies the longitudinal axis 11 of the intramedullary nail 19.

In several applications, the intramedullary nail 19 may deform during and/or due to its insertion into the long bone, which is exemplarily a humerus in FIG. 1. In particular, the distal region of the intramedullary nail 19, i.e. the end region (in FIG. 1 the end region is shown on the right and comprises the distal through-openings 26a, 26a' and 26b) may bend due to the anatomy within the long bone. This deformation may take place in one or more planes and may additionally represent a twist. The deformation is initially not visible from the outside and should be determined, for example using an imaging process or procedure, prior to drilling and inserting interlocking screws. Subsequently, the positioning device module 200 must be repositioned and aligned by the joint 201, and if necessary by a length adjustment with the aid of the extension device 401. This alignment is described in more detail with reference to FIGS. 4a to 4c. The extension device 401 may be shifted in x-direction. The extension device 401 may increase or decrease the distance between the positioning device module 200 and guiding bow 1.

The positioning device module 200 is connected to the positioning device 100 by a section for connecting these two units. In the example of FIG. 1, the connection may optionally be carried out by the joint 201. The section for connecting may therefore be or comprise the joint, however it must not be as such.

Figure 2A:
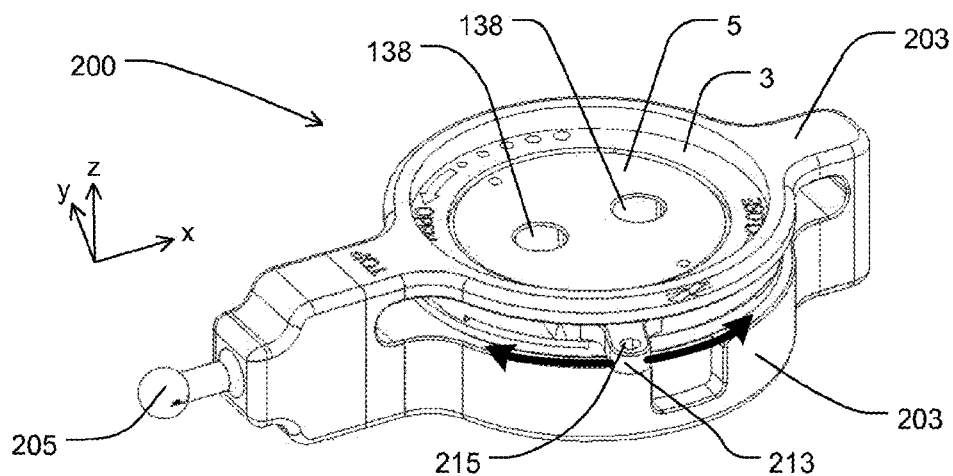

FIG. 2a shows the positioning device module 200 according to the present invention in a mounted state in an enlarged illustration compared to FIG. 1. The positioning device module 200 optionally comprises a targeting device 5, an adjusting device 3 and a receiving section 203. The receiving section 203 may be understood as a section or area of the guiding bow 1 or as a guide element. The main extension plane of the receiving section 203 lies in, FIGS. 1 and 2a, in the plane being spanned by the axes x and y. In this, it may, unlike what is shown in FIG. 1 or FIG. 2a, optionally comprise also a curved or arched, e.g. spherical, area projecting in z-direction.

The targeting device 5 is optionally arranged to be pivotable relative to the adjusting device 3 about the z-axis and optionally to be shiftable (may be lifted and lowered) in z-direction. Thus, for example the two through-openings 138 of which there may be provided more or less than two, may be aligned in the xy-plane and optionally in the z-direction. The alignment or shifting may be carried out using a bar 213 arranged on the circumference of the adjusting device 3, preferably projecting radially to the outside over said circumference. The bar 213 may optionally comprise a through-opening 215 or recess. A benefit or usefulness of the bar 213 is described with reference to FIG. 3a.

Figure 2B:
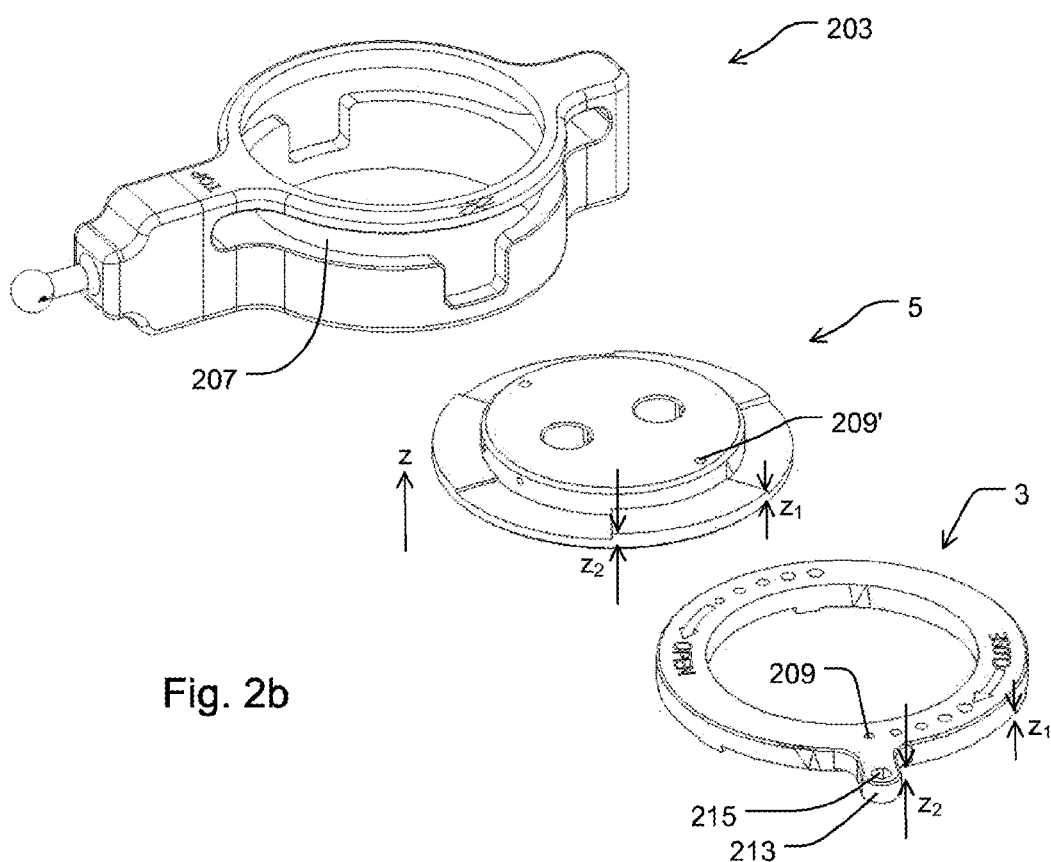

FIG. 2b shows the positioning device module 200 according to the present invention in a single-part view or exploded view. The targeting device 5 is optionally segmented over its circumference or subdivided in single regions. Alternatively, the targeting device 5 comprises segmented regions, optionally along it circumference. Said segmented regions may be wedge-shaped in z-direction. The height of these segments (i.e. their extension in the z-direction) is thus uneven along the circumference. For example, the height $z_1$ at one end of the segment or region being wedge-shaped in the longitudinal section is significantly smaller or lower than the height at the opposite end of the segment or region in which the wedge has the height $z_2$. The wedge-shaped, segmented regions are located optionally also mirror-inverted on the bottom of the adjusting device 3. The wedge shape of the wedge-shaped, segmented regions is indicated by the two different heights $z_1$ and $z_2$. Consequently, if the targeting device 5 and the adjusting device 3, which here are exemplarily designed as annular section or ring section, lie next to each other such that the height $z_1$ of the targeting device 5 lies above the recess $z_1$ of the adjusting device 3, which respectively applies to the height $z_2$ and recess $z_2$, then the total height of the targeting device 5 and the adjusting device 3 lying on it is for example $z_3$.

When the targeting device 5 and the adjusting device 3 are rotated against each other in a clockwise direction, then the wedge heights $z_1$ and $z_2$ are shifted relative to the recesses $z_1$ and $z_2$ such that the total height is higher or more than $z_3$. With reference to the annular slot 207 of the receiving section 203 this means for example that, at a minimum common height $z_3$ of targeting device 5 and adjusting device 3, a simultaneous rotation and alignment of the two through-openings 138, as described in FIG. 2a, is possible with a small play in the annular slot 207.

When the targeting device 5 and the adjusting device 3, are, e.g. subsequently, rotated against each other in a counterclockwise direction, then the height $z_3$ increases and both the targeting device 5 and the adjusting device 3 are fixed or clamped in a frictional connection in the annular slot 207 at its upper and lower limit. Such a fixation is advantageous if the targeting device 5 is to be first aligned within the adjusting device 3 (see description of FIG. 2a), and then the entire positioning device module 200 is to be aligned to the distal through-opening 26a, 26a' (see description of FIG. 1).

In this exemplary present embodiment, the targeting device 5 is led or guided in or at the adjusting device 3. With respect to the adjusting device 3, the targeting device 5 may in this embodiment only be rotated. If, however, the targeting device 5 is shifted, then there is a shifting of both the targeting device 5 and the adjusting device 3 within the receiving section 203. If the adjusting device 3 is rotated against the targeting device 3, then there is a height difference or a height increase of the overall package of targeting device 5 and adjusting device 3. This height difference or height increase causes both a frictional connection between the targeting device 5 with the adjusting device 3 on the one hand and the limit of the annular slot 207 (or of an alternatively provided slit) on the other hand.

Optional arrows, position markings 209 and the terms "OPEN" and "CLOSE" are arranged on the upper side of the adjusting device as optical help or aid in or for the joint fixation of the targeting device 5 and the adjusting device 3 relative to the receiving section 203. The position markings 209 may be used based on a position marking 209' on the upper side of the targeting device 5 in order to indicate the friction status and the current degree of fixation.

Figure 3A:
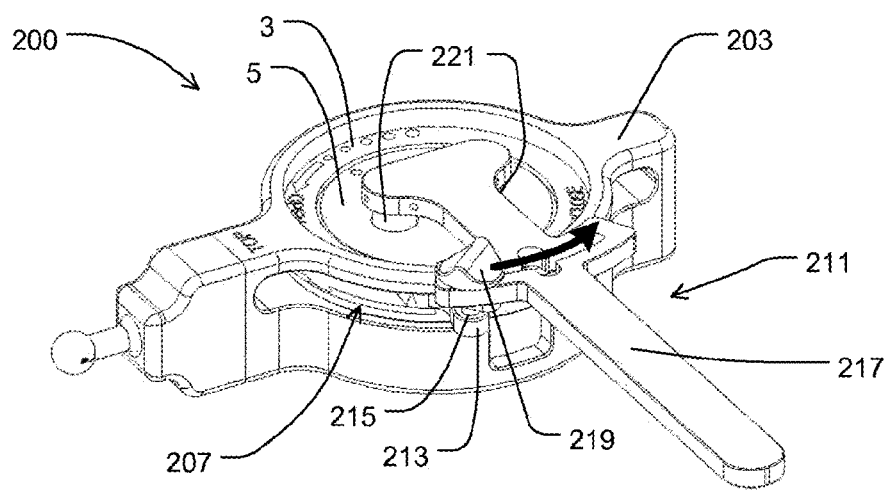

FIG. 3a shows the positioning device module 200 according to the present invention with a locking device 211. The locking device 211 is shown mounted on or at the positioning device module 200. The locking device 211 exemplarily comprises an adjusting fork 207 and a plug-in bolt 219. Alternative connection solutions to the plug-in bolt 219 are also encompassed by the present invention.

The plug-in bolt 219 may—before or after inserting the adjusting fork 217 into the targeting device 5—be connected to the adjusting fork 217.

Figure 3B:
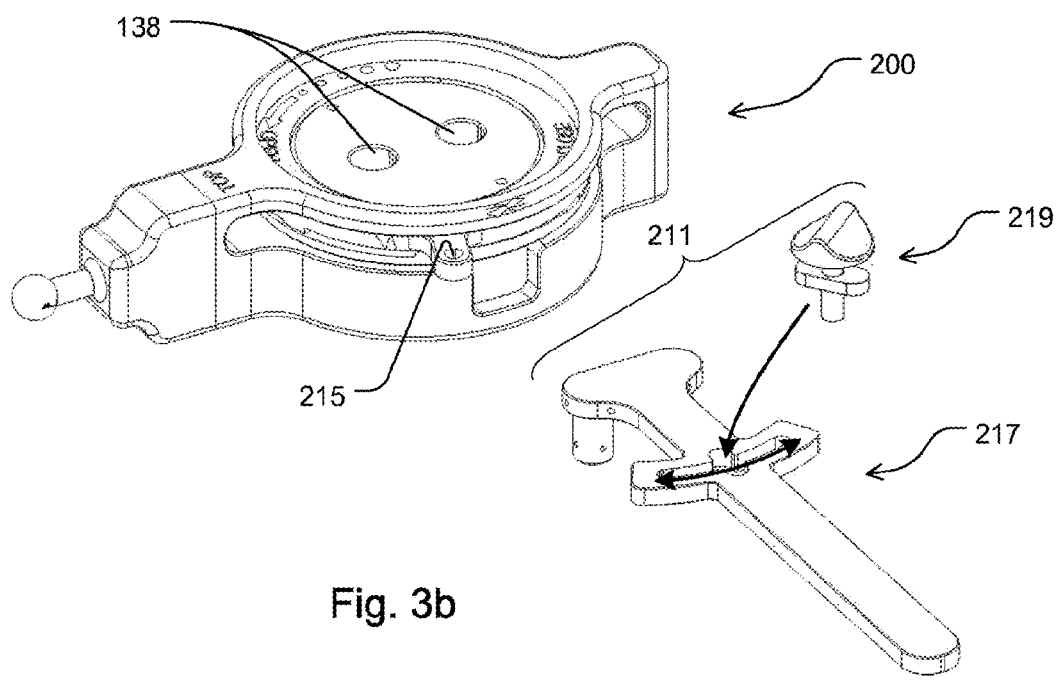

When mounting prior to inserting the adjusting fork 217 into the targeting device 5, the plug-in bolt 219 is initially inserted or plugged in through a groove arranged in longitudinal direction of the adjusting fork 217 (see the simple arrow in FIG. 3b). Subsequently, the plug-in bolt 219 may be shifted and optionally rotated (arrow with two arrow directions) within the longitudinal groove perpendicular to the longitudinal axis of the adjusting fork 217. Subsequently, the adjusting fork 217 is inserted with the plug-in bolt 219 in both through-openings 138. In this, care should be taken that the plug-in bolt 219 engages in the through-opening 215, i.e., the adjusting device 3 is to be aligned with the bar 213 accordingly.

When mounting after inserting the adjusting fork 217 into the targeting device 5, the bar 213 must be positioned together with the through-opening 215 directly below the central, cross-shaped opening of the adjusting fork 217 in order to be able to connect the plug-in bolt 219 to the adjusting device 3. Subsequently, the adjusting device 3 may be rotated by the adjusting fork 217 and the plug-in bolt 219 against the targeting device 5 which is exemplarily held by hand and prevented from co-rotation and, thus, for example, fixed and clamped. To clamp, the plug-in bolt 219 would be, with regard to FIG. 3a, shifted in the groove from right to left (i.e. counterclockwise and against the marked arrow direction of FIG. 3a).

In the view of FIG. 3a, the plug-in bolt 219 has been already moved to the left, i.e. clockwise; the targeting device 5 is thus fixed with the adjusting device 3 in the annular slot 207 or in the receiving section 203 by clamping. This frictional clamping process was explained in detail in FIG. 2b.

FIG. 3b shows a non-mounted state of the positioning device module 200 according to the present invention with the fixing device 211 of FIG. 3a, which encompasses the adjusting fork 217 and the plug-in bolt 219 or optionally consists thereof.

The fixing device 211 may be replaced by any other suitable fixing mechanism. It should be considered as an exemplary embodiment of the latter.

Figure 4A:
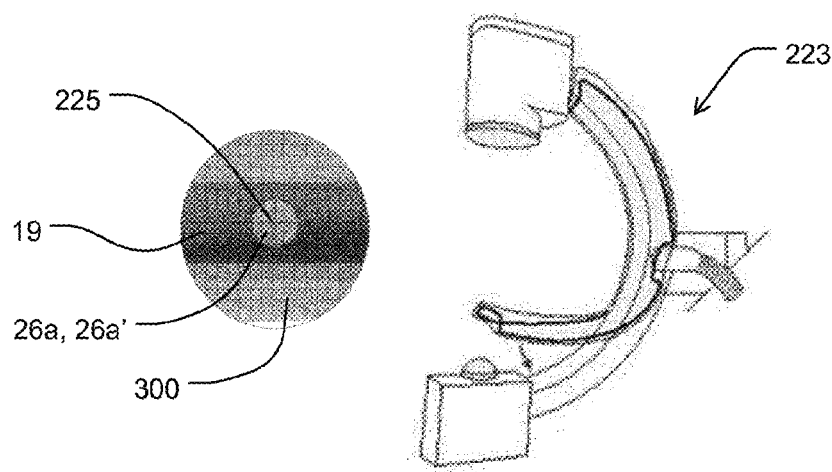

FIG. 4a shows a first step for aligning the positioning device module 200 according to the present invention with the distal through-openings 26a, 26a' (see FIG. 1) of the intramedullary nail 19.

A schematically simplified imaging device 223, in particular a mobile X-ray-C-arm 223, is illustrated on the right side of FIG. 4a. In this first step, the imaging device 223 is aligned such that long bone 300, certain sections thereof or the intramedullary nail 19 (left in FIG. 4a) ideally lie exactly perpendicular to the beam path of the imaging device 223. Alternatively, one should align the X-rays perpendicular to the section of the intramedullary nail 19 in which section the through-openings 26a, 26a' and 26b are located. This alignment is achieved by seeking to have, for example, a through-hole 26a, 26a' or 26b represented as a circular opening in the imaging device 223. Once this alignment is achieved, the next step, which is described in FIG. 4b, follows immediately or after further steps.

Figure 4B:
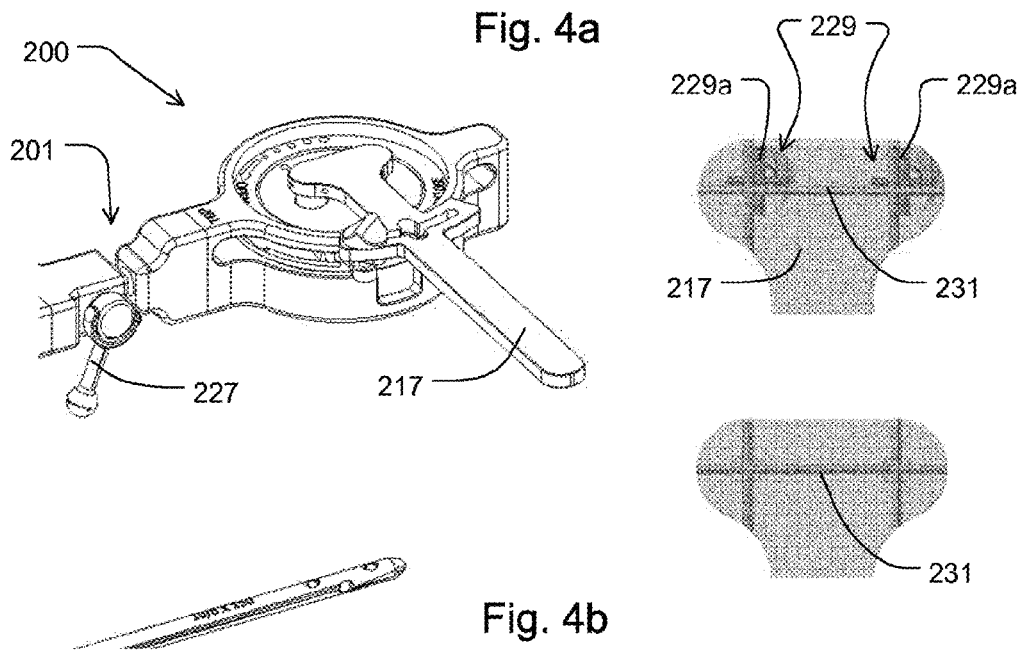

FIG. 4b shows the alignment of the adjusting fork 217 and, thus, the alignment of the two through-openings 138 in the axial direction of the through-openings 26a, 26a' or 26b. The adjusting fork 217 is stationary releasably connected to the positioning device module 200 via the through-opening 138. Due to fixing the adjusting fork 217 of the positioning device module 200 according to the present invention on said positioning device module 200, the latter may be aligned perpendicular to the beam path of the imaging device 223 by the adjusting fork 217. The adjusting fork 217 may comprise radiopaque position markers 229 being at different heights or being distant or at a distance from each other, as shown in the two right illustrations of FIG. 4b. These position markers 229 may be incorporated in, or connected to, the adjusting fork 217 in the form of crosses, balls, rings or any combination thereof. The crossing points or centers of these geometric position markers 229 are preferably located on an axis which is concentric with a longitudinal axis of the pins 248 of the adjusting fork 217. For aligning perpendicular to the beam path, the radiopaque position markers 229 shown in the two right illustrations of FIG. 4b, which are arranged on or within the adjusting fork 217, must as completely as possible be matched or brought into line. In other words, the two position markers 229, which are exemplarily designed as single crosshairs 229a, must overlap as completely as possible with the double crosshair 231 of the adjusting fork 217. Such overlapping is shown in the right, bottom illustration in FIG. 4b. Thus, the adjusting fork 217, and therefor also the positioning device module 200 according to the present invention or its main extension plane 204, is aligned perpendicular to the beam path of the imaging device 223. Now, a clamping lever 227 of the joint 201 is fixed. Said fixing takes place particularly by a frictional clamping, which has been described in detail in FIG. 2b.

The two single crosshairs 229a may be integrated, for example, in the two pins, or in the e.g. cylindrical shoulders 221 of the adjusting fork 217, which are inserted in the two through-openings 138.

The double crosshair 231 and/or the two single crosshairs 229a may likewise be designed differently, e.g. as higher in contrast, thicker and longer crosshairs. Optionally, additionally, e.g., rings, may be placed or integrated about the cylindrical shoulders of the adjustment fork 217 in order to improve the X-ray contrast during positioning. Other forms and designs are likewise possible.

As an alternative or in addition to the crosshair 225, other centering aids may also be used. For example, the crosshair may be made higher in contrast, thicker and longer.

Figure 4C:
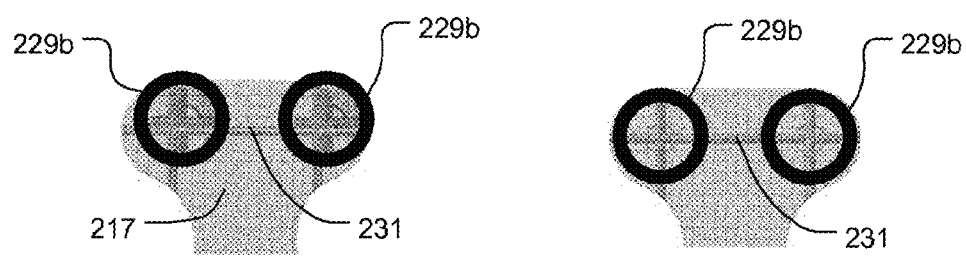

FIG. 4c shows an alternative or an additional embodiment of the position markers 229, which are annularly designed as ring markers 229b. The arrangement of the ring markers 229b at the adjusting fork 217 is shown in FIG. 4d.

Figure 4D:
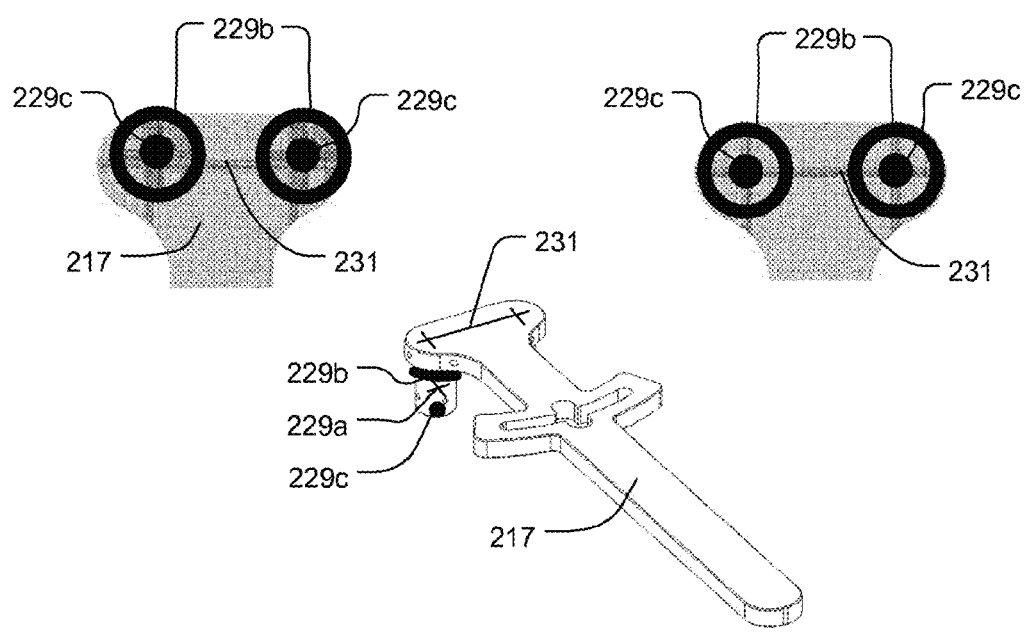

FIG. 4d shows a further alternative or additional embodiment of the position markers 229, which are ball-shaped designed as ball markers 229c. The optionally, additionally arranged ring markers 229b are also illustrated.

The bottom, perspective view of the adjusting fork 217 shows the arrangement of all optional, in particular radiopaque, markings of single crosshair 229a, ring marker 229b, ball marker 229c and double crosshair 231.

Figure 4E:
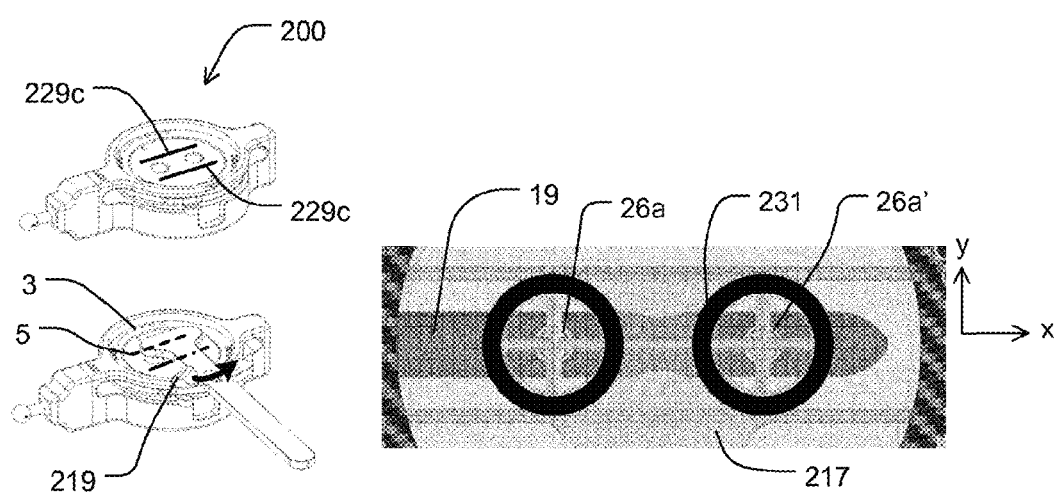

FIG. 4e shows the following, e.g. third, step for aligning the positioning device module 200 according to the present invention with the distal through-openings 26a, 26a' of the intramedullary nail 19. This alignment, which is also executed by or with or using the imaging device 223, takes place only in the x-y plane, since the movement in z-direction has already been determined fixing the clamp lever 227.

Initially, for further alignment, the plug-in bolt 219 is moved by the adjusting fork 217 in arrow direction to the right, i.e. counterclockwise, whereby the targeting device 5 and the adjusting device 3 are released again and become shiftable within the ring slot 207 (see description for FIGS. 2a and 2b). Subsequently, the double crosshair 231 of the adjusting fork 217 is aligned with the two distal through-openings 26a, 26a', by preferably manually guiding the adjusting fork 217, and is brought in line with said distal through-openings 26a, 26a', preferably by the coaxial arrangement of the openings to each other, as completely as possible. The result is shown in the right illustration of FIG. 4c. Additionally, the ring marker 229b may optionally be used for the alignment. In particular, the inner diameter of the ring marker 229b may be larger than the outer diameter of the intramedullary nail 19. With that, a clear X-ray contrast and thus a simpler alignment may be advantageously achieved. If this position is reached, the plug-in bolt 219 is again moved to the left and thus the targeting device 5 and the adjusting device 3 are again fixed and clamped.

Additionally or alternatively, the positioning device module 200 is aligned with regard to the intramedullary nail 19 using bar markers. This alignment may be carried out also as an intermediate step after the alignment step of FIG. 4a. For this intermediate step, it is not necessary that the adjusting fork 17 is arranged in the targeting device 5.

The alignment in this intermediate step is finished or completed when the bar markers are aligned parallel to the contour of the intramedullary nail 19.

In addition, it is also mentioned at this point that a complete matching or alignment of the different markers, as they are shown on the right in FIG. 4e, is actually not possible because, due to the illustrated vanishing point perspective, an ideal parallel illustration of the beam path is not possible. Therefore, slight deviations are possible and a sequential alignment first of the distal through-opening 26a and then of the second distal through-opening 26a' is to be executed.

Figure 5A:
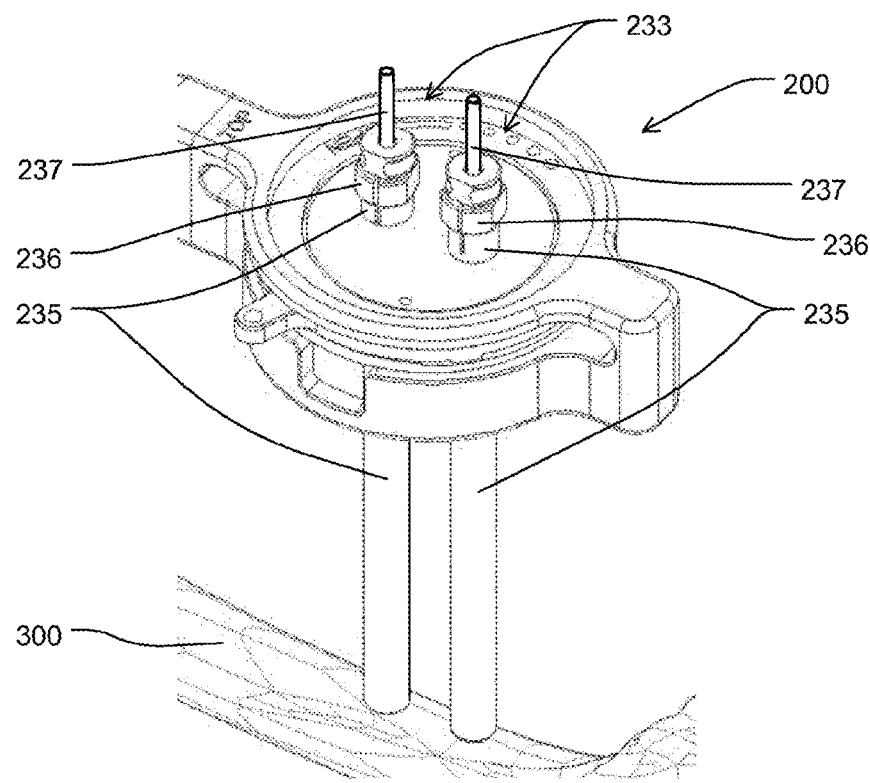

FIG. 5a shows the positioning device module 200 according to the present invention, the humerus 300 and a drill arrangement 233 for piercing the humerus 300. After completing the alignment of the positioning device module 200 according to the present invention with the distal through-openings 26a, 26a' of the intramedullary nail 19 (FIG. 4a to FIG. 4c) and both the joint 201 and the targeting device 5 and the adjusting device 3 are fixed by clamping, the intramedullary nail 19 is now fixed by being screwed to the bone 300. For this, there is advantageously no support needed by the imaging device 223 anymore. The plug-in bolt 219 and the adjusting fork 217 have already been removed.

The drill arrangement 233 optionally comprises at least one tissue protective sleeve 235, optionally drill bushings 236 and at least one drill 237. Bone material of the humerus 300 is drilled by the drill 237.

Purely exemplarily, the drill diameter may comprise 3.0 mm, 3.2 mm, 3.5 mm, 4 mm, 4.2 mm or any other value.

The drill bushings 236 are adapted to the drill diameter 237 such that a possible exact guiding and bone drilling may be achieved. Thereafter, the drill 237 is withdrawn again from the optional drill bushings 236 and from the optional tissue protective sleeve 235.

Figure 5B:
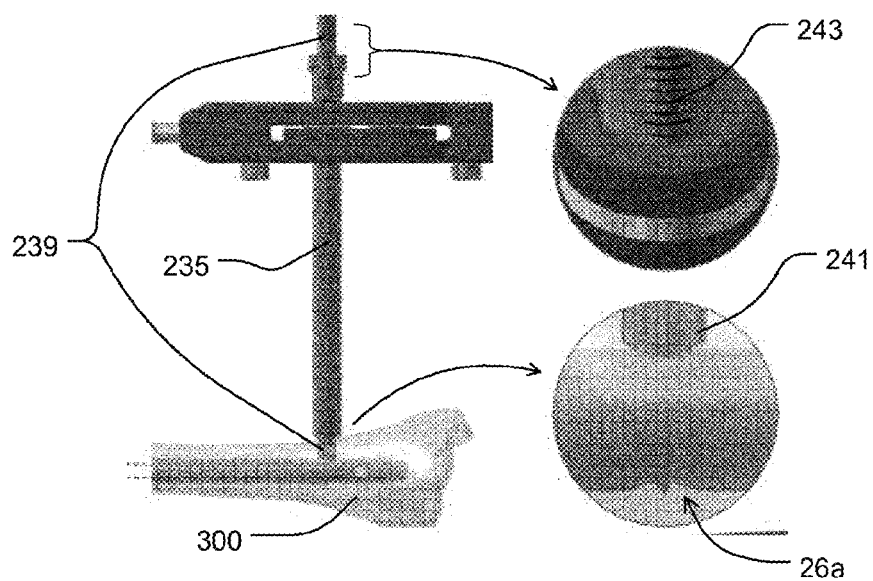

FIG. 5b shows a step following the first piercing of the humerus 300 (see FIG. 5a). In this step, a step drill 239 is inserted into the tissue protection sleeve 235. The step drill 239 comprises a shoulder 241 whose outer diameter is larger than the distal through-opening 26a of the intramedullary nail 19. The step drill 239 is drilled into the humerus 300 up to the shoulder 241 in the intramedullary nail 19. This drilling may be carried out manually or for example by an electrically driven drill. A manually guided drilling or a machine-induced drilling using a suitable sensor system, may advantageously prevent the intramedullary nail from damage due to too deep drilling. Damage to the intramedullary nail or intramedullary nail surface could create abrasive particles (of the drill and/or of the intramedullary nail) and may lead to or cause tissue reactions or other undesired reactions. Similarly, the step drill 239 may be designed so that it omits or dispenses with additional drilling using another drill and it is alone sufficient for piercing the bone and fitting the shoulder 241 on the intramedullary nail 19.

Subsequently, after the shoulder 241 fits to the intramedullary nail 19, the depth or length of the step drill 239, e.g. from the upper end of the tissue protection sleeve 235 to the shoulder 241, may be read and determined by a scale 243 located on the upper end of the step drill 239. This determination of the length is particularly advantageous in the case of a distal bending of the intramedullary nail 19 within the humerus 300, because in this way the exact position of the distal through-opening 26a, 26a' and 26b may be determined only after a bending has taken place. Thus, the read scale value corresponds to or may imply the deformation of the distal bending of the intramedullary nail 19.

Subsequently, the step drill 239 may be pulled out of the tissue protective sleeve 235 again. Afterwards, one, or with regard to FIG. 4c several, interlocking screws 21 (see FIG. 7) may be fixed into the humerus 300. The interlocking screws 21 may be the so-called cortical bone screws.

Figure 6A:
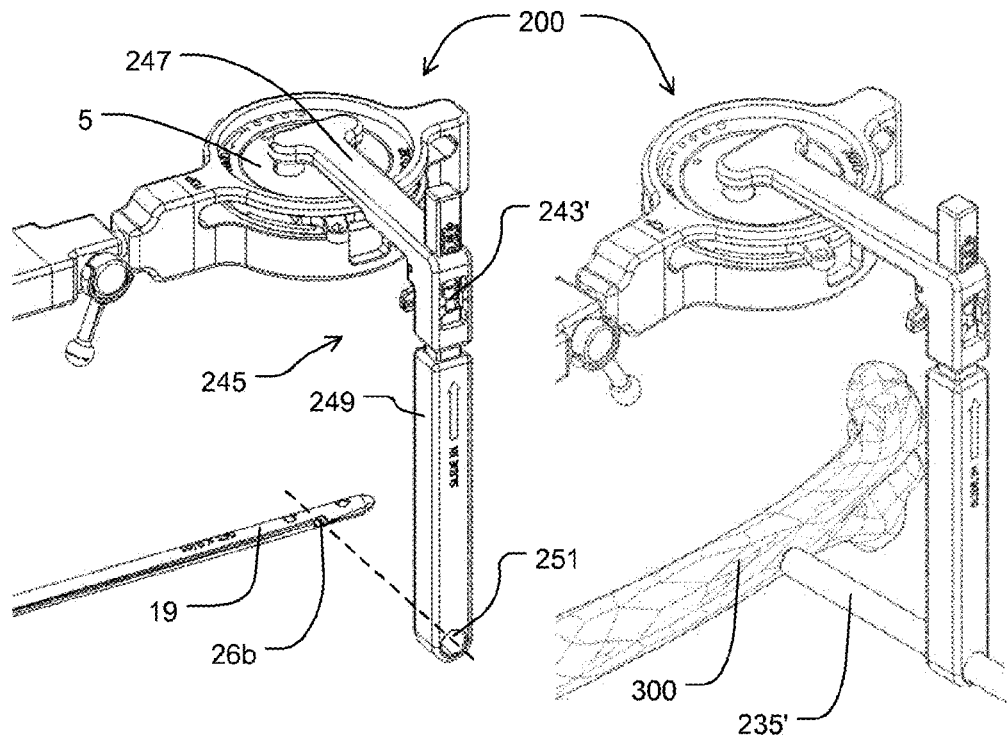

FIG. 6a shows the positioning device module 200 according to the present invention, the intramedullary nail 19, the humerus 300 and a drill bit 245 in a mounted state. The drill bit 245 allows an insertion of one or several interlocking screws 21' being exemplary offset to each other by, for example, 90 degrees. The interlocking screws 21' are in turn offset relative to the interlocking screws 21, as described in FIG. 5a.

The drill bit 245 optionally comprises a drill bit bracket 247 and a drill bit rail 249 which is inserted into the drill bit bracket 247. The drill bit bracket 247 is inserted into the targeting device 5 and is fixed relative thereto or therewith. This fixing may be done for example by pins 248 which are provided to be inserted into the through openings 138.

The length of the drill bit rail 249 is adjusted according to the value determined by the scale 243 and by the step drill 239 (see description of FIG. 5b) which value indicates that the distal end of the intramedullary nail 19 has been deformed. This adjustment is possibly based on an adjusting device which can be clearly seen in FIG. 6b. The adjustment is preferably carried out based on a further scale 243' on the drill bit rail 249. The adjustment may be carried out already before connecting the drill bit rail 249 to the targeting device 5. The adjustment using the scales 243, 243' allows an alignment of the through-opening or a (pass-)through-opening 251 of the lower end of the drill bit rail 249 with or to the distal through-opening 26b.

Subsequently, a tissue protection sleeve 235' may be inserted into the through-opening 251 analogously to the description of FIGS. 5a, 5b. The subsequent steps may be executed analogously to the steps described in FIG. 5a. These steps encompass a piercing of bone material of the humerus 300 by a drill bit and by a drill and inserting and fixing the intramedullary nail 19 in the humerus 300 using one or several interlocking screws 21 (see FIG. 7). Finally, the drill bit 245 is removed or demounted again.

Figure 6B:
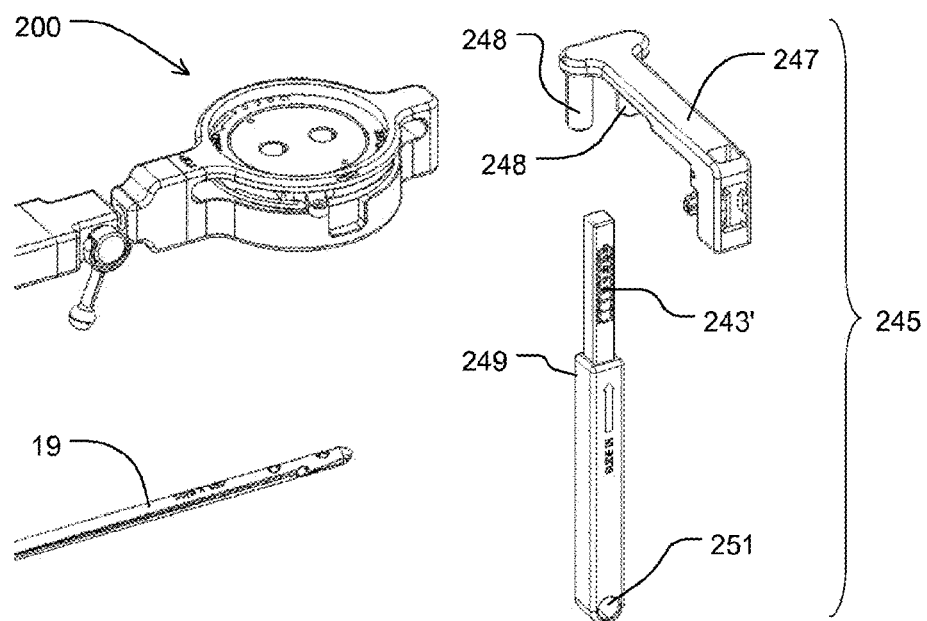

FIG. 6b shows the positioning device module 200 according to the present invention, the intramedullary nail 19 and the drill bit 245 with the drill bit bracket 247 and the drill bit rail 249 in single-part illustration, i.e. in the non-mounted state.

Figure 7:
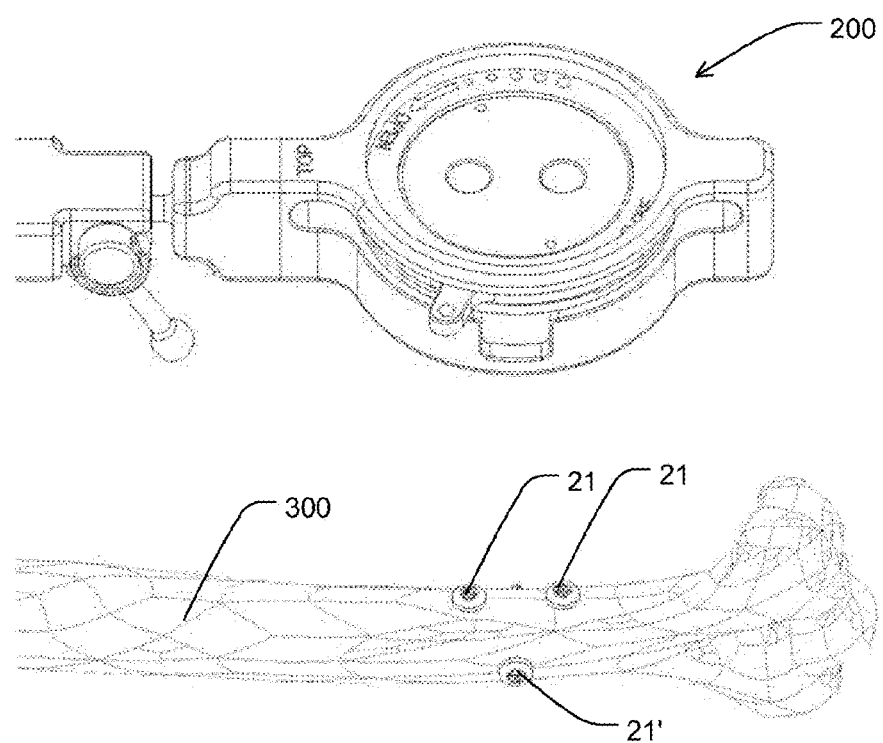

FIG. 7 shows the positioning device module 200 according to the present invention and a humerus 300 being screwed and fixed by three interlocking screws 21 to or with the intramedullary nail 19 arranged within the humerus 300.

Figure 8A:
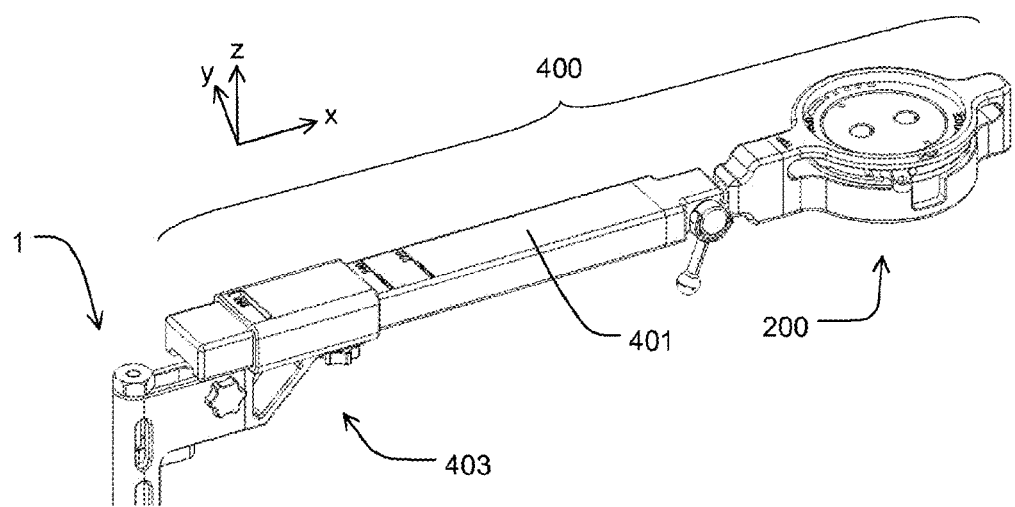

FIG. 8a shows the mounted state of an exemplary embodiment of a set 400 according to the present invention with the positioning device module 200 according to the present invention, an extension device 401 and an adapter 403.

The extension device 401 allows moving or shifting the positioning device module 200 according to the present invention in a positive and negative x-direction along the longitudinal axis of the extension device 401. Thus, for example, the alignment of the positioning device module 200 may be adapted with respect to the distal through-openings 26a, 26a' and 26b (see FIG. 1).

The set 400 according to the present invention may comprise a positioning device 100.

Figure 8B:
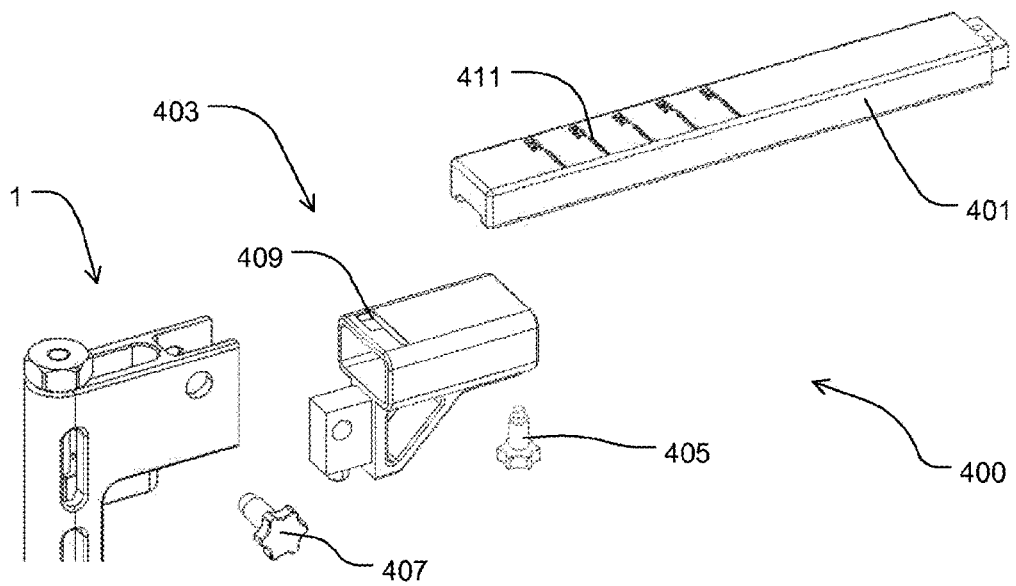

FIG. 8b shows a single-part illustration of the set 400 according to the present invention of FIG. 8a having the extension device 401, the adapter 403, an optional clamping screw 405 for fixing and clamping the extension device 401 at the adapter 403 and again an optional fastening screw 407 for releasably connecting the adapter 403 to the guiding bow 1.

The adapter 403 comprises an optional view field 409, in which an optional scale 411 of the extension device 401 may be read in the mounted state. In this way, the positioning device module 200 according to the present invention may advantageously be positioned simply, quickly and accurately.

FIG. 9a to FIG. 9f show different embodiments for fixing the targeting device 5 within the positioning device module 200 according to the present invention. These variants are alternative embodiments to the embodiment described in FIGS. 2a and 2b which have wedge-shaped sections for the frictional fixing and clamping of the targeting device 5 and the adjusting device 3 in the receiving section 203.

Figures 9A, 9B:
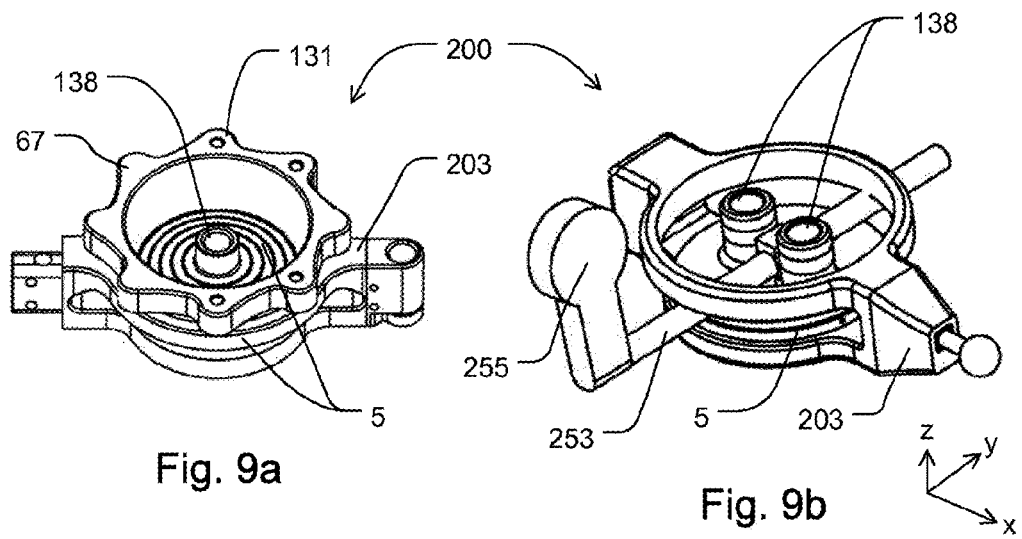

FIG. 9a shows an embodiment for the frictional fixing and clamping of the targeting device 5 in the receiving section 203 by a so-called tension wheel 67. The tension wheel 67 may be e.g. an outer thread at the circumference below the asymmetrical engagement contours, which engages in an inner thread of the receiving section 203. The targeting device 5 exemplarily comprises in this embodiment a through-opening 138. The positioning device module 200 according to the present invention comprises no adjusting device 3 in the variant of FIG. 9a.

The tension wheel 67 comprises in this embodiment asymmetrical engagement contours for, in particular manual, tightening and loosening. The asymmetrical engagement contour may be referred to as a sawtooth contour. The tension wheel 67 is tightened in a clockwise direction (relative to the view in FIG. 9a) and released in a counterclockwise direction. The flank in the clockwise direction is significantly flatter than the flank for releasing. In this, only a low or small torque may be applied for tightening the tension wheel. If the torque is increased too much, the hand or fingers used will slip over the nobs 131 when tightening manually. Thus, advantageously achieved is that no too high torques may be applied for tightening. Very high torques could cause damage or breakage of this component which is preferably made of plastic.

A tool may also be used as an alternative to a purely manual operation of the tension wheel 67.

FIG. 9b shows an embodiment with an eccentric rod 253, which is optionally mounted rotatably about its longitudinal axis by a guide fixed on the targeting device 5. The excentrity is due to the fact that the eccentric rod 253 is curved along its longitudinal direction. This curve helps that the eccentric rod 253 may move the targeting device 5 in z-direction (raise and lower) and may brace it against the receiving section 203 by a rotation about the longitudinal axis and by a lever 255 (which is formed in z-direction). In this way, the targeting device 5 may be fixed and clamped by the eccentric rod 253 after aligning it with the distal through-openings 26a, 26a' (see FIG. 1).

The positioning device module 200 according to the present invention comprises no adjusting device 3 in the variant of FIG. 9b.

Figure 9C:
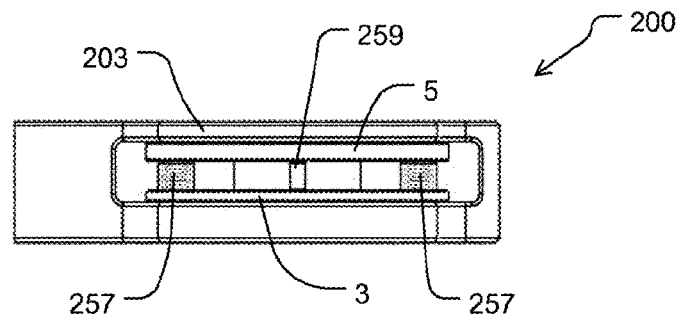

FIG. 9c shows an embodiment having a targeting device 5 and an adjusting device 3 which are both disc-shaped (or plate-shaped). Elastic spring elements 257, which are purely exemplarily designed as spiral springs in FIG. 9c, are arranged between the targeting device 5 and the adjusting device 3. They push or press the two disc-shaped devices apart and against the receiving section 203. This creates a force adjustable by the spring characteristic which allows moving or shifting the targeting device 5 and the adjusting device 3 in the receiving section 203 against the frictional resistance between the devices and the receiving section 203. After aligning the targeting device 5 with the distal through-openings 26a, 26a', the position of the targeting device 5 and of the adjusting device 3 may be fixed, locked and blocked by a fixing screw 259, which may be optionally designed as a tangent screw 259.

For mounting, the targeting device 5 and the adjusting device 3 are compressed under the prestressing force of the spring element 257 and inserted into the receiving section 203.

Figures 9D, 9E:
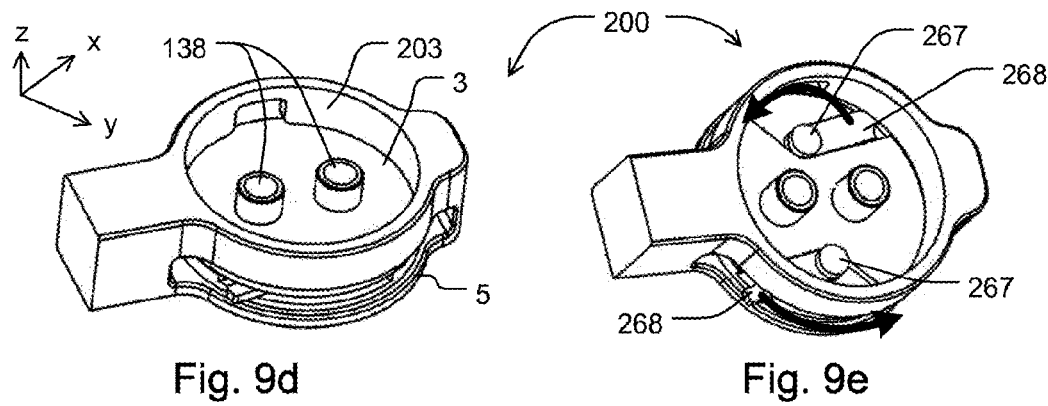

FIG. 9d, e show an embodiment having a targeting device 5 and an adjusting device 3, which are both designed disc-shaped (or plate-shaped) and are arranged coaxially in z-direction on each other. The two through openings 138 of the targeting device 5 may for example pass through the adjusting device 3 which in FIG. 9d is arranged on top in z-direction. Further, one of the two devices 3, 5 comprises one, two or more threads 267 (or at least one threaded section), by means of which the arranged devices 3, 5 may be moved. In this embodiment, the thread 267 is arranged below the adjusting device 3 and is arranged in FIG. 9e, in which the adjusting device 3 is not visible. The thread 267 may be attached to the bottom side of the adjusting device 3 for better guidance (raising and lowering of the adjusting device 3). The adjusting device 3 and the targeting device 5 may be moved or shifted in z-direction by the thread 267. The two devices 3, 5 may be moved against each other due to this movement in z-direction and may be fixed and clamped in the receiving section 203. The thread 267 is in this embodiment moved by a lever 268 in arrow direction by way of example.

Figure 9F:
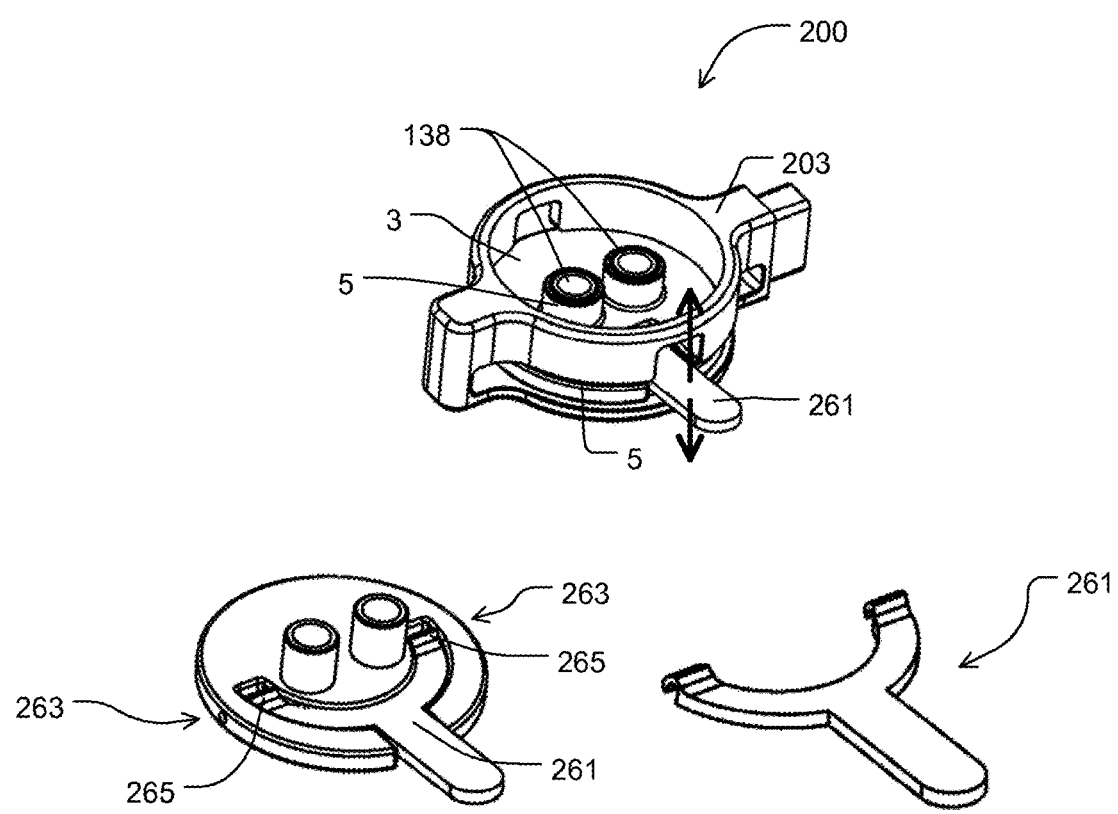

FIG. 9f shows an embodiment having a targeting device 5, an adjusting device 3 and a fork-shaped lever 261 (simply denoted as fork 261). The eccentric concept of this embodiment further comprises a hinge 263 by which the targeting device 5 (in FIG. 9f the targeting device 5 is arranged below the adjusting device 3) is connected and coupled with the adjusting device 3. The fork 261 comprises two eccentrics 265 at its fork-shaped ends. By operating the lever of the fork 261, the adjusting device 3 may be moved by the eccentrics 265 in z-direction (in FIG. 9f upwards and downwards). Due to this applied force, the targeting device 5 and the adjusting device 3 may be fixed and clamped in the receiving section 203.

FIG. 10a to FIG. 10f show different embodiments of the targeting device 5 and of the drill bit 245, as well as on intramedullary nail 19 fixed by interlocking screws 21.

FIG. 10a shows a positioning device module 200 according to the present invention having an adjusting device 3, a targeting device 5 and a receiving section 203. The targeting device 5 comprises a through-opening 138 for drilling and inserting an interlocking screw 21.

Figure 10D:
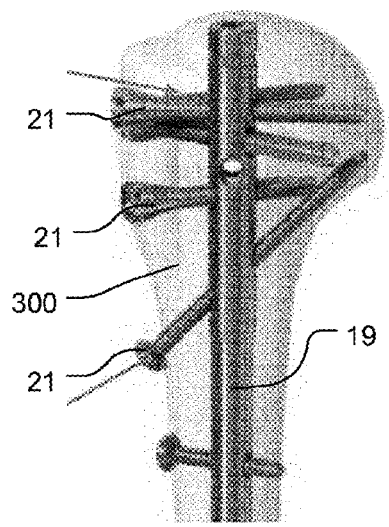

FIG. 10b shows a targeting device 5 of a positioning device module 200 according to the present invention. One of the two through-openings 138 (arranged on the left in FIG. 10b) is not perpendicular to the surface(by-plane) of the targeting device 5, but obliquely, for example in a 5-degree, 10-degree, 15-degree, 20-degree, 30-degree angle or in another angle towards the middle axis of the through-opening 138. Thus, through-openings which extend oblique may alternatively or additionally be supplied and fixed in the intramedullary nail 19 with interlocking screws 21, as exemplarily shown in FIG. 10d. The angled through-openings may also be arranged such that the longitudinal axes of the through-openings intersect in the nail, preferably on the longitudinal axis thereof.

FIG. 10c shows a targeting device 5 of a positioning device module 200 according to the present invention having an obliquely arranged through-opening 138. The cylindrical shoulder of the through-opening 138 may be arranged above or below the lead-through direction. In FIG. 10b, the cylindrical shoulder is arranged e.g. below, in FIG. 10c above the lead-through direction. For example, a tissue protection sleeve may be fixed by the cylindrical shoulder into the targeting device 5 in a more stable manner relative to an arrangement without cylindrical shoulder.

FIG. 10d shows exemplary embodiments of several interlocking screws 21 for fixing an intramedullary nail 19 in a long bone, e.g. in a humerus 300.

Figure 10E:
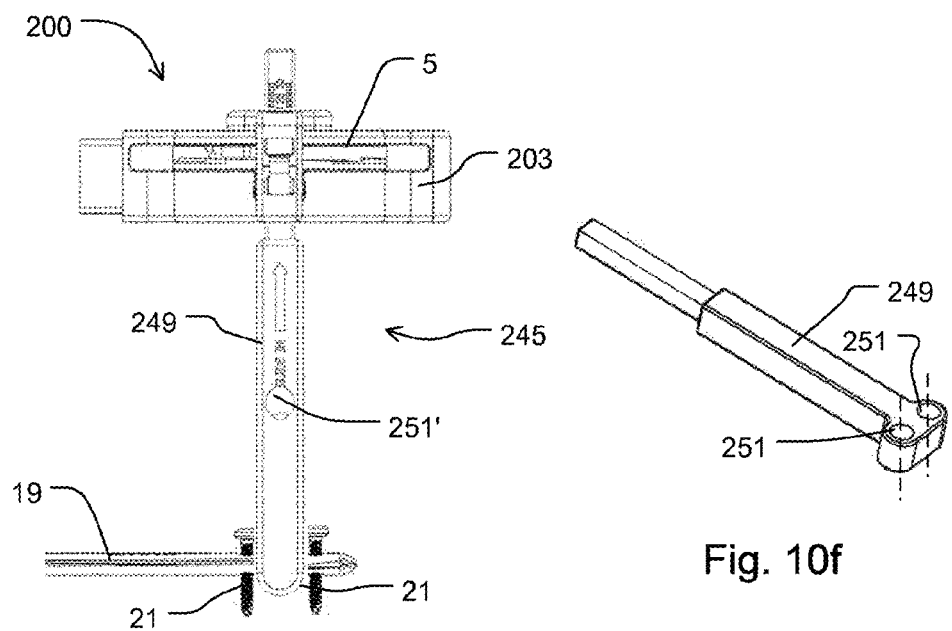

FIG. 10e shows a positioning device module 200 according to the present invention having a drill bit 245, an intramedullary nail 19 and two interlocking screws 21. The drill bit rail 249 of the drill bit 245 comprises additionally or alternatively an obliquely arranged through-opening 251' through which an obliquely arranged interlocking screw 21 may be screwed into the intramedullary nail 19. Likewise, the drill bit rail 249 may comprise further through-openings 251' in the same or in different angles.

Figure 10F:
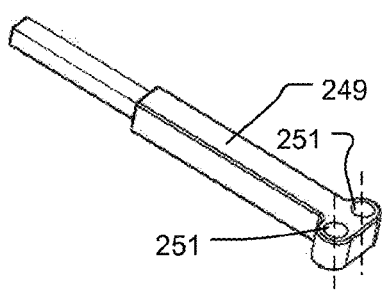

FIG. 10f shows a drill bit rail 249 with two through-openings 251, through which the two interlocking screws 21 arranged side by side may be screwed into the intramedullary nail 19 e.g. perpendicularly or in an angle different therefrom.

Figure 11A:
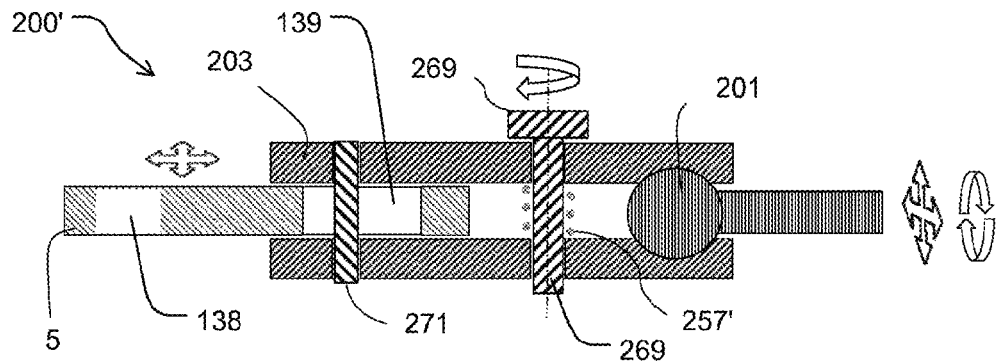

FIG. 11a shows a further embodiment of the positioning device module 200' according to the present invention in a mounted state.

The receiving section 203 is formed by two spaced plates. The targeting device 5 is arranged between the plates. The plates of the receiving section 203 are optionally pushed apart in the unlocked state by an elastic device or spring element 257, in FIG. 11a exemplarily designed as a spiral spring. In this state or in any other state in which the plates are not locked against each other, the targeting device 5 may be moved, and the in FIG. 11a purely exemplary two through-openings 138 may be aligned. After the plates of the receiving section 203 have been aligned, they are locked by a screw 269 or by another device and the targeting device 5 is frictionally fixed between the plates. A pin 271 serves for guiding the two plates of the receiving section 203 in a guide opening 139.

Figure 11B:
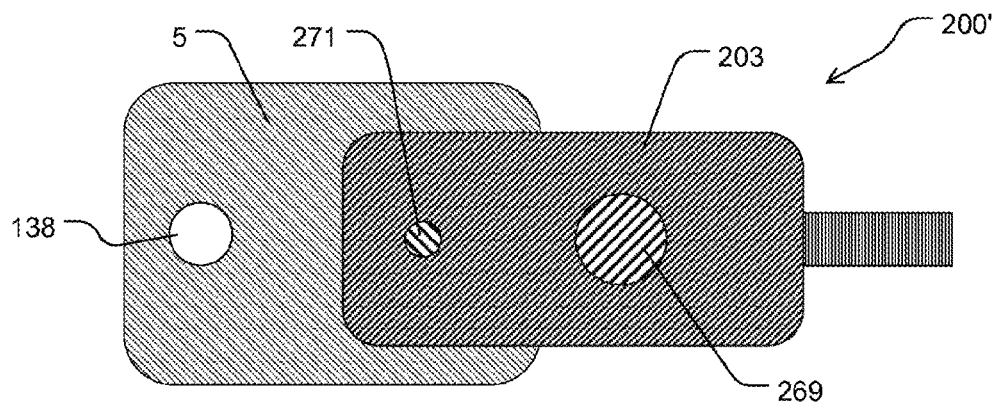

FIG. 11b shows a top view on the positioning device module 200' according to the present invention of FIG. 11a in a mounted state.

Figure 11C:
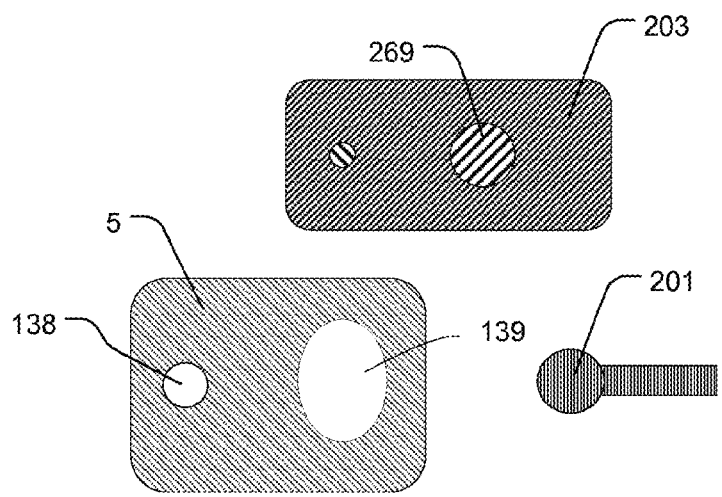
Figure 12A:
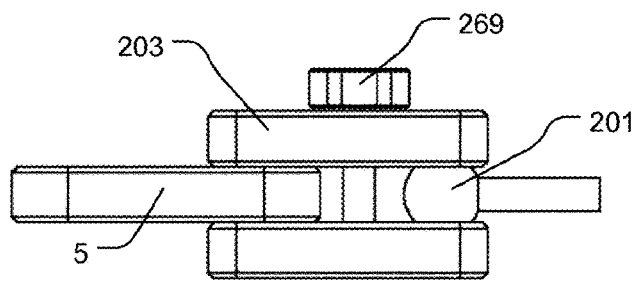
Figure 12B:
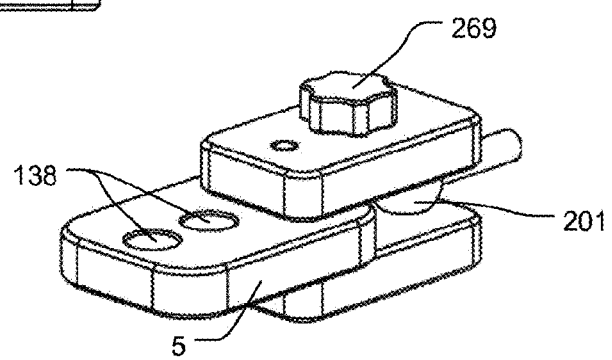
Figure 12C:
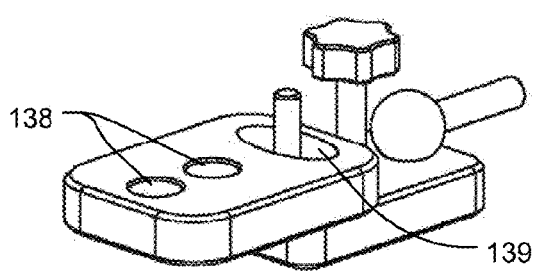
Figure 12D:
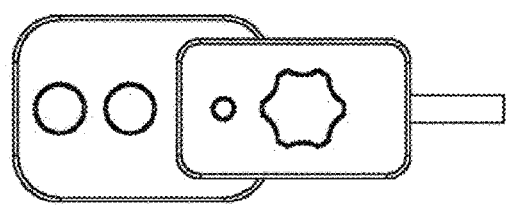
Figure 12E:
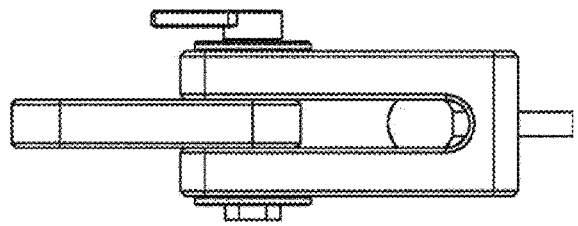
Figure 12F:
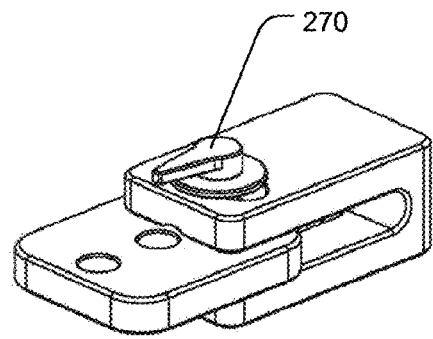
Figure 12G:
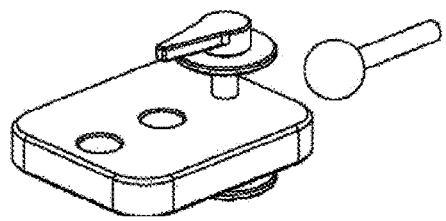
Figure 12H:
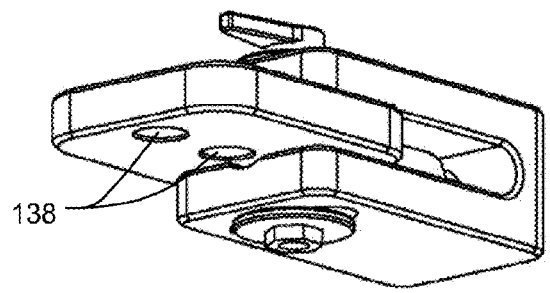

FIG. 11c shows the positioning device module 200' according to the present invention of FIGS. 11a and 11b in single-part illustration or in an exploded illustration.

FIG. 12a-h show the embodiment of FIG. 11a-c in different perspective views.

Unlike to the embodiment of FIG. 11a-c the embodiment of 12a-h comprises two distal through-openings 138. Furthermore, as an alternative to the screw 269, a tensioning device 270 for fixing the targeting device 5 in the receiving section 203 is illustrated in FIG. 12e-h.

FIG. 13a-e show a further embodiment of a positioning device module 200 having a targeting device 5 and a receiving section 203. The targeting device 5 comprises a disc-shaped plate 501 (the disc-shaped plate 501 in in the following simply referred to as joystick 501), a guiding sleeve 514 (in the following simply referred to as guide 514), a latching device 513 (the latching device 513 may be annular or e.g. in form of two circumferentially arranged barbs); the latching device 513 may be referred to as snap-in device, barbs or snap hooks, a first wedge plate 504, a second wedge plate 505 and a guiding device 502. The receiving section 203 may be referred to as joystick frame 203.

When referring in the following to a curved or flat surface of the joystick 501, preferably the surface of the joystick 501 is meant, which, when the positioning device module 200 is used, fits against a surface of the receiving section 203. In addition, a curved or flat surface of the receiving section 203 is preferably the surface which, when the positioning device module 200 is used, fits against the mentioned surface of the joystick 501. If the two mentioned surfaces are curved, it is possible to tilt the joystick 501 with respect to the receiving section 203. If the surface of the joystick 501 and of the receiving section 203 is flat, said joystick 501 and receiving section 203 may usually only be moved within a plane and a tilting is not possible, which may facilitate the drilling of parallel drill holes.

In the FIGS. 13a to 13e the joystick 501 comprises a curved surface which is preferably spherical, i.e. corresponds at least partially to a ball section.

Furthermore, the targeting device 5 comprises a guide 514 for the tissue protection sleeve 235 (see FIG. 5a) and at least one latching device 513 at the end of the guide 514. When mounting, the joystick 501 is inserted into the wedge plates 504, 505 by the guide 514 and is fixed or snapped in the longitudinal direction (axial) by the latching device 513. The optional two latching devices 513 may be elastically deformed during pressing, for example, due to two preferably long slots on the joystick 501. The two wedge plates 504, 505 and the optional guiding device 502 are fixed by the latching devices 513 in the receiving section 203.

Figure 13A:
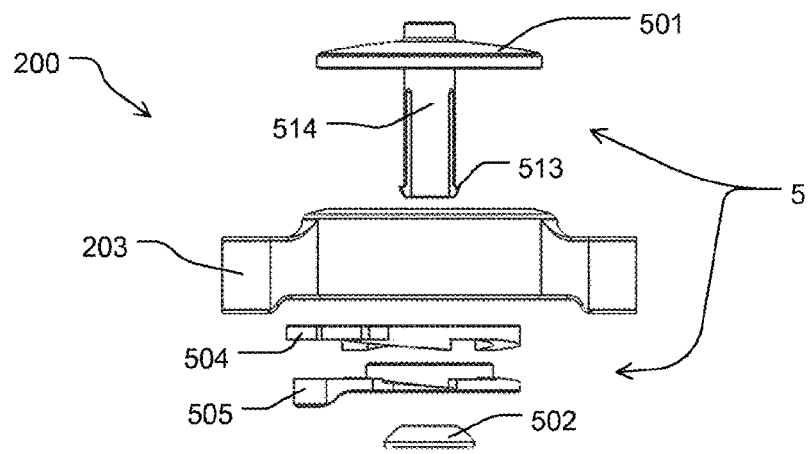

The space between the two wedge plates 504, 505 increases due to a counter rotation of the wedge plates 504, 505, whereby a force downwards is generated (with regard to the illustration in FIG. 13a). The joystick 501 is pulled down by this force. In this, the resistance between the joystick 501 and the receiving section 203 increases, so that a locking of the joystick 501 finally takes place.

FIG. 13a shows the joystick 501 with the optional guiding device 502 that may be used e.g. for a joystick 501 having a curved surface. For a joystick 501, which is not suitable for tilting relative to the main extension plane 204 (see FIG. 1) and which does not have a curved surface, a guiding device 502 is usually not required, but may be optionally provided.

The fitting and guiding of the joystick 501 is done in this embodiment through the fitting between the underside of the joystick 501 and the upper side of the receiving section 203. The first wedge plate 504 and the second wedge plate 505 may be rotated against each other such that the joystick 501 is releasably fixed relative to the receiving section 203 by clamping. In this, the guiding device 502 and/or the second wedge plate 505 is connected and fixed to the joystick 501 preferably in a force-fit manner.

Fixing and clamping using the wedge plates 504, 505 may advantageously be more uniform than, for example, by an alternative screw connection using a thread. The embodiment shown in FIGS. 13a-e may be advantageously easily manufactured.

Figures 13B, 13C:
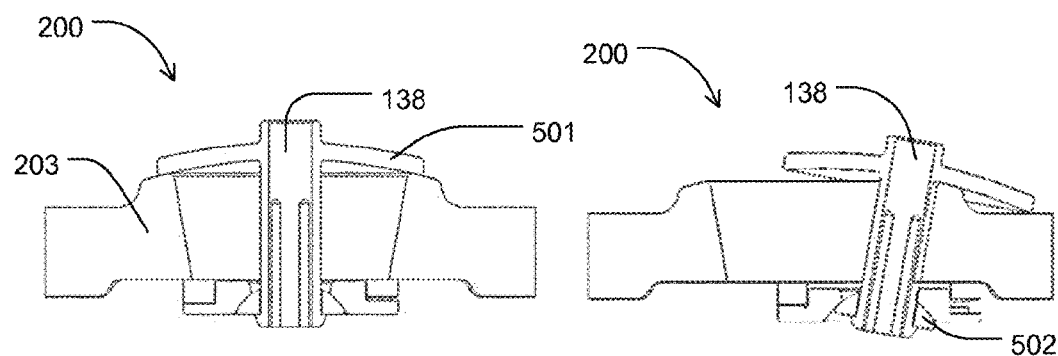

Shown in FIG. 13b is how the axis of the through opening 138 of the joystick 501 is arranged perpendicular to the plane of the upper side of the receiving section 203. This may be achieved with both a curved and a flat surface of the joystick 501.

Whereas in FIG. 13c the axis of the through-opening 138 is tilted relative to the mentioned plane. The tilting is achieved by the curved surface of the joystick 501 and by the curved surface of the guiding device 502.

Figures 13D, 13E:
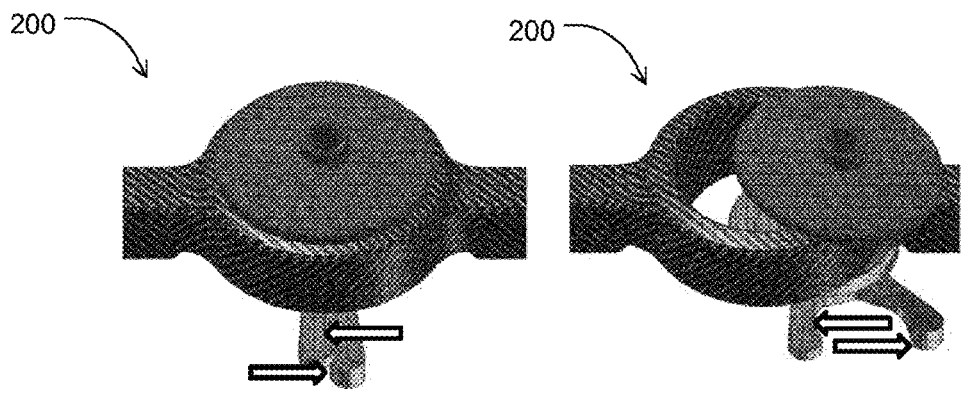

In FIGS. 13d-e a perspective view of the embodiment according to the present invention of positioning device module 200 is shown.

In an alternative embodiment of the positioning device module 200 as it is shown in FIGS. 14a-d, the positioning device module 200 comprises at least four parts. In this, said embodiment comprises a receiving section 203, and a at least three-part targeting device 5. The targeting device 5 comprises at least a joystick 501, a threaded plate 506 and an eccentric 507. The threaded plate 506 and the eccentric 507 have for example threads and may preferably therewith be coupled and fixed with each other. The joystick 501 may preferably be placed on the upper surface of the receiving section 203. By actuating the eccentric 507 the function of which is illustrated in FIG. 14b, the threaded plate 506 is pulled upwards and the joystick 501 is pushed downward. The interlocking takes place by the resistance between the joystick 501 and the receiving section 203.

The FIGS. 14c-d show the embodiment of FIG. 14a in the mounted state. The threaded plate 506 is exemplarily screwed with the eccentric 507.

FIG. 14b shows the eccentric 507 in an open position (left) and in an interlocked position (right).

In a sectional view in FIG. 14c (left) and in a perspective view (right), an interlocking position of the eccentric 507 (see arrow) is shown in which position the joystick and the threaded plate 506 are arranged perpendicular to a plane of the upper side of the joystick frame 503 and/or of the main extension plane 204. The curved surface of the threaded plate 506, which fits closely to the receiving section 203, and the curved surface of the joystick 501 allow an interlocking in a tilted arrangement of the joystick 501 and the threaded plate 506. The eccentric 507 is thus brought from its open position to its interlocking position (see arrow in FIG. 14d).

Figures 15A, 15B:
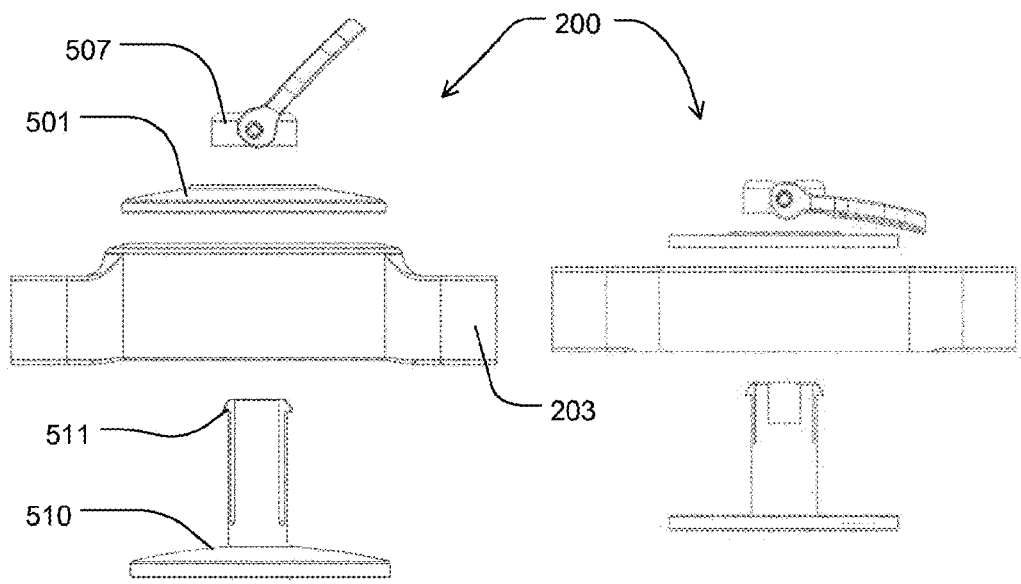

In FIG. 15a a latching plate 510 is shown as an alternative to the threaded plate 506 of FIG. 14a to be used as part of the targeting device 5. When using the latching device 510, latches 511 on the latching plate 510 serve the latching with the eccentric 507.

Figures 15C, 15D:
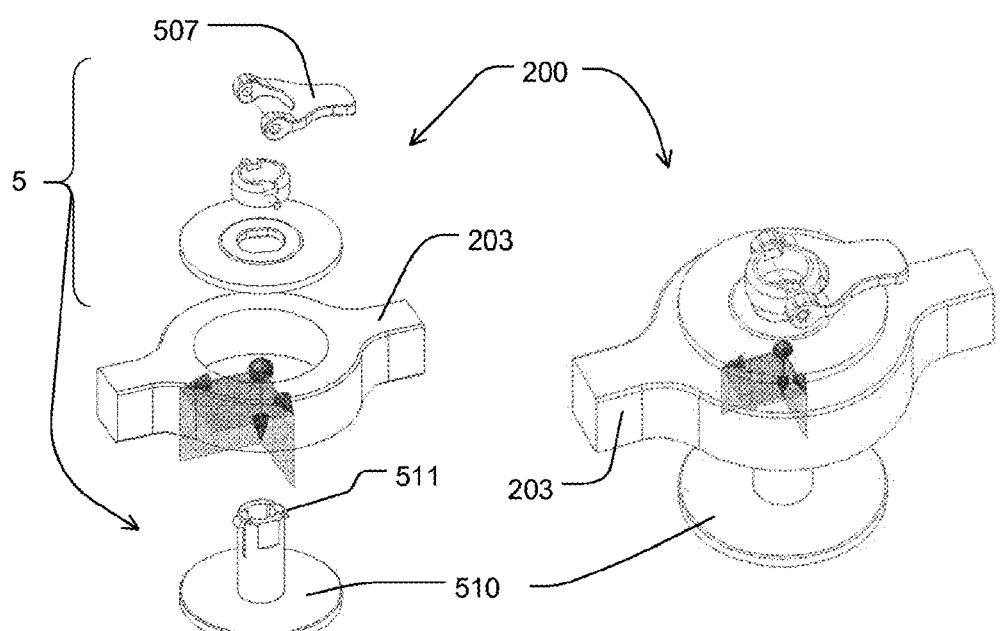

An embodiment of the positioning device module 200 comprising at least four parts is shown in FIGS. 15b-d. The embodiment comprises a receiving section 203. Further, the embodiment comprises a targeting device 5 with a latching plate 510, an eccentric 507 and a joystick 501. The latches 511 of the latching plate 510 may engage with the eccentric 507. In FIG. 15d, the two parts of the eccentric 507 are shown separately or separated. Unlike FIG. 15a, there is however no joystick 501 with a curved surface, but a joystick 501 with a flat surface. A joystick 501 having a flat surface may facilitate a parallel drilling since the joystick 501 cannot be accidentally tilted.

Figure 16A:
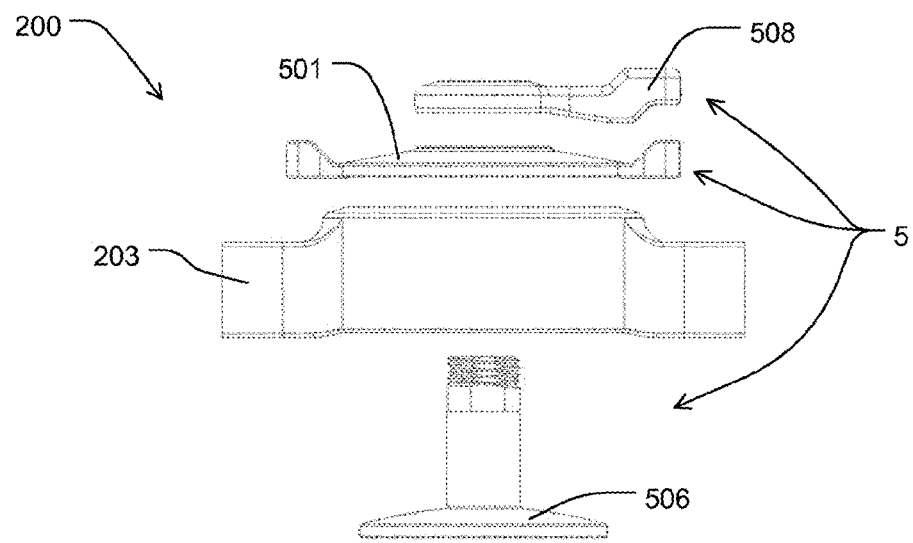
Figure 16B:
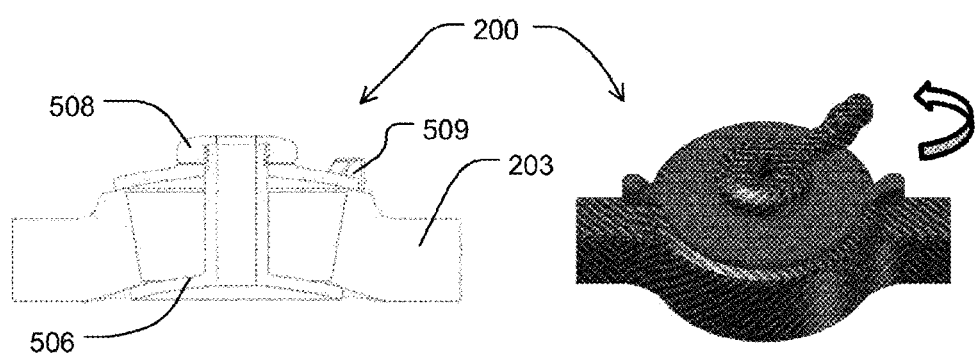
Figure 16C:
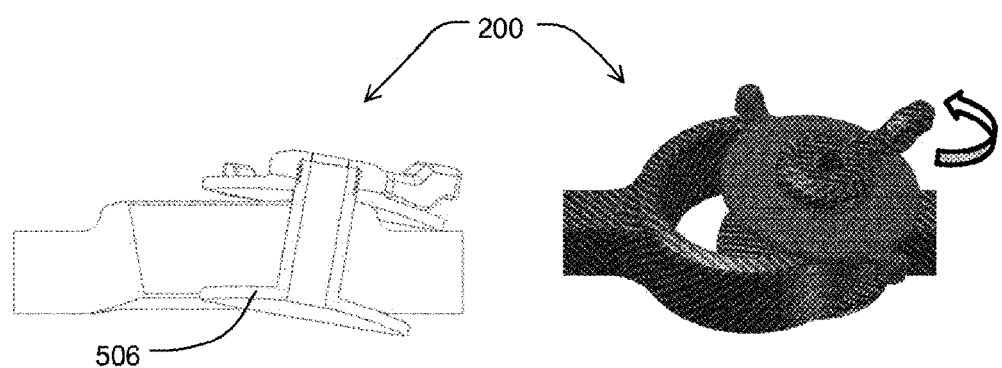

FIGS. 16a-c show a further embodiment of the positioning device module 200 comprising at least four parts. This embodiment comprises a receiving section 203 and a targeting device 5 which is designed at least in three parts as threaded plate 506, nut 508 and joystick 501. The threaded plate 506 and the nut 508 have threads and may therefore be coupled with each other. The joystick 501 may lie on the upper surface of the receiving section 203 and is optionally rotation proof relative to the threaded plate 506, in particular by a groove.

By a counter rotation of the nut 508, the threaded plate 506 may be pulled upwards and at the same time the joystick 501 may be pushed downward against the receiving section 203. Thereby, the joystick 501 may be kept by e.g. two latches 509 in order to prevent a co-rotation of the joystick 501. The interlocking may be achieved by the resistance between joystick 501 and receiving section 203.

FIG. 16b shows an interlocking of the threaded plate 506 and the joystick 501 being perpendicular to the surface of the receiving section 203 fitting closely to the joystick 501. Whereas FIG. 16c shows a tilted interlocking. For the tilted interlocking, a joystick 501 and a threaded plate 506 having a curved surface are used. For the perpendicular interlocking, a threaded plate 506 and a joystick 501 having a flat surface may be alternatively used as well.

Figure 17:
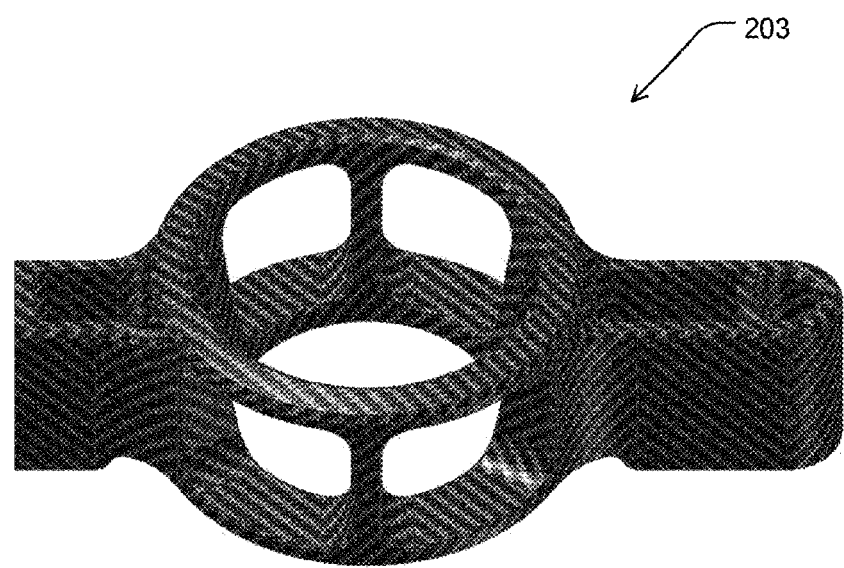
FIG. 17 shows an embodiment of the receiving section according to the present invention with a possible manufacturing variant or variation.

FIG. 17 shows a production variant for the receiving section 203. The receiving section may be produced e.g. by injection molding, as shown in FIG. 7. Alternatively, the reception section 203 may be spanned by a generative production process (e.g. Rapid prototyping, 3-D-Printing), or by another process.

The positioning device modules 200 shown in FIGS. 13 to 17 are suitable in some embodiments for being fixed on an extension device 401 and/or for being directly or indirectly fastened at a guiding bow 1.

Figure 18:
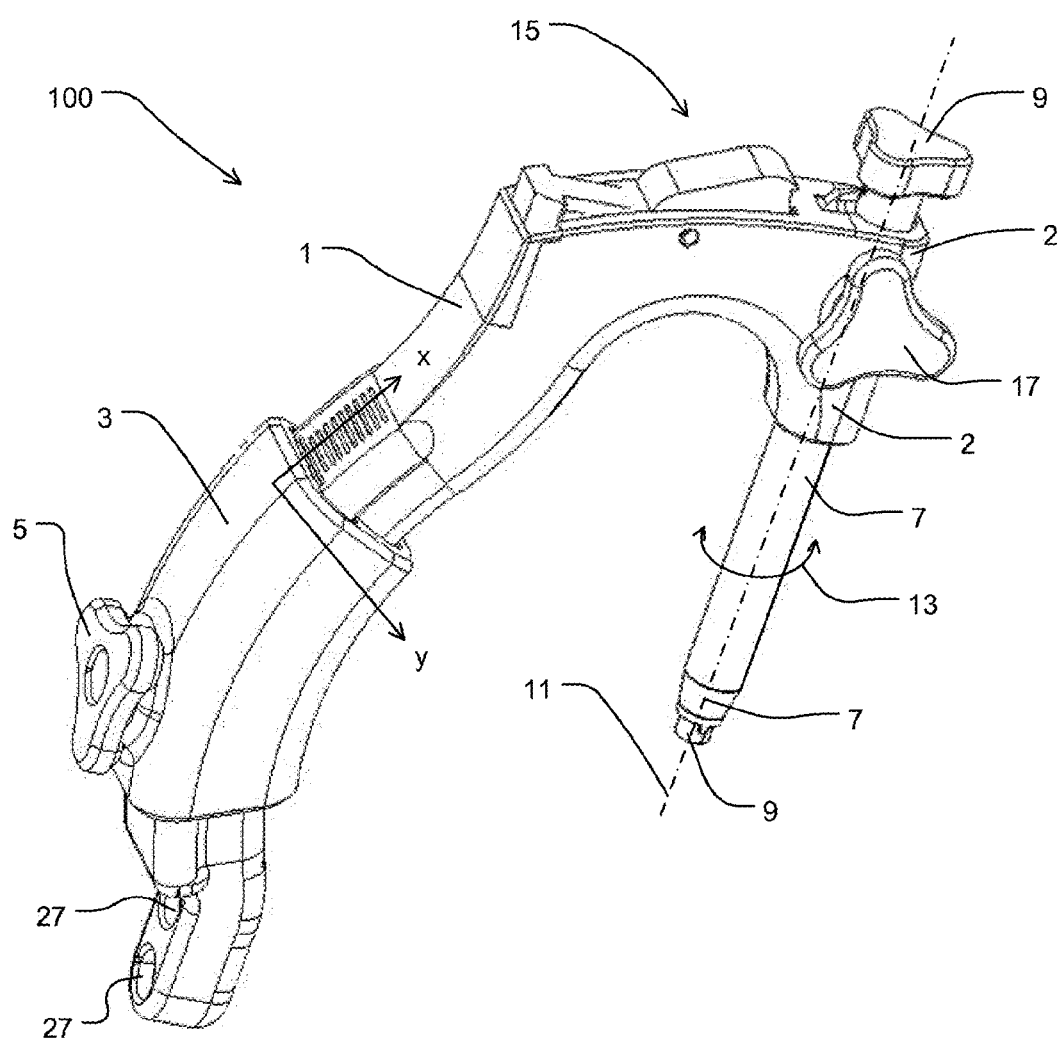
FIG. 18 shows a positioning device according to the present invention of a first exemplary embodiment in a perspective view.

FIG. 18 shows a perspective view of a first exemplary embodiment of a positioning device 100 according to the present invention, obliquely from the top. The positioning device 100 comprises a guiding bow 1 with a sleeve guide 2, an adjusting device 3 and a targeting device 5, a sleeve 7 and a guiding device 9.

The guiding bow 1 receives the sleeve 7 in the sleeve receptacle 2 and can be shifted or moved relative to the sleeve 7 about a longitudinal axis 11 of the sleeve 7 and/or can be rotated about the longitudinal axis 11 in the circumferential direction 13 of the sleeve 7. The sleeve 7 preferably comprises a sliding guide (or predetermined pathways) for the sliding or rotating of the guiding bow 1 (see FIG. 22). Along this sliding guide 29, there are optional positions given (see FIG. 22), at which the guiding bow 1 may be snapped-in preferably by means of a snap-in arrangement 15.

If, like in the example of FIG. 18, a snap-in arrangement 15 is provided then it is possible in certain embodiments according to the present invention, after a completed snap-in, to manually fix the guiding bow 1 on or at the sleeve 7 by means of a fixing screw 17 or by other fixation means; or the guiding bow 1 may be prevented from rotating further and/or from moving or sliding in a longitudinal direction relative to the sleeve 7. After having been fixed, the guiding bow 1 is positioned in the final position in order to secure an intramedullary nail by an interlocking screw (see FIG. 19).

If such fixation is provided, then it is done for example through frictional connection or form-fit between the fixing screw 17 and the sleeve 7.

The optionally provided adjusting device 3 is movable in x-direction along the guiding bow 1. After the final position of the adjusting device 3 has been reached through moving, the adjusting device 3 may be secured or fixed and/or clamped by a frictional connection on the guiding bow 1 by the targeting device 5, which, in this embodiment, is exemplarily also a differently designed fixing screw, or by another fixation device. For this purpose, the targeting device 5 preferably comprises a form which is easy to grasp, e.g. the triangular form shown in FIG. 18, so that it can be manually fixed.

The guiding device 9 has an opening (not shown in FIG. 18) at its upper end (referring to FIG. 18). It also has a further opening at its lower end, so that it offers or forms a continuous cavity for receiving a tool 55 (not shown in FIG. 18, see FIG. 30), for locking or interlocking the intramedullary nail 19 (also not shown in FIG. 18) or for receiving other objects. The longitudinal axis of the guiding device 9 runs preferably parallel to the longitudinal axis of sleeve 7, in which the guiding device 9 is received, or becomes identical to the longitudinal axis 11 of the sleeve 7.

In addition, positioning aids 27 may be provided for positioning interlocking screws at the positioning device 100.

Figure 19:
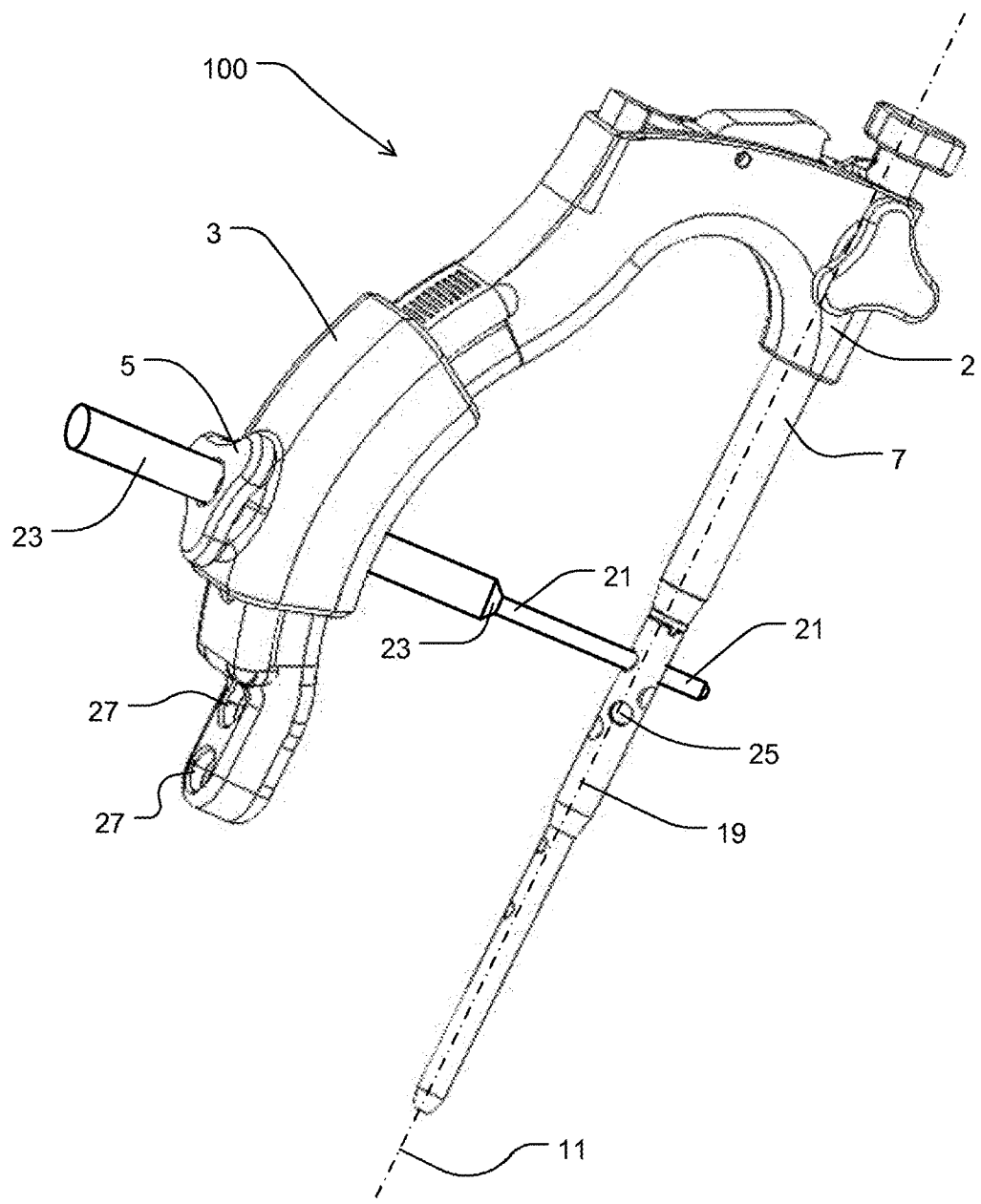
FIG. 19 shows the positioning device according to the present invention of FIG. 18 having an intramedullary nail, an interlocking screw and an instrument for inserting the interlocking screw.

FIG. 19 shows the positioning device 100 of FIG. 18 according to the present invention with an intramedullary nail 19, an interlocking screw 21 and an instrument 23 for inserting the interlocking screw 21. The instrument 23 is guided through the targeting device 5 and in the present example also through at least one section of the guiding bow 1.

Prior to inserting or screwing the interlocking screw 21 into the intramedullary nail 19, the guiding bow 1 may, as already described in FIG. 18, be moved along the longitudinal axis 11 and/or may be rotated about the latter in the circumferential direction of the sleeve 7. Furthermore, the adjusting device 3 may be moved along the guiding bow 1 in x-direction. This positioning (moving and rotating) is continued until an alignment on a targeted opening or a through-opening 25 in the intramedullary nail 19 is achieved and the interlocking screw 21 can be fixed in the intramedullary nail 19 and in a long bone surrounding the intramedullary nail 19 (not shown in FIG. 19). The positioning device 100 according to the present invention advantageously makes it possible to continue with this positioning of the interlocking screw 21 (and if appropriate further interlocking screws 21) after inserting the intramedullary nail 19 into the long bone, and thereby aiming at or heading for different through-openings 25 by the targeting device 5, until, in the view of the user, an optimum positioning of the one or more interlocking screws 21 has been achieved.

In addition, further interlocking screws 21' may in turn be screwed through the positioning aids 27, or by means thereof, into the intramedullary nail 19. These positioning aids 27 do not offer any possibilities for positioning along the longitudinal axis of the guiding bow 1 and thus do not offer a fixed, predetermined, possibly also perpendicular (relative to the longitudinal axis 11) or angled positioning of the interlocking screws 21 into the intramedullary nail 19. These positioning aids 27 may be referred to as so-called immobile or fixed target bores for rather distal interlocking screws 21'.

Figure 20:
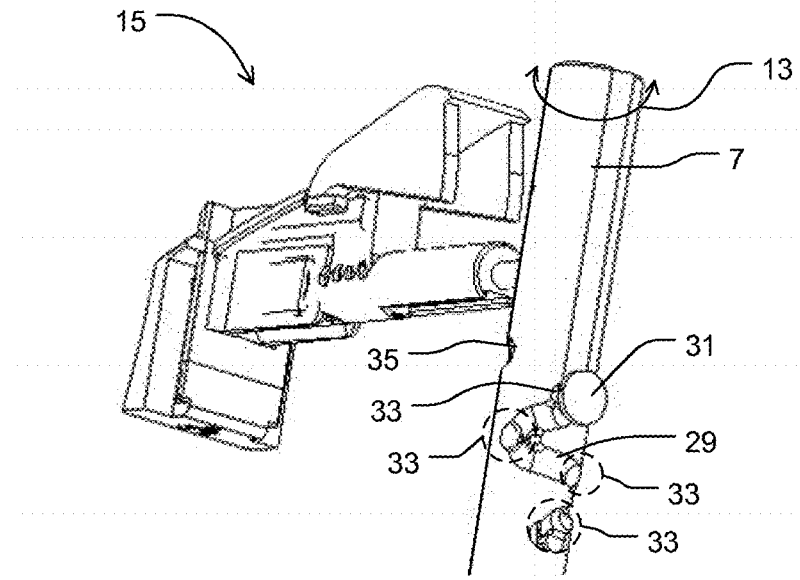
FIG. 20 shows a section of the positioning device according to the present invention having a sleeve and a sliding guide in the sleeve, as well as a snap-in arrangement.

FIG. 20 shows an inner section of the positioning device 100 according to the present invention with a sleeve 7 and a sliding guide 29 in or on the sleeve 7, and the snap-in arrangement 15. A cover covering the components in FIG. 20 during use of the positioning device 100, which cover is part of the guiding bow 1, is not illustrated in FIG. 20, however in FIG. 21, for the sake of clarity.

A guide step 31 (or pin), which is illustrated as a single part in FIG. 20 in a simplified manner, however is integrated into the guiding bow 1 and is part of the sleeve guide 2, allows through its engagement in the sliding guide 29 of the sleeve 7 a form-fit connection between the guiding bow 1 or the sleeve guide 2 and the sleeve 7. The guiding bow 1 is guided in or along the sliding guide 29 by the guide step 31.

Alternatively, the guide step 31 may be integrated into the sleeve 7 or connected thereto. In this case the sliding guide 29 may be integrated into the sleeve guide 2 (see FIG. 21).

The sliding guide 29 is straight in an upper part thereof (referring to the illustration of FIG. 20, i.e. between the upper end of the sleeve 7 and the guide step 31). By this straight sliding section, the guiding bow 1 is introduced into the sleeve 7 during the assembly of the positioning device 100 according to the present invention (or vice versa).

Alternatively, the guiding bow 1 may also be connected to or mounted on the sleeve 7 differently. For example, the outer diameter of the sleeve 7 in the upper area (above the sliding guide 29) could be smaller by twice the depth of the straight groove of the sleeve 7 than the outer diameter shown in FIG. 3 so that the guide step 31 can be put on the sleeve 7 over the entire circumference at the upper end thereof.

The sliding guide 29 may be designated as helical groove in a lower part thereof. In the lower area, the sliding guide 29 is not, or substantially not, straight, but rather wound, twisted, looped or the like.

The guiding bow 1 is therefore during its use guided or at least limited in a predefined path by the sliding guide 29. The guiding bow 1 may thus be moved only along the path indicated by the sliding guide 29 or limited therefrom relative to the sleeve 7 and/or may be slid and/or turned and/or rotated only into predetermined positions.

Guiding the guide step 31 into the sliding guide 29 may also be referred to as a form-fit tongue and groove connection.

Extensions 33 are provided in the example of FIG. 20 at the curved or bent points along the sliding guide 29, and as part of the latter. These may optionally be groove-like shaped. Their longitudinal axis extends preferably substantially or exclusively in the circumferential direction 13 of the sleeve 7, respectively. These extensions 33 mark or code for so-called snap-in positions 35 on the opposite side of the sleeve 7 in circumferential direction 13, into which a bolt or snap-in pin 39, described below, may be snapped in or engaged. Snap-in positions 35 may be referred to as long holes in circumferential direction 13. The snap-in positions 35 and their function are described in more detail in FIG. 22. The structure and the function of the snap-in arrangement 15 are also described in more detail in FIG. 22.

Figure 21:
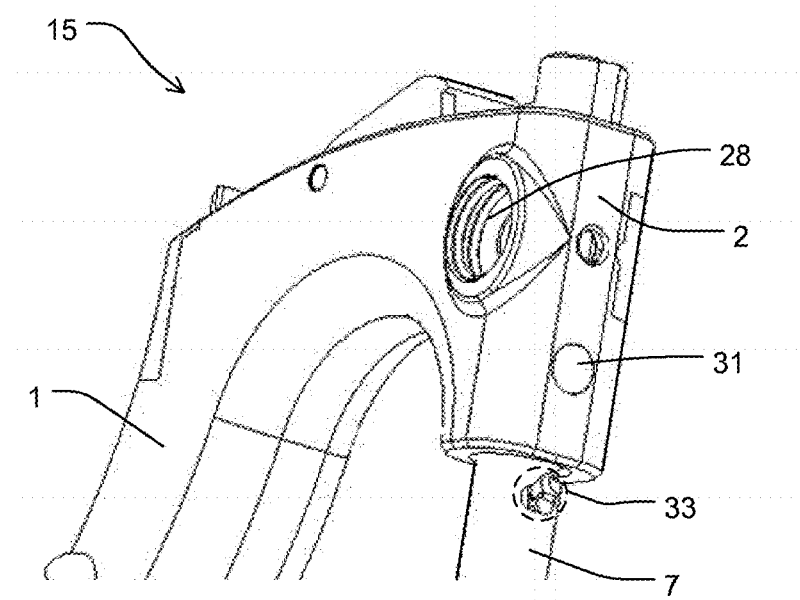
FIG. 21 shows the section of the positioning device according to the present invention of FIG. 20 with a section of a guiding bow.

FIG. 21 shows the section of the positioning device 100 of FIG. 20 according to the present invention being inserted into the upper section of the guiding bow 1. In this view, the guide step 3131 is integrally arranged in the guiding bow 1. The sleeve 7 is received into the receiving section of the guiding bow 1 for the sleeve 7, the sleeve guide 2. The sliding guide 29 is concealed by this; only the lowest, groove-shaped extension 33 is recognizable or seen.

Furthermore, FIG. 21 shows an inner thread 28 with a conical step for receiving the fixing screw 17 (see FIG. 18).

Figure 22:
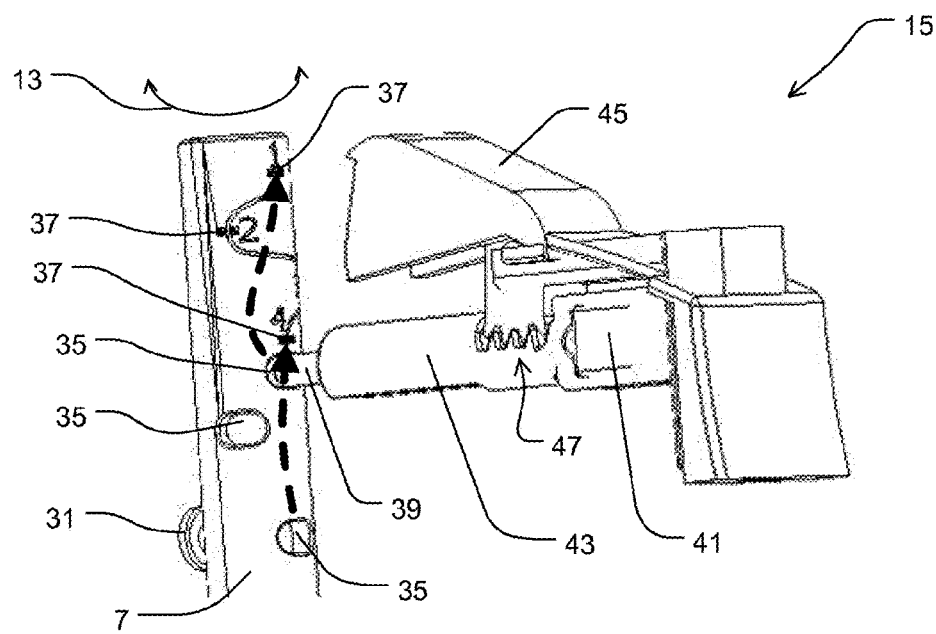
FIG. 22 shows in a further view the section of the positioning device of FIG. 20 according to the present invention having several snap-in positions and markings for position control.

FIG. 22 shows the section of the positioning device 100 of FIG. 20 according to the present invention in a further view. A plurality of snap-in positions 35 as well as markings for position control 37 can be seen. The view in FIG. 22 is rotated about 180 degrees in circumferential direction 13 relative to the view of FIG. 20 and FIG. 21.

The snap-in positions 35 correspond to the groove-shaped extensions 33 of the sliding guide 29 (see FIG. 20) and to the markings for position control 37 ("1", "2" and "4", the position "3" is concealed and not visible). For example, the marking "1" corresponds to the uppermost snap-in position which is, in FIG. 22, snapped-in with the bolt 39. This arrangement corresponds to the arrangement in FIG. 20 and FIG. 21, in which the guide step 31 is illustrated in the uppermost groove-shaped extension 33 of the sliding guide 29.

A locking of the snap-in arrangement 15, and thus of the guiding bow 1, into which the snap-in arrangement 15 is integrated and which is fixed by the locking with respect to the sleeve 7 or is restricted in further movement or rotation relative to the sleeve 7, occurs by a form-fit connection between the bolt 39 and the snap-in position 35 at a predetermined and predefined position of the sleeve 7. Prior to snapping-in the bolt 39 in a snap-in position 35, the bolt 39 may act on the sleeve 7 by a preload, in particular one achieved by a spring. The bolt 39 is then guided (frictionally) along the sleeve 7.

The snap-in position 35 is designed as a long hole but may also have other arbitrary shapes. In a long-hole shape of the snap-in position 35, the guiding bow 1 may move within the long hole in circumferential direction 13 of the sleeve 7. This so-called play of the guiding bow 1 in the sleeve 7 may facilitate the positioning and screwing of the interlocking screw 21 in the intramedullary nail 19. (see FIG. 19).

The markings for position control 37 ("1", "2", and "4") are visualization aids and thus orientation aids for the user of the positioning device 100 with respect to the direction of the rotation and/or the information about an angle of the guiding bow 1. The user may easily determine or retrace the location of the snap-in positions 35 with the aid of these markings 37.

The locking of the bolt 39 in one of the snap-in positions 35 occurs by the snap-in arrangement 15. In the snapped-in state, in which the bolt 39 is stuck in the snap-in position 35, preferably a tensioning device, e.g. a double leaf spring 41, such as that of FIG. 22, pushes on the bolt arrangement 43 (corresponds to an extension of the bolt 39) and interlocks it in the snap-in position 35. An undesired slipping out of the bolt 39 out of the snap-in position 35 may thereby be advantageously prevented. Decoupling of the snap-in position 35 is effected by, in particular manually, pressing down a lever 45 (or by actuating another suitable device) which pulls out or decouples the bolt arrangement 43 and thus the bolt 39 by means of, e.g., a gear connection 47. Following the decoupling, the guiding bow 1 can again be moved, relative to the sleeve 7, along the path of the sliding guide and may for example be positioned in a further snap-in position 35.

Figure 23:
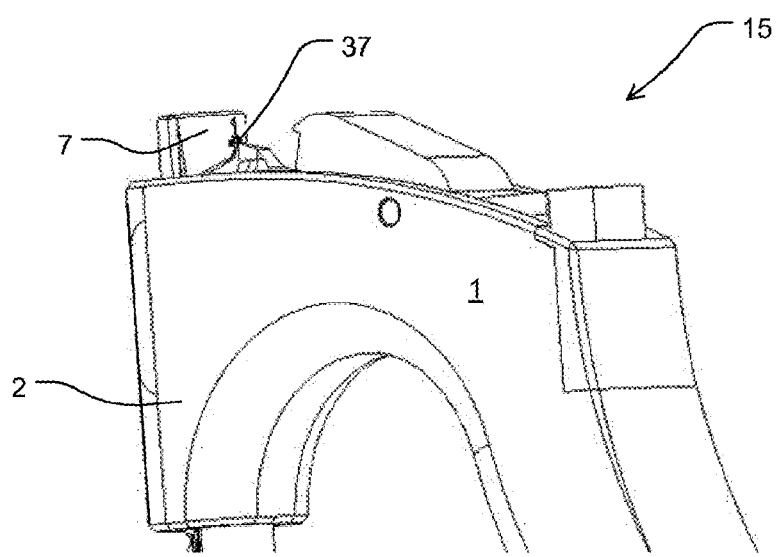
FIG. 23 shows the components of the positioning device of FIG. 22 according to the present invention with a section of a guiding bow.

FIG. 23 shows the components of the positioning device 100 according to the present invention which are seen in FIG. 22 concealed at least by a section of the guiding bow 1, which, as explained already in FIG. 21, conceals the snap-in arrangement 15.

In the present example, the guiding bow 1 conceals all four snap-in positions 35 such that the user is initially unable to recognize in which snap-in position 35 the bolt 39 is snapped-in. For this reason, the marking 37 for position control is optionally provided on the upper surface of the sleeve 7. It is seen in FIG. 23 that the bolt 39 is in the uppermost snap-in position 35, since the marking 37 shows or indicates "1", i.e. the uppermost marking 37, compare to FIG. 22.

Figure 24:
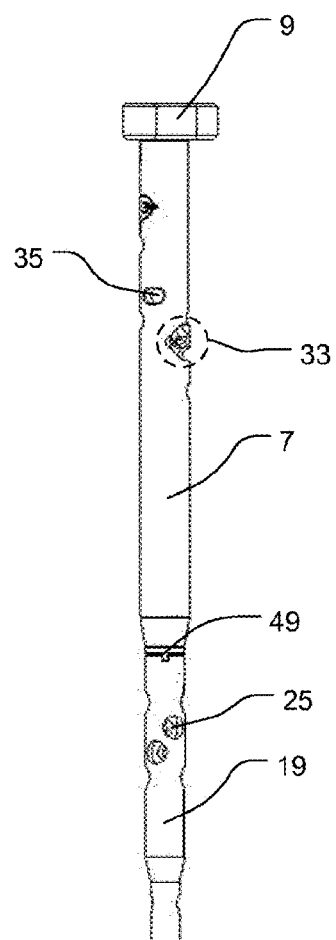
FIG. 24 shows a guiding device having a sleeve connected to an intramedullary nail.

FIG. 24 shows the guiding device 9 inserted into a sleeve 7, comprising a long hole and connected to the intramedullary nail 19.

The sleeve 7 is connected rotation-proof, by way of example, to the intramedullary nail 19 by two bars 49 (only the front bar 49 is visible in FIG. 24), wherein the bars 49 are inserted form-fit into the grooves of the intramedullary nail 19. This connection may be referred to as tongue and groove connection. Further, for fixing the sleeve 7 to the intramedullary nail 19, an optional thread 51 (external thread) is screwed into an inner thread of the intramedullary nail 19, if present, at the lower end of the guide device 9 (see FIG. 26). The intramedullary nail 19 is thus fixed (adapted) to the sleeve 7 in such a way that it can neither rotate nor slide. The location or position of the sleeve 7 relative to the intramedullary nail 19 is thus preferably fixed in both longitudinal and circumferential direction.

Figure 25:
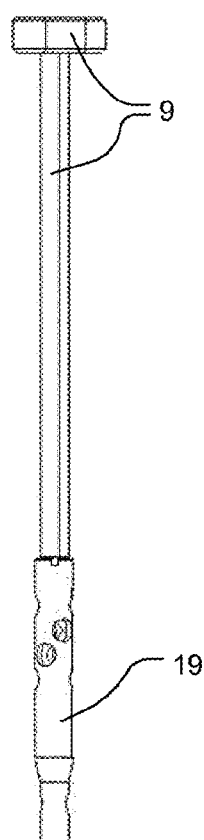
FIG. 25 shows the guiding device of FIG. 24 having the intramedullary nail, but without the sleeve.

FIG. 25 shows the guiding device 9 of FIG. 24 with only the intramedullary nail 19, without sleeve 7.

Figure 26:
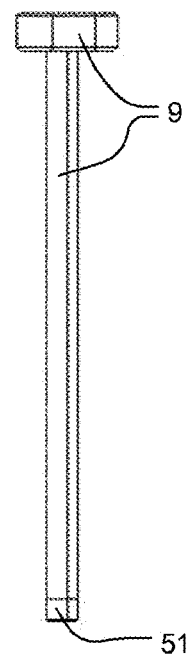
FIG. 26 shows the guiding device of FIG. 24.

FIG. 26 shows the guiding device 9 of FIG. 24 as a single part with the outer thread 51 at the lower end of the guiding device 9.

Figure 27:
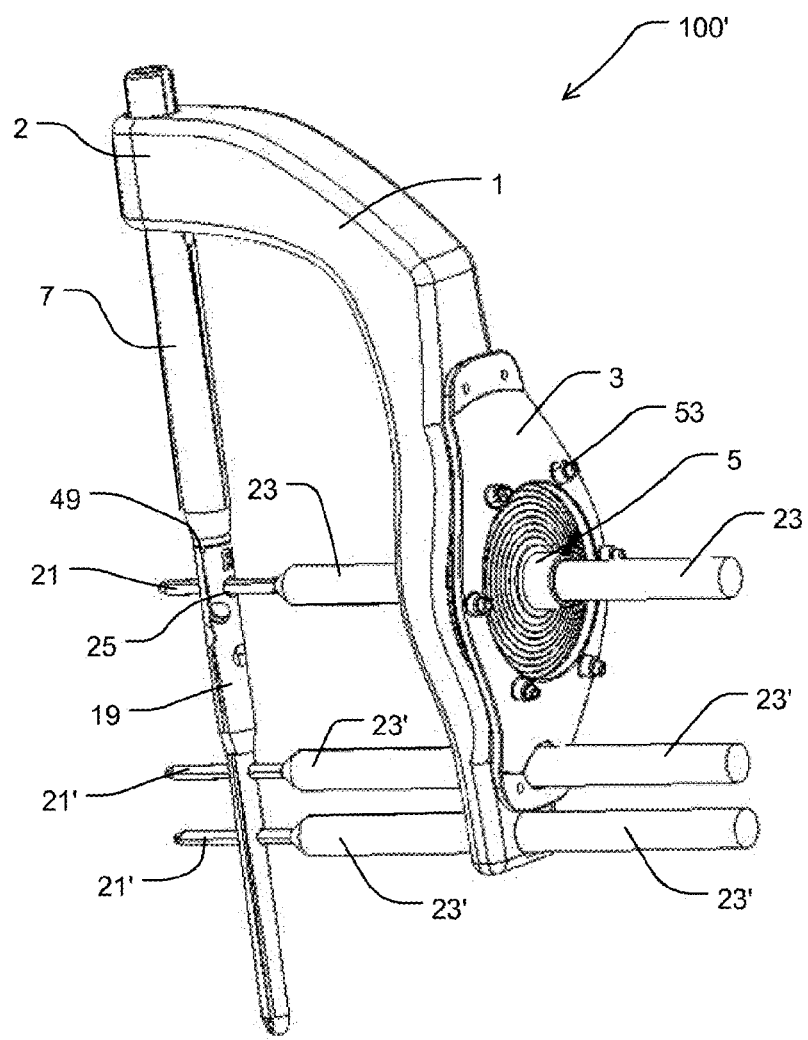
FIG. 27 shows a further embodiment of the positioning device according to the present invention, wherein the targeting device is arranged between the adjusting device and the guiding bow by means of a spring pin concept.

FIG. 27 shows a further embodiment of a positioning device 100' according to the present invention.

The adjusting device 3 is designed as a section of a spherical surface with a circular opening. The shape of the adjusting device 3 may likewise have a differently designed only optionally curved or straight upper surface instead of a spherical surface.

Figure 39:
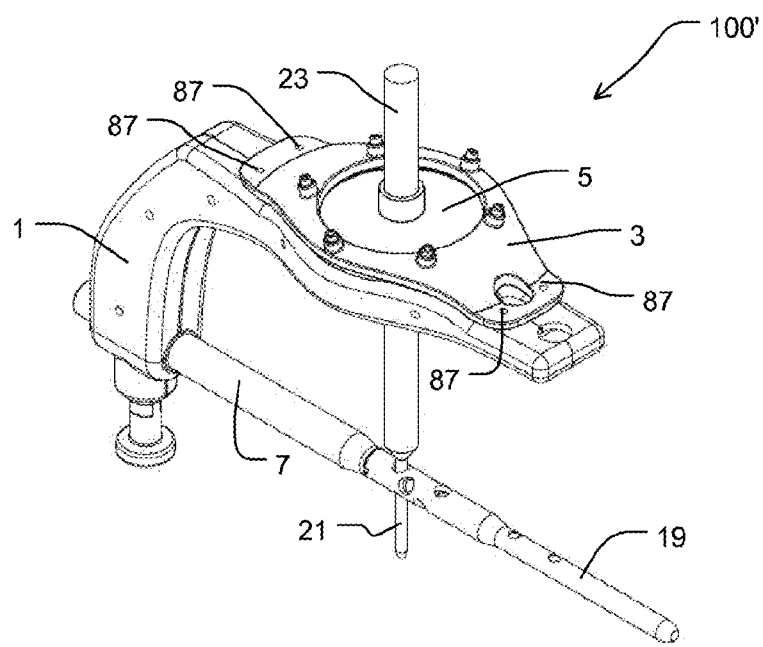
FIG. 39 shows the positioning device of FIG. 27 in a further view.
Figure 40:
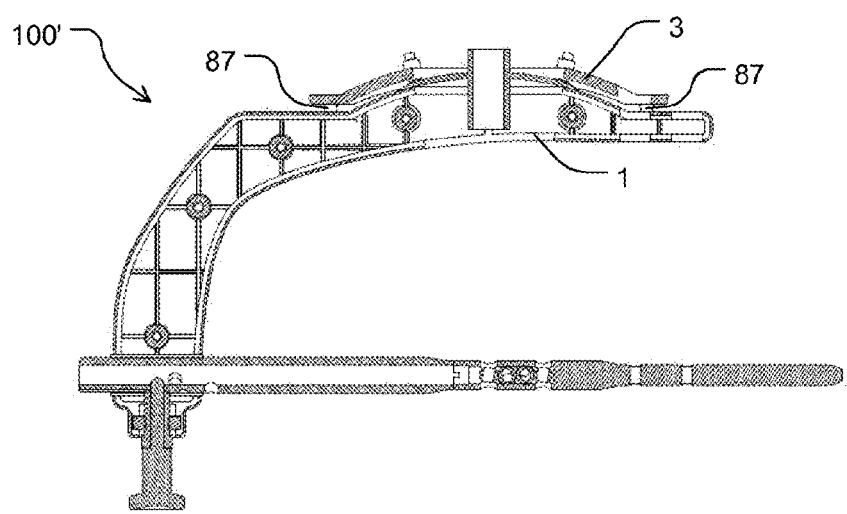
FIG. 40 shows a sectional view of the positioning device of FIG. 39.

The adjusting device 3 is fixed on the guiding bow 1 (the more detailed description of this fixation is explained in FIGS. 39 and 40).

The exemplary circular opening in a central or middle area of the adjusting device 3 is provided for guiding the targeting device 5 and the instrument 23 (which serves for inserting the interlocking screw 21). The longitudinal axis of the instrument 23 is perpendicular to the spherical surface. The extension of the longitudinal axis of the instrument 23 extends through the center of the bore or through-opening in the intramedullary nail 19.

The instrument 23 is guided into the targeting device 5. The targeting device 5 is optionally shell-like shaped with annularly concentrically arranged grooves, notches or protrusions about the middle guide of the instrument 23. The shell-like shaped targeting device 5 may be referred to as a middle shell, which, viewed in the radial direction, is arranged between the outer shell which corresponds to the adjustment device 3 and the inner shell which corresponds to the closely lying shell-like shaped surface of the guiding bow 1.

The targeting device 5, i.e. the middle shell, may be moved or slid between the inner and the outer shell. In this movement, optional pins 53, spring-mounted in radial direction, engage in the annular grooves or notches of the targeting device 5. Therewith a defined and exact positioning of the instrument 23, and thus of the interlocking screw 21, is possible. The distances between the grooves correspond to a specific and predetermined deflection of the targeting device 5, which may be indicated with an angle or in degrees number. In this exemplary embodiment of the deflection between two annular grooves corresponds to an angle or a number of degrees of one (1°). This principle or concept with spring-mounted pins 53, which engage into grooves, may be referred to as a spring-pin concept.

Figure 29:
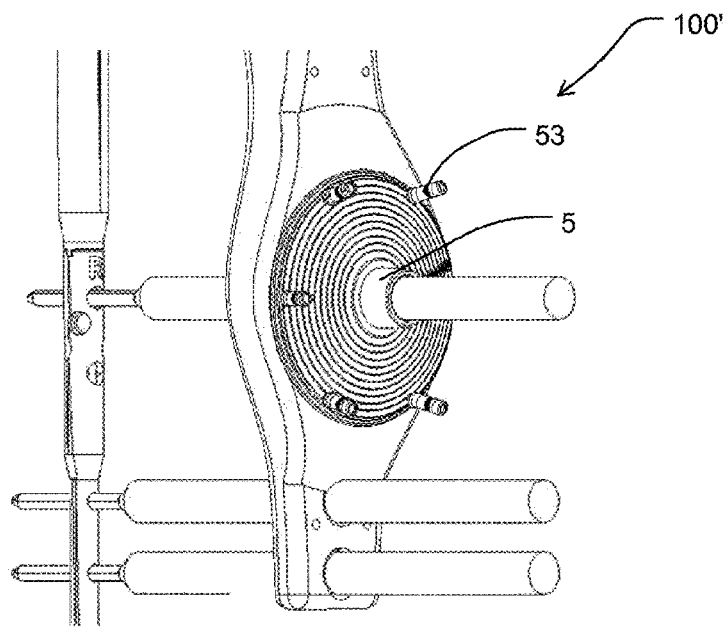
FIG. 29 shows the detail view of FIG. 28 without an outer shell of the adjusting device.

The arrangement of the radially spring-mounted pins 53, on the radial outer surface of the targeting device 5 is shown in FIG. 29, in which the adjusting device 3 (outer shell) has been removed for better clarity.

Figure 28:
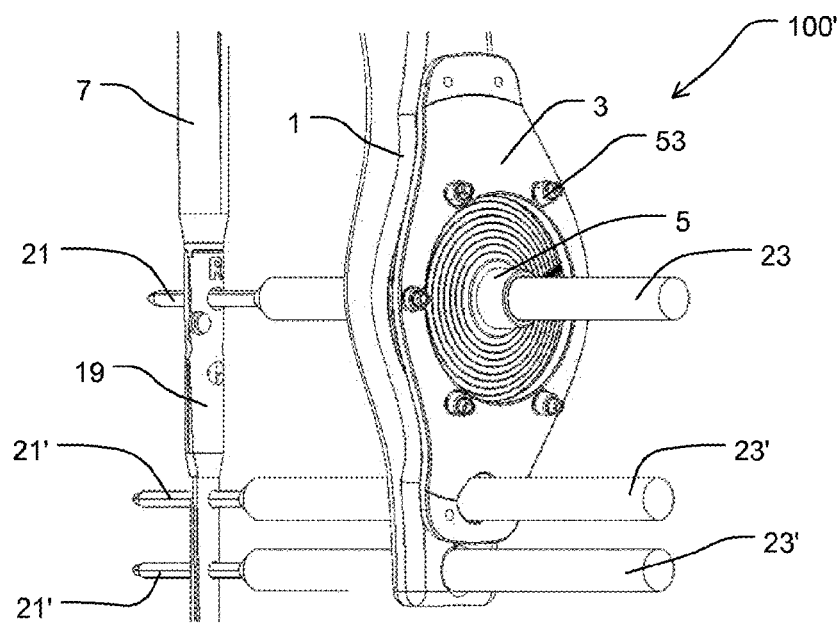
FIG. 28 shows a detail view of an adjusting device having a targeting device of the positioning device of FIG. 27.

The arrangement in FIG. 27 allows the instrument 23 (and thus the interlocking screw 21) to deflect by a desired or predetermined degree (or degree range), for example by ten degrees (10°) from the centrical initial position in the middle (this initial position is shown in FIGS. 27, 28 and 29 and is referred to as a zero-degree position (0°).

By an optional combined form-fit connection (between the pins 53 and the annular grooves of the targeting device 5) and a frictional connection (between the middle and the outer shell), a fixing of the position of the instrument 23 for screwing or positioning the interlocking screw 21 is, hence, rendered possible.

The targeting device 5 may optionally rest on a circular section of a structure which is arranged under the targeting device 5. In this way, it may be ensured that the targeting device 5 is guided at preferably a constant distance to a target point.

FIG. 28 shows a detailed view of FIG. 27 with the adjusting device 3 (outer shell), the targeting device 5 (middle shell), the guiding bow 1 (inner shell), the sleeve 7, the intramedullary nail 19 and the instrument 23 for inserting the interlocking screw 21. Furthermore, non-movable instruments 23' (the adjusting device 3 is not movable relative to the guiding bow 1) for interlocking or screwing of further interlocking screws 21' are illustrated.

FIG. 29 shows the view from FIG. 28 without the adjusting device 3 (outer shell) for illustrating the position of the pins 53 on the targeting device 5 (middle shell).

Figure 30:
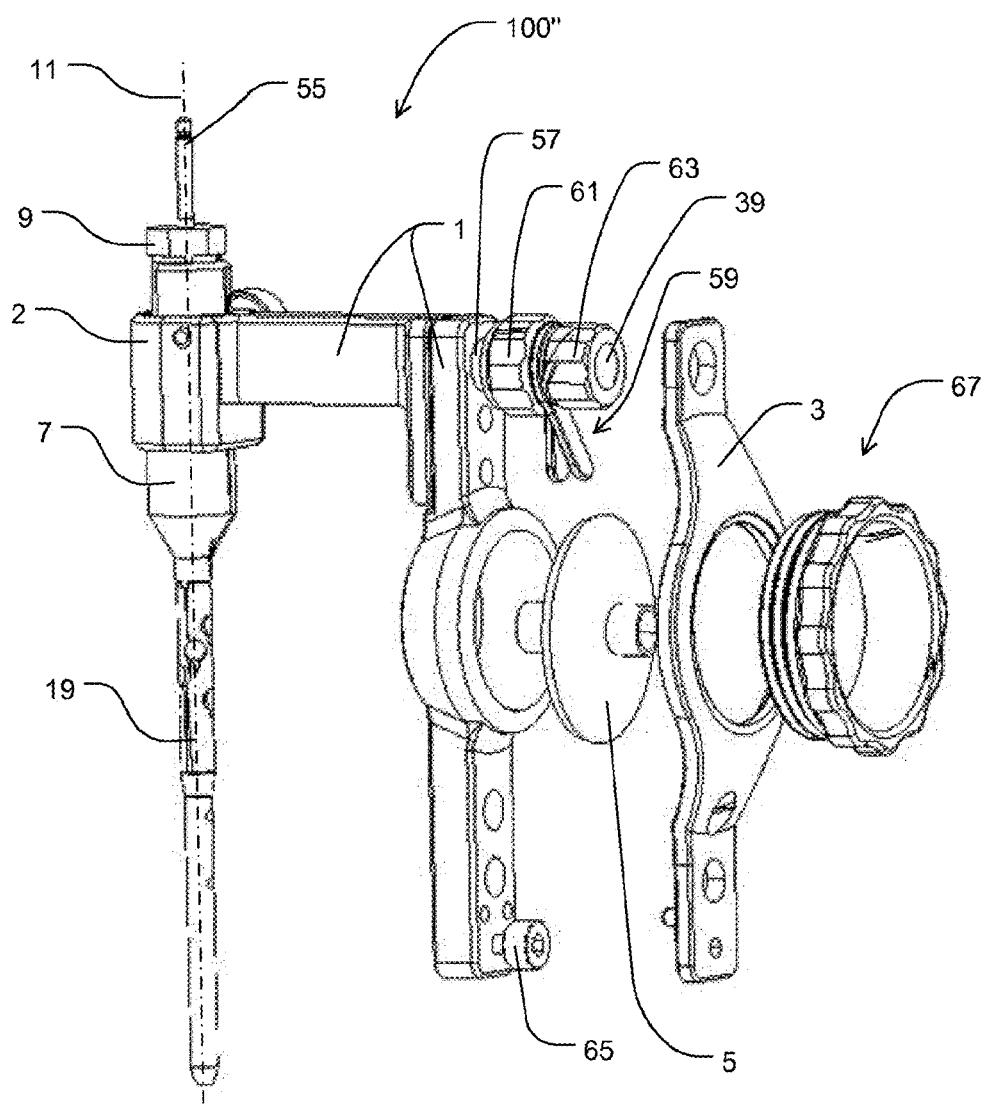
FIG. 30 shows a further embodiment of the positioning device according to the present invention.

FIG. 30 shows a further embodiment of the positioning device 100" according to the present invention.

The guiding bow 1 is halved in this embodiment. A first section (in FIG. 30, the left section) of the halved guiding bow 1 comprises the sleeve guide 2, is exemplarily straight and extends in this embodiment substantially perpendicular to the longitudinal axis 11 of the sleeve 7. The guiding device 9 is introduced into the sleeve 7, in which guiding device 9 the tool 55, for example a hexagon screwdriver, is guided along the longitudinal axis 11, e.g. for locking the intramedullary nail 19. Alternatively, other objects instead of the tool 55 may also be guided by the guiding device 9.

The first section is connected to a second section (in FIG. 30, the right section) of the guiding bow 1. The second section comprises the targeting device 5. The connection of the two sections may be achieved, e.g., by a bushing 57. The snap-in pin 39 (or bolt of the snap-in arrangement), which is concealed in FIG. 30 by the guiding bow 1 and is explained in more detail in FIG. 31 as a further snap-in arrangement 15', is guided in the connector 57. The snap-in pin 39 is actuated or moved preferably by at least one lever 59 or a differently designed arrangement. The lever 59 is shown in two different positions in FIG. 30. The function of the lever 59 is described in more detail in FIG. 31.

The second section of the guiding bow 1 comprises the adjusting device 3 as well as the targeting device 5, which are shown in FIG. 30 in an exploded view, i.e., in the non-assembled state. In the assembled state, the adjusting device 3 is connected, e.g. to the bushing 57 at the upper end (referring to the view in FIG. 30), as shown in FIG. 31.

The adjusting device 3 is connected to or fixed to, e.g. at the lower end thereof, the second section of the guiding bow 1 by a connecting screw 65.

The targeting device 5 is fixed between the adjusting device 3 and the second section of the guiding bow 1 by a so-called tension wheel 67.

Regarding the function of the targeting device 5, reference is made to the description of FIG. 27.

FIG. 31 shows the further snap-in arrangement 15' of the embodiment of FIG. 30.

The snap-in arrangement 15' is based on a magnetically supported fixing of the snap-in pin 39 into the snap-in position 35. The magnetic coupling is realized by a magnet or magnetic material, or presently by two magnets 61, 63 which may be arranged at the outer end of the snap-in pin 39 and which, facing each other, have different polarities. The first magnet 61 may be connected, e.g., to the bushing 57 and/or to the guiding bow 1. The second magnet 63 may be connected to the outer end of the snap-in pin 39. Using the lever 59, the two magnets may be pushed apart and thus will uncouple or pull out the snap-in pin 39 from the snap-in position. For this purpose, the lever 59 is pressed inwards in the direction of the arrow 60, so that the snap-in pin 39 and the magnet 63 are pushed outwards due to the angled or tilted lever 59.

FIG. 32 shows a further snap-in arrangement 15' with the snap-in pin 39, a handpiece 71, a spiral spring 69 and a screw 99. For assembling, the parts A and B are first introduced into the guiding bow 1 in the direction of the arrow. Then the parts D and E (snap-in pin 39, handpiece 71, spiral spring 69) are introduced into the guiding bow 1 in the direction of the arrow. Subsequently, the screw 99 (part E) is screwed into the guiding bow 1, thus fixing the snap-in pin 39, the handpiece 71 and the spiral spring 69 in the guiding bow 1. During this assembly step, the handpiece 71 has been pushed through the guiding bow 1, which is hollow inside, with the angular range. It then protrudes out of the guiding bow 1 with the angular range. In this snapped-in state, the spiral spring 69 is compressed and pre-stressed. For decoupling the snapped-in snap-in pin 39 out of the snap-in position 35 in the sleeve 7, the snap-in pin 39 is pulled outward by manually pressing the handpiece 71 into the guiding bow 1, the snap-pin 39 is pulled out of a snap-in position 35 and the spiral spring 69 is further compressed. After a new repositioning of the guiding bow 1, the snap-in pin 39 can be snapped-in back into one of the snap-in positions 35 of the sleeve 7 by returning the handpiece 71 inward and by relaxing the spiral spring 69 back to its initial state.

FIG. 33 shows a further snap-in arrangement 15' with a leaf spring 73 and a lever 75. As shown in FIG. 32, the leaf spring 73 is tensioned by pressing down the lever 75 and/or due to tensioning. Concurrently with the tensioning of the leaf spring 73, the snap-in pin 39 is pulled out of the snap-in position 35 and decoupled therefrom by means of the handpiece 71. After a new positioning of the guiding bow 1, the snap-in pin 39 can again be brought into a further snap-in position 35 in the sleeve 7 and locked therein.

Figure 34:
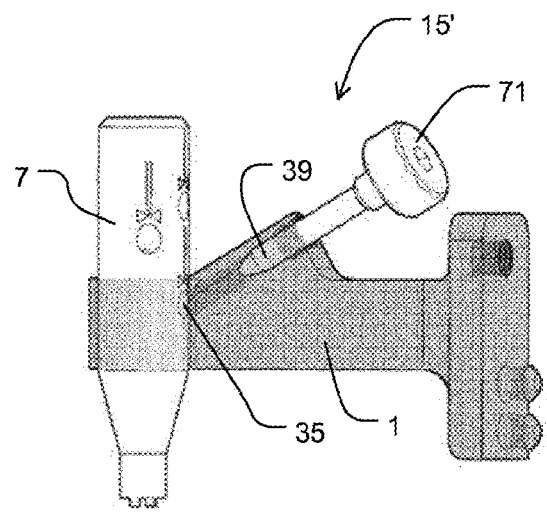
FIG. 34 shows a further snap-in arrangement having a snap-in pin for inserting the latter into the sleeve obliquely from above.

FIG. 34 shows a further snap-in arrangement 15' with a snap-in pin 39 (the snap-in pin 39 may be referred to as a plug-in bolt) which is inserted into a snap-in position 35 in the sleeve 7 obliquely from the top.

Figure 35:
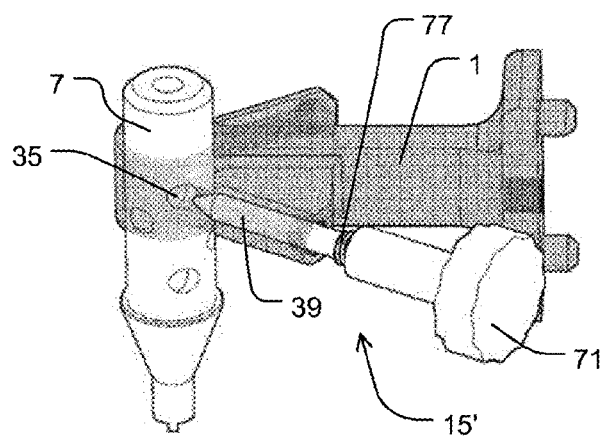

FIG. 35 shows a further snap-in arrangement 15 with a snap-in pin 39 for laterally inserting the latter into a snap-in position 35 of the sleeve 7. The snap-in pin 39 may be fixed after having been snapped-in by actuating or rotating the handpiece 71 and an optional thread 77.

FIG. 36 shows a halved targeting device 5 of the embodiment in FIG. 30. Two sections of the targeting device 5 maybe screwed together e.g. by a thread 79. The outer thread of the left section, in FIG. 32, of the halved targeting device 5 is screwed into the inner thread of the right section, in FIG. 32, of the targeting device 5.

Various advantages may be obtained by a halved targeting device 5. For example, a combination of different materials (higher strength of a bushing for guiding an instrument for inserting the interlocking device or the interlocking screw 23, 23'; see e.g. FIG. 19) or an increase of the strength of bending stiffness or rigidity of the targeting device 5.

FIG. 37 shows a side view of an adjusting device 3 with a snap-in device 81 for securing the adjusting device 3 at the guiding bow 1. The direction of the arrow shows the direction for closing, locking or snapping-in the adjusting device 3 on or at the guiding bow 1. The snap-in device 81 is in particular elastically deformed or bent during the snap-in process, so that the snap-in device 81 is hooked at the guiding bow 1 after having been snapped-in. For decoupling, the snap-in device 81 may be elastically bent up and opened.

In the decoupled state, the targeting device 5 may, e.g., be replaced or adapted.

FIG. 38 shows a further targeting device 5 with a hole arrangement 83 for an instrument 23 (see FIG. 39). Whereas the embodiments of the targeting device 5, e.g. in FIG. 28 or FIG. 29, in which the targeting device 5 comprises only one hole, wherein the targeting device 5 is movable three-dimensionally in a plurality of axes directions between the guiding bow 1 and the adjusting device 3, the targeting device 5 in FIG. 38 is rotatable only about axis (the middle axis of the cylindrical targeting device 5). This limitation of movement may be advantageous, for example, in order to limit the angles for an instrument 23 in the respective holes and thus to limit the angles for placing the interlocking screws 21 by the positioning device 100.

The targeting device 5 may be fixed by a fixing screw 85.

FIG. 39 shows a further view of the positioning device 100' of FIG. 27 with the guiding bow 1, the adjusting device 3, the sleeve 7, the intramedullary nail 19, the targeting device 5 as well as the instrument 23 for inserting the interlocking screw 21. The annularly arranged grooves shown in FIG. 27 are not shown in the simplified illustration of FIG. 39.

The adjusting device 3 is connected to the guiding bow 1 by (for example) four (optional) point-shaped fixations.

FIG. 40 shows the positioning device 100' of FIG. 39 in a sectional view.

Figure 41:
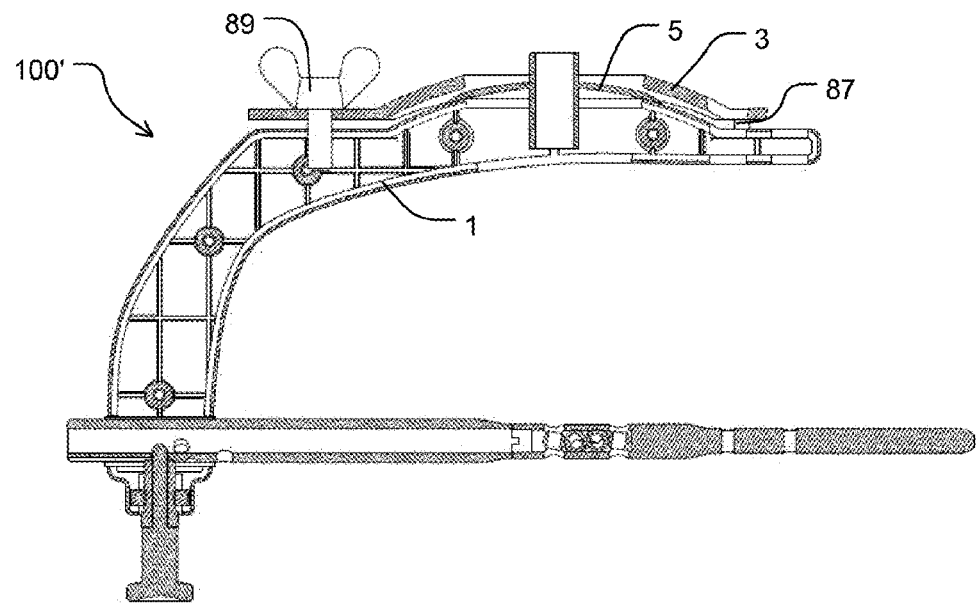
FIG. 41 shows a sectional view of the positioning device of FIG. 39 with a flap concept for securing the adjusting device on the guiding bow.

FIG. 41 shows the positioning device 100' of FIG. 39 in a sectional view with a flap concept for fixing the adjusting device 3 on the guiding bow 1. In this exemplary embodiment, the flap concept comprises only two (or optionally only one) point-shaped fixation 87 on one side of the adjusting device 3. On the opposite side, the adjusting device 3 is connected to the guiding bow 1 by a wing screw 89 (or an eccentric, a snap hook or the like). By means of this connection, the adjusting device 3 is pressed or pushed into the guiding bow 1 so that the targeting device 5 is clamped or fixed between the adjusting device 3 and the guiding bow 1.

By means of this flap concept, it is exemplarily advantageously possible to replace the targeting device 5.

Figure 42:
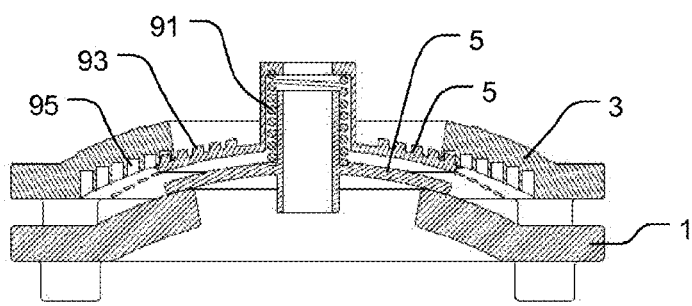
FIG. 42 shows the targeting device, which is movably arranged between the adjusting device and the guiding bow by means of a spring concept.

FIG. 42 shows a targeting device 5, which is movably arranged by a spring concept between the adjusting device 3 and the guiding bow 1. In this embodiment, the targeting device 5 comprises two sections or shells, between which a spiral spring 91 is arranged. The upper section (with reference to FIG. 42) is pushed upward by the spiral spring 91. As a result, the protrusions 93 arranged on the upper side rest or snap into bores 95 (or grooves) on the bottom side of the adjusting device 3. For example, ten protrusions 93 and bores 95 may be arranged on the upper or bottom side, respectively.

Figure 43:
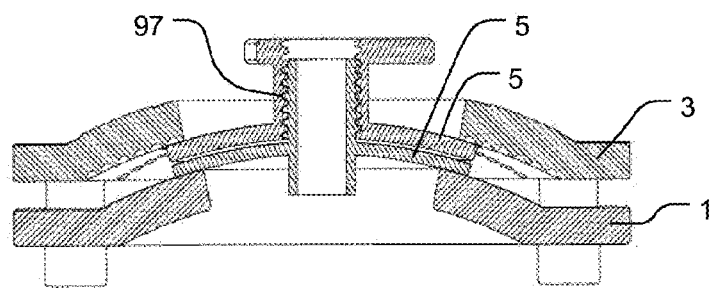
FIG. 43 shows a targeting device, which is movably arranged between the adjusting device and the guiding bow by means of a thread concept.

FIG. 43 shows a further targeting device 5, which is movably arranged by means of a thread concept between the adjusting device 3 and the guiding bow 1. By means of a thread 97, the upper shell of the targeting device 5 may be pressed and fixed against the bottom side of the adjusting device 3 and the bottom side of the lower shell of the targeting device 5 may be pressed and fixed against the upper side of the guiding bow 1.

Figure 44:
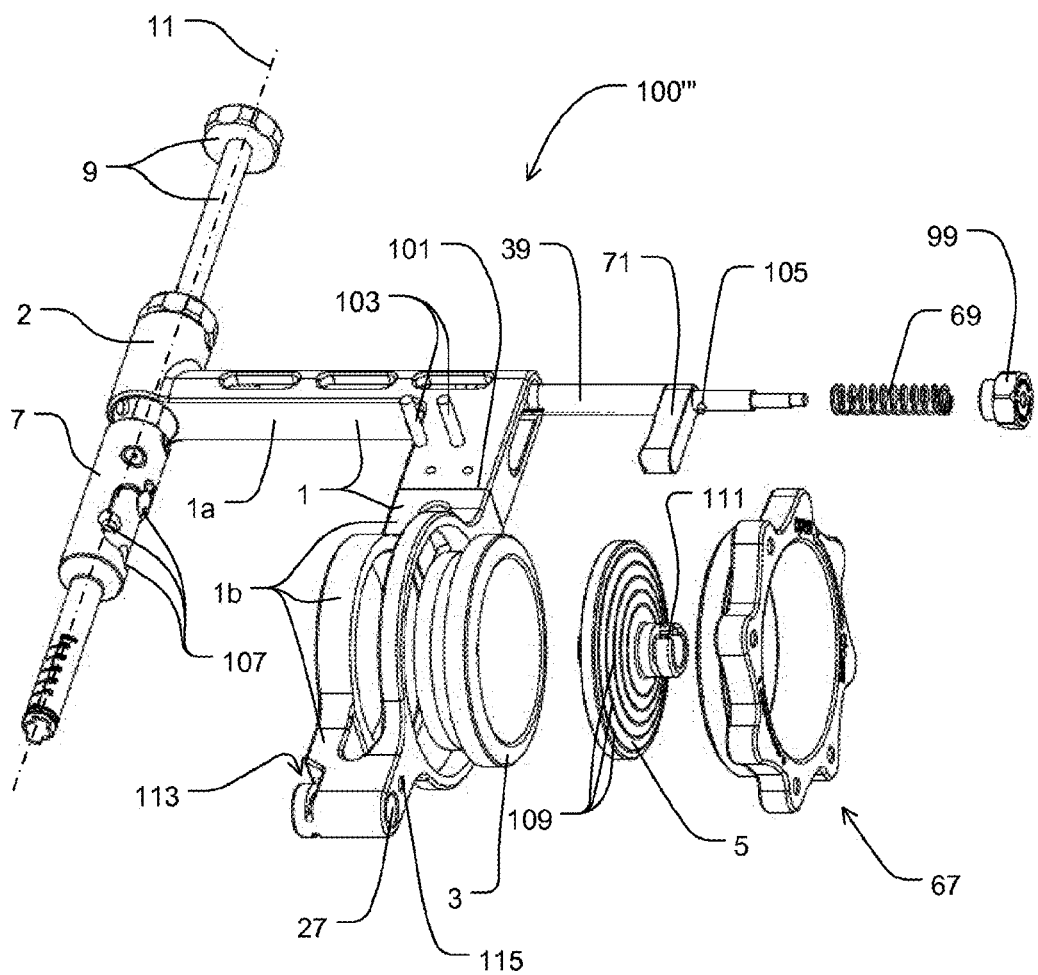
FIG. 44 shows a further embodiment of the positioning device according to the present invention.

FIG. 44 shows a further embodiment of the positioning device 100''' according to the present invention.

The guiding bow 1 is halved. A first section 1a (in FIG. 44 top) is connected to the sleeve guide 2, in particular releasably. Alternatively, the connection may be a non-releasable firmly bonded connection, for example a soldered connection, a welded connection or an adhesive connection.

The firmly-bonded, integral connection may be a one-piece component, e.g., produced by casting and/or machining. The first section 1*a* may be produced by a generative production method, e.g., by means of a laser sintering method or a rapid prototyping method.

A second section 1*b* of the guiding bow 1 may be produced as one part or multiple-part.

The first section 1*a* and the second section 1*b* may be connected to each other by means of a form-fit or a firmly bonded connection, at an interface 101. For example, the second section 1*b* may be form-fit or positively pushed into a hollow end section of the first section 1*a* by a step. Subsequently, this form-fit connection may be fixed and secured by means of one or several bolts 103 (the bolts 103 may be dowel pins). This form-fit connection may be additionally secured by an adhesion. An adhesion may be advantageous in order to ensure a play-free connection even after prolonged use and multiple mechanical stresses. A play-free connection may be important for a therapeutic success due to the exact positioning of intramedullary nails by the positioning device 100''' according to the present invention.

The mounting of the snap-in pin 39, the handpiece 71, the spiral spring 69 and the screw 99 with the guiding bow 1 takes place as described in FIG. 30. In addition, in the embodiment in FIG. 44, a small pin 105 (the pin 105 may be referred to as pin) is fastened or connected to the snap-in pin 39. The spiral spring 69 and the pin 105 are designed such that the spiral spring 69 is usually first mechanically elastically deformed in order to allow it to be moved or pushed through the pin 105 on the snap-in pin 39. (In FIG. 44 the spiral spring 69 is moved to the left over the pin 105 in the direction of the handpiece 71). In this way, the spiral spring 69 cannot separate independently from the snap-in pin 39 without renewed elastic deformation. This has the advantage that sterilization of the arrangement may be carried out without disassembling the spiral spring 69.

Figure 46:
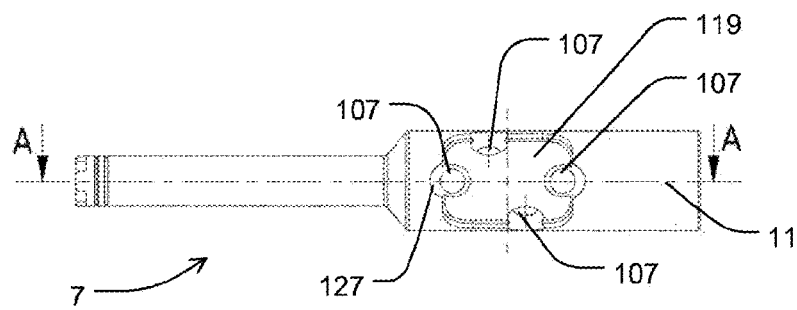
Figure 47:
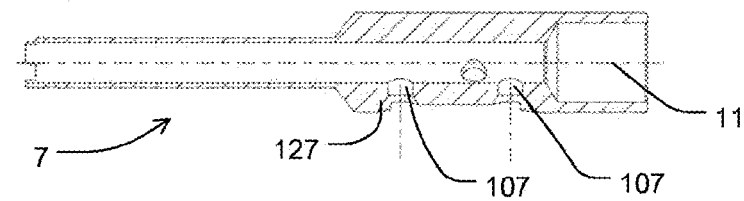

The sleeve 7 of the embodiment in FIG. 44 is explained in more details in FIGS. 45 to 47. The arrangement in FIG. 44 represents a partially assembled state. For further assembly, the sleeve guide 2 is pushed through the sleeve 7. Subsequently, the snap-in pin 39 can be pushed into one of the bores 107. For further assembly, the guiding device 9 is pushed along the longitudinal axis 11 of the sleeve 7 downward (with regard to FIG. 44) in order to releasably connect the intramedullary nail 29 (see FIG. 30) to the guiding device 9.

The tension wheel 67 connects and fixes, in the mounted state, the targeting device 5 and the adjusting device 3 to the guiding bow 1. The tension wheel 67 is explained in more detail in FIG. 48.

The targeting device 5 comprises concentric rings 109 on at least one surface (on the right side in FIG. 4). These purely optical rings serve the user for aligning the current positioning of the targeting device 5, which is arranged movable between the tension wheel 67 and the adjusting device 3.

Furthermore, the targeting device 5 comprises a longitudinal slit 111 on the circumference of the centrical, sleeve-shaped protrusion. This longitudinal slit 111 serves to elastically deform the annular protrusion when inserting an instrument for inserting the interlocking screw 23 (see FIG. 28). In the non-deformed state, the inner diameter of the protrusion is slightly smaller than the diameter of the instrument 23. The protrusion is elastically deformed and widened during the insertion of the instrument 23 and can subsequently be actively moved or rotated, by effort or force against the frictional resistance between the protrusion and the instrument. Due to the frictional resistance, the instrument can only be actively moved, but cannot fall out or decouple. This type of clamping is advantageous when the instrument 23 cannot be permanently manually fixed and held, but still should remain in a predetermined position.

The second section 1*b* of the guiding bow 1 comprises a positioning aid 27 as a bore for further instruments 23' (see FIG. 28) for inserting interlocking screws. This positioning aid 27 comprises also a longitudinal slit 113 (hidden) at one end (in FIG. 44 left), which has the same function as the longitudinal slit 111. Thus, an instrument 23' which is pushed into the bore of the positioning aid 27 is movable on the one hand but is clamped on the other hand due to the frictional resistance to prevent it from falling out or decoupling.

Furthermore, the second section 1*b* comprises a bore 115 for a connecting pin, in particular for a dowel pin. By means of the dowel pin, the second section 1*b* can be connected in particular to an extension (not shown in FIG. 44) in order, for example, to provide further bores for positioning aids for inserting further interlocking screws into the intramedullary nail.

The components shown in FIG. 44 may be made of one or different materials. Particularly, the components second section 1*b*, adjusting device 3, targeting device 5 and Tension wheel 67 are made of plastic; the remaining components are made of one or different metallic materials. Purely exemplarily, the plastic components may be made of, or comprise, one or different types of the following plastic: PEEK (polyetheretherketone); PEEK fiber reinforced; PEEK fiber reinforced in different concentrations of fibers; polyoxymethylene (POM); carbon fiber reinforced plastic (CFRP), polyarylsulfone, in particular polyphenylsulfone (PPSU). Purely exemplarily, the metallic components are made of, or comprise, high-grade stainless steel. The stainless steel can be case hardened and/or blasted.

FIG. 45 shows the sleeve 7 of FIG. 44 in a one-piece view. The longitudinal axis 11 of the sleeve 7 corresponds to the longitudinal axis of the intramedullary nail 19, which can be adapted and fixed at the left end (referring to FIG. 45) by a guiding device 9 (see FIG. 30). For controlling, e.g., the penetration depth of the intramedullary nail, a marking in millimeter is stamped on the sleeve.

Compared to the embodiment of the sleeve 7 in FIGS. 20 to 24, the sleeve 7 does not comprise a sliding guide 33.

FIG. 46 shows the sleeve 7 of FIG. 45 in a view rotated by 90 degrees about the longitudinal axis 11.

FIG. 47 shows the sleeve 7 in a half-section illustration A-A corresponding to the sectional plane shown in FIG. 46.

The guiding bow 1 is positioned relative to the sleeve 7 by means of a snap-in pin 39, according to the mode of operation of the positioning device 100 and the guiding bow 1 already discussed above, for example in FIG. 27 and FIG. 32. The positioning is achieved here through the fact the snap-in pin 39 can be positioned in different bores 107 in the sleeve 7, and due to this positioning an interlocking screw 21 is fixed by an instrument 23 and a targeting device 5 in the intramedullary nail 19 and in the surrounding long bone. The user of the positioning device 100 according to the present invention can thereby select between predetermined bores 107 which interlocking screw 21 he would like to position and fix in the intramedullary nail 19 and the long bone, respectively. With this selection, the snap-in pin 39 should however only be movable only between the predetermined bores 107 in order to enable a fast and accurate fixing. To achieve this goal, the shifting possibilities of the snap-in pin 39 are restricted by, for example, a milled area 119. The shifting direction of the snap-in pin 39 along its longitudinal axis, illustrated by the arrow 121 in FIG. 45, is correspondingly limited, e.g. by stoppers, so that the snap-in pin 39 cannot be withdrawn over or beyond the outer diameter of the sleeve 7. The movement possibilities within the area 119 is clarified and illustrated in FIG. 45 by the gap 123.

In the mounted state of the positioning device 100, the bores 107 are concealed by the sleeve guide 2 of the guiding bow 1. In order to orient the user as to the actual position of the snap-in pin 39, markings 125, e.g. numberings, are impressed on the sleeve 7 in the non-concealed area of its surface. The markings correspond to the associated bores 107, respectively.

The area 119 in the embodiment of FIG. 45 to FIG. 47 is selected purely exemplarily. It may be made for example narrower and smaller in order to constrain or limit the possibilities of guiding the snap-in pin 39 and thus to select a faster and more precise positioning in a bore 107.

The bores 107 are provided with chamfers in order to facilitate inserting the snap-in pin 39 into the bores 107. The bores 107 are provided in particular with fits to allow a play-free positioning.

FIG. 48 shows a further tension wheel 67. The tension wheel 67 comprises in this embodiment asymmetrical engagement contours for the, particularly manual, tightening and releasing. The asymmetrical engagement contour may be referred to as a sawtooth contour. The tension wheel 67 is tightened in the clockwise direction (relative to the top view in FIG. 48) of the rotation direction 129 and released in the counterclockwise direction. The flank in the clockwise direction is much flatter than the flank for release. In this, only a small amount of torque may be applied for tightening. If the torque is increased too much, the hand or fingers in contact will slip over or beyond the nubs 131 when tightening manually. It is thus advantageously possible to achieve that no too high torques may be applied for tightening the tension wheel. Very high torques could cause damage or breakage of this component which is preferably made of plastic.

A tool can also be used alternatively to a pure manual actuation of the tension wheel 67.

The different inclinations of the flanks are defined by the radii 133 and 135. The radius 133 may be approximately 6 mm and the radius 135 may be approximately 49 mm, by way of example.

FIG. 49 a-d show a further positioning device 100''' having additional guiding elements 1c, 1d, 1e for shifting or positioning the targeting device 5. The guiding elements 1c, 1d, 1e are arranged between the sections 1a and 1b of the guiding bow 1 and allow moving the targeting device 5 in x- and y-direction. This moving or movement may happen in addition to moving and/or rotating the guiding bow 1 takes in the sleeve (by the sleeve guide 2). The guiding elements 1c, 1d, 1e and the sections 1a and 1b are sections, elements or single parts of the guiding bow 1.

FIG. 49a shows the further positioning device 100''' having the additional guiding elements 1c, 1d, 1e in a perspective view in a mounted or assembled state. In FIG. 49 b, the positioning device 100''' is shown in perspective view with separate guiding elements 1c, 1d, 1e in FIG. 49c, the positioning device 100''' is shown in a side view in a mounted state and in FIG. 49d in a view turned by 90 degrees with respect to the view of FIG. 49c.

The guiding elements 1c, 1d, 1e are optionally designed as linear guiding elements in a rail shape or slide bearing shape. The guiding elements 1c, 1d, 1e may likewise comprise other embodiments, e.g. designed by roller bearings (e.g. ball bearings), in a curved or bow-shaped design or in another design.

The guiding element 1c is in this embodiment connected to the angle-shaped section 1a of the guiding bow 1. The connection may be done by e.g. a dowel pin and/or by a screw connection.

The guiding element 1d is guided in the guiding element 1c in y-direction. The guide may be done by a T-shaped element, a so-called dovetail guide or another guide.

The guiding element 1e is connected to the section 1b of the guiding bow 1. The connection may e.g. be done by a dowel pin and/or by screw connection.

The guiding element 1e is guided together with the section 1b in the guiding element 1d in x-direction. The guiding may be done by a T-shaped element, a so-called dovetail guide or another guide.

The guiding of the guiding element 1d in the guiding element 1c may be done independent from the guiding of the guiding element 1e in the guiding element 1d. The respective guiding may be done individually or simultaneously.

The guiding elements 1c, 1d, 1e may be made of the same material as the sections 1a and 1b or of other materials. The respective materials may be, for example aluminum, plastic, composite materials or the like.

With the aid of the guiding elements 1c, 1d, 1e, an interlocking screw 21 may be advantageously easily and accurately fixed and positioned in an intramedullary nail 19 see FIG. 39).

Figure 50:
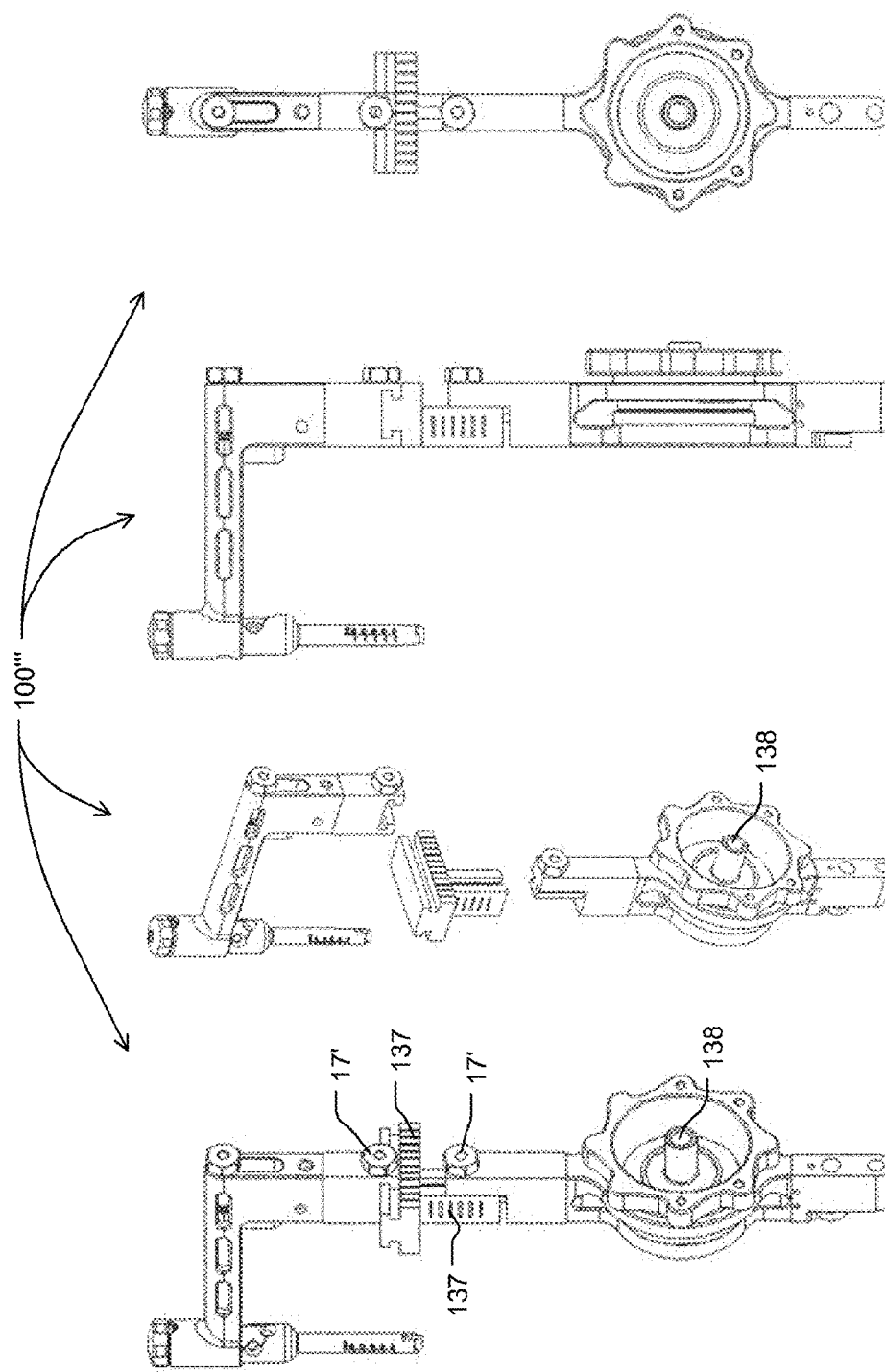

FIGS. 50 a-d show the positioning device 100''' of FIGS. 49 a-c with position markings 137 and fixing screws 17' for the guiding elements.

The positioning markings 137 may be applied markings in the form of lines, line films or the like. Likewise, the positioning markings 137 may be applied by material removal, e.g. by milling, laser markings, engraving or the like.

With the aid of the positioning markings 137, the guiding elements 1c, 1d, 1e may be positioned relative to each other within the scope of the definition and accuracy of the markings. As a result, an interlocking screw 21 may advantageously be quickly, easily and accurately fixed and positioned in an intramedullary nail 19 (see FIG. 39).

FIG. 51 shows a further sliding guide 29 of the sleeve for moving the guiding bow 1 with an additional or further snap-in position 35'. Compared to a middle axis referred to as a zero line 139 (the zero line may be referred to as the central line, initial line or initial position), the further snap-in position 35' is arranged offset by 90 degrees about a position rotated about the longitudinal axis 11. The further snap-in position 35' is not guided through the slide 29.

The lower view in FIG. 51 is rotated by 90 degrees about the longitudinal axis 11 relative to the top view.

For further analogous description of the sleeve 7, reference is made to the description of FIGS. 45-47.

With a further snap-in position 35' offset by 90 degrees, a unique reference position may advantageously be produced or indicated for the user. This will facilitate inserting an interlocking screw 21 into an intramedullary nail 19.

Figure 52B:
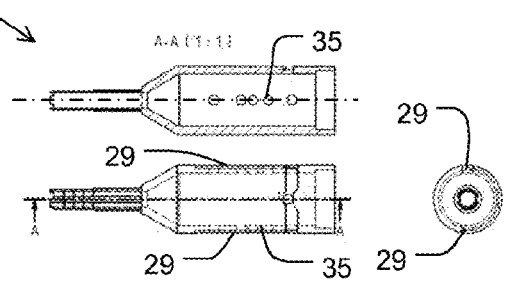

FIGS. 52 a, b show a further line-shaped sliding guide 29 of a sleeve 7. The line-shaped sliding guide 29 may be denoted as U-shaped groove. The sleeve 7 is shown in a perspective view in FIG. 52 a, in a side view at the bottom of FIG. 52 b and at the top of FIG. 52 b in a sectional view A-A the sectional plane of which is shown in the bottom FIG. 52 b. In the illustration at the bottom right of FIG. 52b, the sleeve 7 is shown in a front view rotated by 90 degrees (relative to the illustration at the bottom left).

The two-line shaped sliding guides 29 are arranged offset by 180 degrees about the longitudinal axis 11 and connected to each other by a partly annular slide. The line-shaped sliding guides 29 comprise several snap-in positions 35.

FIG. 53 shows a further sliding guide 29 with a stopper 141. The bar-shaped stopper 141 may advantageously prevent a slipping of the guiding bow 1, guided in the slide, towards the interlocking screw 21 (in FIG. 53 to the left), which interlocking screw 21 is inserted into the intramedullary nail 19 by the guiding bow 1 (see for example FIG. 39). The stopper 141 may be described as a securing against an undesired shifting of the guiding bow 1.

The upper view in FIG. 53 is a perspective view, the lower illustration in FIG. 53 is a side view of the sleeve 7.

FIG. 54 shows a sleeve with a written marking 143. By this written marking, it is possible to indicate the exact position of the guiding bow 1 relative to the sleeve 7 and thus also to the intramedullary nail 19 which is connected to the sleeve 7. This may advantageously allow a simpler and faster positioning and fixing of the interlocking screw 21 in the intramedullary nail 19.

FIGS. 55 a, b show a reinforced guiding bow 1. The rib-shaped or honeycomb-shaped reinforcements 145 may effect an increased stability of the entire guiding bow 1. By such a reinforced guiding bow 1, it is advantageously possible to achieve a more stable or stiffer and thus more accurate guiding of the targeting device 5 in the guiding bow 1 and a more accurate and faster positioning and fixing of the interlocking screw 21 in the intramedullary nail 19.

The view in FIG. 55 a is a side view of the reinforced guiding bow 1, the view in FIG. 55 b is of the reinforced guiding bow 1.

FIG. 56 shows a guiding bow 1 being optimized by injection molding and having rib-shaped stiffeners 147 in an inner structure of the guiding bow 1. The stiffeners may be weight-saving with respect to a solid material and may advantageously facilitate easier handling of the guiding bow 1.

The form of the guiding bow 1 optimized by injection molding allows an easy production of the guiding bow 1, for example by optimized contour forms (rounded forms).

FIGS. 57 a-c show an adjusting mechanism 149 of the targeting device 5. The targeting device 5 may be translationally shifted and/or rotated within the adjusting mechanism 149 in order to align the interlocking screw 21 to the intended through-openings 25 in the intramedullary nail 19. The adjusting mechanism 149 allows an advantageous fast and easy alignment of the interlocking screw 21 and may be releasably locked in the desired position via a clamping mechanism 150 located within the adjusting mechanism 149 on the circumference of the adjusting mechanism 149. The adjusting mechanism 149 is rotatably mounted in the guiding bow 1 in a freely rotatable manner. The position of the adjusting mechanism 149 selected in relation to the guiding bow 1 may be frictionally releasably fixed by the tension wheel 67.

FIG. 57a shows a sectional view of the sectional plane A-A marked in FIG. 57b, FIG. 57b shows a top view and FIG. 57c shows a perspective view.

FIGS. 58 a-c show a further adjusting mechanism 149' of the targeting device 5. Unlike the embodiment in FIGS. 57 a-c, the targeting device 5 is not directly releasably fixed by clamping to the adjusting mechanism 149'; but rather directly to the guiding bow 1.

FIG. 58a shows a sectional view of the sectional plane A-A marked in FIG. 58b, FIG. 58b shows a top view and FIG. 58c shows a perspective view.

FIGS. 59 a-c show the targeting device 5 in various views with a spring mechanism for fixing an instrument 23. The instrument 23 (see e.g. FIG. 39) may be plugged or inserted in the central guide or bore or through-opening of the targeting device 5. The instrument 23 may be frictionally fixed using the longitudinal slot 111 and/or the cross slot 112 and by a spring effect of the materials surrounding the slots 111, 112. Thus, the instrument 23 may be advantageously positioned more easily without the instrument 23 slipping out of place on its own or sliding out of the central guide. The spring effect and the frictional force are advantageously designed such that a manual shifting of the instrument 23 is easily possible FIGS. 60 a-c show a distal attachment 151 in various views with a spring mechanism. The distal attachment 151 may be connected to the second section of the guiding bow 1b. By using said distal attachment a further instrument 23' (see for example FIG. 28) may be used for inserting interlocking screws. The distal attachment 151 comprises at least one longitudinal slot 113 and/or one cross slot 114. The further instrument 23' may be frictionally fixed by a spring effect of the material surrounding the slots 113, 114. Thus the instrument 23' may advantageously be positioned more easily without the instrument slipping on its own or sliding on the guide. The spring effect and the frictional force are advantageously designed such that a manual shifting of the instrument 23 is easily possible.

LIST OF REFERENCE NUMERALS x x-direction
y y-direction
z z-direction
100, 100',
100", 100''' positioning device
200, 200' positioning device module
201 joint, ball joint
202 alignment lines
203 receiving section
204 main extension plane
205 ball of the ball joint
206 second plane
207 annular slot
209, 209' position marking
211 fixing device, fixing mechanism
213 bar
215 through-opening in the adjusting device
217 adjusting fork
219 plug-in bolt
221 cylindrical shoulder
223 imaging device; X-ray C-arm
225 crosshair of the imaging device
227 fixing device; clamping lever
229 position marker
229a single crosshair of the adjusting fork
229b ring marker of the adjusting fork
229c ball marker of the adjusting fork
231 double crosshair of the adjusting fork
233 drill arrangement
235, 235' tissue protective sleeve
236 drill bushing
237 drill
239 step drill
241 shoulder 243, 243' scale
245 drill bit
247 drill bit bracket or yoke
248 pins
249 drill bit rail
251 through-opening in the drill bit rail
253 eccentric rod
255 lever of the eccentric rod
257 spring element, spiral spring
259 fixing screw, tangent screw
261 fork
263 hinge
265 eccentric
267 threaded rod
269 screw
270 tensioning device
271 pin
300 upper arm bone, humerus, long bone
400 set
401 extension device
403 adapter
405 clamping screw
407 fastening screw
409 field of view
411 scale on the extension device
501 joystick
502 guiding device
504 first wedge plate
505 second wedge plate
506 threaded plate
507 eccentric
508 nut
509 joystick latches
510 latching plate
511 latching plate latches
512 upper side of the receiving section
513 latching device
514 tissue protection sleeve guide
1 guiding bow
1a first area or section of the guiding bow
1b second area or section of the guiding bow
1c,1d,1e guiding element
2 sleeve guide
3 adjusting device
5 targeting device
7 sleeve
9 guiding device
11 longitudinal axis of the sleeve; longitudinal axis of the long bone
13 circumferential direction of the sleeve
15, 15' snap-in arrangement
17, 17' fixing screw
19 intramedullary nail
21, 21' interlocking device, interlocking screw
23, 23' instrument for inserting the interlocking device or the interlocking screw
25 through-opening in the intramedullary nail
26a, 26a', 26b distal through-opening
27 positioning aid
28 inner thread
29 sliding guide
31 guide step or landing
33 groove-shaped extension of the sliding guide in the circumferential direction of the sleeve
35, 35' snap-in position; long holes in the sleeve
37 marking for position control
39 snap-in pin; bolt of the snap-in arrangement
41 leaf spring
43 bolt arrangement
45 lever
47 gear connection
49 sleeve bar
51 thread
53 pin; mounted in radial direction by a spring or in a springy manner
55 tool
57 connector or bushing
59 lever
60 movement direction of the lever; arrow direction
61 magnet
63 magnet
65 connecting screw
67 tension wheel
69 spiral spring for snap-in pin
71 handpiece
73 leaf spring
75 lever
77 thread on the snap-in pin
79 thread of or for the two-piece targeting device
81 snap-in device
83 hole arrangement
85 fixing screw
87 point-shaped or punctiform fixation
89 wing screw
91 spiral spring for targeting device
93 protrusion on the upper surface of the targeting device
95 bores or holes in the bottom of the adjusting device
97 thread for targeting device
99 screw
101 interface between the first and the second section of the guiding bow
103 bolt; dowel pin
105 pin
107 bores of the sleeve
109 concentric rings of the targeting device
111 longitudinal slot of the sleeve-shaped edge of the targeting device
113 longitudinal slot of the positioning aid
114 transverse slot
115 bore for dowel pin
117 marking in millimeters
119 range of movement by snap-in pin
121 movement direction of the snap-in pin
123 gap width for moving the snap-in pin
125 markings
127 chamfer
129 rotation direction of the tension wheel
131 nubs
133 first radius of the tension wheel
135 second radius of the tension wheel
137 positioning marking
138 through-opening, through-bore
139 guiding opening
140 guiding device
141 stopper
143 written marking
145 honeycomb reinforcement
147 rib-shaped stiffener
149, 149' adjusting mechanism
150 clamping mechanism
151 distal attachment

The invention claimed is:
1. A positioning device module assembly configured for releasable connection to a positioning device, wherein the positioning device module assembly is configured to position and/or fix an intramedullary nail in a long or hollow bone, configured to fix an osteosynthesis plate to a long or hollow bone and/or configured to fix a prosthesis in a long or hollow bone, the positioning device module assembly comprising:

a targeting device for receiving at least one interlocking device or an instrument for acting on the at least one interlocking device;
a receiving section for receiving the targeting device;
a section for connecting the positioning device module assembly to the positioning device;
an adjusting device for receiving the targeting device or for acting thereon, wherein the targeting device is arranged in or at the adjusting device and is positionable relative thereto, and wherein the receiving section is configured for receiving the targeting device and the adjusting device; and
a joint or a deformable section for rotating or twisting or moving or pivoting the positioning device module assembly, wherein the joint or the deformable section comprises at least one rotary axis.

2. The positioning device module assembly according to claim 1, further comprising a fixing device for releasably interlocking the joint.

3. The positioning device module assembly according to claim 1, wherein the joint is a cylindrical joint, a pivot or rotational joint or a ball joint.

4. The positioning device module assembly according to claim 1, wherein the deformable section is, or comprises, a plastically deformable metal and/or a plastically deformable composite material.

5. The positioning device module assembly according to claim 1, wherein the targeting device is arranged to be rotatable and/or translationally movable in the adjusting device.

6. The positioning device module assembly according to claim 1, comprising a force-fit fixing mechanism and/or a form-fit fixing mechanism for interlocking or fixing the targeting device in, at or relative to the adjusting device.

7. The positioning device module assembly according to claim 1, further comprising a positioning aid for aligning the positioning device module assembly.

8. The positioning device module assembly according to claim 1, wherein the targeting device comprises at least one, two, or several through-openings for receiving the at least one interlocking device or an instrument for acting on the at least one interlocking device.

9. The positioning device module assembly according to claim 1, wherein the at least one interlocking device is at least one first interlocking device, the positioning device module assembly further comprising a drill bit for engaging with a second interlocking device or an instrument for acting on the second interlocking device.

10. The positioning device module assembly according to claim 9, wherein a longitudinal axis of the second interlocking device, or a longitudinal axis of the instrument for acting on the second interlocking device or a longitudinal axis of a through-opening of the drill bit is aligned at an angle between 80 and 100 degrees to a longitudinal axis of the at least one first interlocking device, to a longitudinal axis of a through-opening of the targeting device or to a longitudinal axis of the instrument for acting on the at least one first interlocking device.

11. The positioning device module assembly according to claim 10, wherein the drill bit is connected or connectable to the targeting device.

12. The positioning device module assembly according to claim 10, wherein the drill bit comprises at least one drill bit rail being adjustable in length or longitudinally movable.

13. The positioning device module assembly according to claim 12, wherein the at least one drill bit rail is adjustable in length or longitudinally movable for positioning the at least one first interlocking device.

14. A set comprising a positioning device module assembly according to claim 1 and an extension device for connecting the positioning device module assembly to a positioning device.

15. The set according to claim 14, further comprising an adapter for connecting the extension device to the positioning device, wherein a position of the positioning device module assembly connected to the extension device is changeable or variable.

16. The set according to claim 14, wherein at least one through-opening of the targeting device is configured to be aligned perpendicular to a longitudinal axis of the intramedullary nail and/or wherein at least one through-opening of the targeting device is configured to be aligned obliquely to a longitudinal axis of the intramedullary nail.

17. The set according to claim 16, wherein the at least one through-opening of the targeting device is configured to be aligned obliquely to the longitudinal axis of the intramedullary nail at an angle between 50 and 80 degrees to the longitudinal axis of the intramedullary nail.

18. The positioning device module assembly according to claim 1, wherein the section for connecting the positioning device module assembly to the positioning device is configured for releasably connecting the positioning device module assembly to the positioning device.

* * * * *